(12) United States Patent
Stephens et al.

(10) Patent No.: US 7,253,275 B2
(45) Date of Patent: Aug. 7, 2007

(54) **PORIN B (PORB) AS A THERAPEUTIC TARGET FOR PREVENTION AND TREATMENT OF INFECTION BY *CHLAMYDIA***

(75) Inventors: Richard S. Stephens, Orinda, CA (US); Diane Kawa, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/414,278

(22) Filed: Apr. 27, 2006

(65) Prior Publication Data

US 2006/0233826 A1 Oct. 19, 2006

Related U.S. Application Data

(62) Division of application No. 10/094,407, filed on Mar. 7, 2002, now Pat. No. 7,105,171.

(51) Int. Cl.
| | | |
|---|---|---|
| C07H 21/04 | (2006.01) | |
| C07H 21/02 | (2006.01) | |
| C07K 2/00 | (2006.01) | |
| C07K 1/00 | (2006.01) | |

(52) U.S. Cl. .................... 536/23.7; 536/23.1; 530/350; 530/300; 530/825

(58) Field of Classification Search ................ 536/23.7, 536/23.1; 530/350, 300, 825
See application file for complete search history.

(56) References Cited

U.S. PATENT DOCUMENTS

| | | | | |
|---|---|---|---|---|
| 4,267,170 A | 5/1981 | Seawell | ......................... | 424/88 |
| 4,271,146 A | 6/1981 | Seawell | ......................... | 424/89 |
| 5,242,686 A | 9/1993 | Chu et al. | ...................... | 424/92 |
| 5,656,271 A | 8/1997 | MacDonald et al. | ..... | 424/131.1 |
| 5,716,793 A | 2/1998 | MacDonald et al. | ........ | 435/7.36 |
| 5,725,863 A | 3/1998 | Daniels et al. | ............ | 424/263.1 |
| 5,770,714 A | 6/1998 | Agabian et al. | ............ | 536/23.1 |
| 5,821,055 A | 10/1998 | Agabian et al. | ................ | 435/6 |
| 5,840,297 A | 11/1998 | MacDonald et al. | ..... | 424/131.1 |
| 5,972,350 A | 10/1999 | Atherton et al. | ......... | 424/263.1 |
| 7,105,171 B2 * | 9/2006 | Stephens et al. | ......... | 424/263.1 |

FOREIGN PATENT DOCUMENTS

| | | |
|---|---|---|
| WO | WO 94/06827 A1 | 3/1994 |
| WO | WO 96/31236 A1 | 10/1996 |
| WO | WO 97/41889 A1 | 11/1997 |
| WO | WO 98/02546 A2 | 1/1998 |
| WO | WO 98/10789 A1 | 3/1998 |
| WO | WO 98/58953 A2 | 12/1998 |
| WO | WO 99/10005 A1 | 3/1999 |
| WO | WO 99/28475 A2 | 6/1999 |
| WO | WO 9928475 A2 | 6/1999 |
| WO | WO 0156605 A1 | 8/2001 |

OTHER PUBLICATIONS

Allen, et al. "*A single peptide from the major outer membrane protein of Chlamydia trachomatis elicits T cell help for the production of antibodies to protective determinants*", The Journal of Immunology vol. 147(2): 674-679 (1991).
Bavoil, et al. "*Role of disulfide bonding in outer membrane structure and permeability in Chlamydia trachomatis*", Infection and Immunity vol. 44(2): 479-485 (1984).
Berman, et al. "*Recommendations for the prevention and management of Chlamydia trachomatis infections*", The Morbidity and Mortality Weekly Report vol. 42(RR-12): 1-102 (1993).
Caldwell, et al. "*Purification and partial characterization of the major outer membrane protein of Chlamydia trachomatis*", Infection and Immunity vol. 31(3): 1161-1176 (1981).
Everett, et al. "*Architecture of the cell envelope of Chlamydia psittaci 6BC*", Journal of Bacteriology vol. 177(4): 877-882 (1995).
Fan, et al. "*Antigen conformation dependence of Chlamydia trachomatis infectivity neutralization*", The Journal of Infectious Diseases vol. 176: 713-721 (1997).
Filip, et al. "*Solubilization of the cytoplasmic membrane of Escherichia coli by the Ionic detergent sodium-lauryl sarcosinate*",

OTHER PUBLICATIONS

Sanchez-Campillo, et al. "*Identification of immunoreactive proteins of Chlamydia trachomatis by western blot analysis of a two-dimensional electrophoresis map with patient sera*", Electrophoresis vol. 20: 2269-2279 (1999).

Sardinia, et al. "*Developmental regulation of the cysteine-rich outer-membrane proteins of murine Chlamydia trachomatis*" Journal of General Microbiology vol. 134: 997-1004 (1988).

Stephens, et al. "*High-resolution mapping of serovar-specific and common antigenic determinants of the major outer membrane protein of Chlamydia trachomatis*", J. Exp. Med. vol. 167: 817-831 (1988).

Stephens, et al. "*Genome sequence of an obligate intracellular pathogen of humans: Chlamydia trachomatis*", Science vol. 282: 754-759 (1998).

Stephens, et al. "*Antigen Variation of Chlamydia trachomatis*", In J.W. Moulder (ed.), Intracellular Parasitism, CRC Press, Boca Raton, pp. 51-62.

Su, et al. "*Protective efficacy of a parentally administered MOMP-derived synthetic oligopeptide vaccine in a murine model of Chlamydia trachomatis genital tract infection: Sertum neutralizing IgG antibodies do not protect against chlamydial genital tract infection*", Vaccine vol. 13(11): 1023-1032 (1995).

Thylefors, et al. "*Global data on blindness*", Bulletin of World Health Organization vol. 73(1): 115-121 (1995).

Tuffrey, et al. "*Heterotrophic protection of mice against Chlamydial salpingitis and colonization of the lower genital tract with a human serovar F isolate of Chlamydia trachomatis by prior immunization with recombinant serovar L1 major outer-membrane protein*", Journal of Gen Microbiology vol. 138: 1707-1715 (1992).

Wyllie, et al. "*The major outer membrane protein of Chlamydia psittaci functions as a porin-like ion channel*", Infection and Immunity vol. 66(11): 5202-5207 (1998).

Burgess et al. Possible dissociation of the heparin-binding and mitogenic activities of heparin-binding (acidic fibroblast) growth factor-1 from its receptor-binding activities by site-directed mutagenesis of a single lysine residue.J. Cell Biol. 1990, 111:2129-2138.

Bowie, et al. Deciphering the message in protein sequences: tolerance to amino acid substitutions. Science 1990, 247: 1306-1310.

Lazar et al. Transforming growth factor alpha: mutation of aspartic acid 47 and leucine 48 results in different biological activities. Mol. Cellular Biol. 1988, 8: 1247-1252.

Skolnick et al. From genes to protein structure and function: novel applications of computational approaches in the genomic era. Trends in Biotechnology, 2000, 18: 34-39.

GenBank Accession No. AAC68308 published Oct. 30, 2000.
GenBank Accession No. AEO01342 AE001273 published Oct. 30, 2000.
GenBank Accession No. H71479 published Oct. 8, 1999.
GenBank Accession No. NP_225049 published Sep. 10, 2001.
GenBank Accession No. CAC44728 published Jul. 25, 2001.
GenBank Accession No. H81742 published May 11, 2000.
GenBank Accession No. AAF38966 published May 26, 2000.
GenBank Accession No. NP_220232 published Sep. 10, 2001.
GenBank Accession No. P38006 published Aug. 20, 2001.
GenBank Accession No. NP_296470 published Oct. 2, 2001.
GenBank Accession No. Q9PLL3 published Oct. 16, 2001.
GenBank Accession No. AAO67537, Mar. 27, 2003.
GenBank Accession No. AAO67531, Mar. 27, 2003.
GenBank Accession No. AAO67530, Mar. 27, 2003.
GenBank Accession No. NP_220232, May 19, 2003.
GenBank Accession No. NP_296470, Aug. 1, 2003.
GenBank Accession No. NP_829774, Aug. 1, 2003.
GenBank Accession No. NP_225049, Dec. 10, 2002.
GenBank Accession No. NP_877155, Jul. 25, 2003.

* cited by examiner

```
              10              20              30             40
CTD PorB  M S S K L V N Y L R L T F L S F L G I A S T S L D A M P A G N P A F P - - V I P
CTD MOMP  M K K L L K S V L V F A A L S - - - - S A S S L Q A L P V G N P A E P S L M I D 50              60              70             80
CTD PorB  G I N I E Q K N A C S F D L C N S Y D V L S A L S G N L K L C F C G D Y I F S E
CTD MOMP  G I L W E G F G G D P C D P C A T W C D A I S M R V G Y Y G D F V F D R V L K T 90             100             110            120
CTD PorB  E A Q V K D V P V V T S V T T A G - - V G P S P D I T S T T K T R N F D L V N C
CTD MOMP  D V N K E F Q M G A K P T T D T G N S A A P S T L T A R E N P A Y G R H M Q D A 130             140             150            160
CTD PorB  N L N T N C V A V A F S L P D R S L S A I P L F D V S F E V K - - V G G L K Q Y
CTD MOMP  E M F T N A A C M A L N I W D R F D V F C T L G A T S G Y L K G N S A S F N L V 170             180             190            200
CTD PorB  Y R L P M N A Y R D F T S E P L N S E S E V T D C M I E V Q S N Y G F V W D V S
CTD MOMP  G L F G D N E N Q K T V K A E S V P N M S F D Q S V V E L Y T D T T F A W S V G 210             220             230            240
CTD PorB  L K K V I W K D G V S F V G V G A D Y R H A S - - - - - - - - - C P I D Y I I A
CTD MOMP  A R A A L W E C G C A T L G A S F Q Y A Q S K P K V E E L N V L C N A A E F T I 250             260             270            280
CTD PorB  N S - - - - - - - - - - - - Q A N P E V F I A D S D G K L N F K E W S V C V G
CTD MOMP  N K P K G Y V G K E F P L D L T A G T D A A T G T K D A S I D Y H E W Q A S L A 290             300             310            320
CTD PorB  L T T Y V N D Y V L P Y L - - - - - - - - A F S I G S V S R Q A P D - - - - - - -
CTD MOMP  L S Y R L N - M F T P Y I G V K W S R A S F D A D T I R I A Q P K S A T A I F D 330             340             350            360
CTD PorB  - - - - - - - - - - - - - - D S F K K L E D R F T N L K F K V R K I T S H
CTD MOMP  T T T L N P T I A G A G D V K T G A E G Q L G D T M Q I V S L Q L N K M K S R K 370             380             390         SEQ ID NO:2
CTD PorB  R G N I C I G A T N Y V A D N F F Y N V E G R W G S Q R A V N V S G G F Q F
CTD MOMP  S C G I A V G T T I V D A D K Y A V T V E T R L I D E R A A H V N A Q F R F
                                                             SEQ ID NO:3
```

PORIN B (PORB) AS A THERAPEUTIC TARGET FOR PREVENTION AND TREATMENT OF INFECTION BY *CHLAMYDIA*

This application is a Divisional application of application Ser. No. 10/094,407, filed Mar. 7, 2002, now U.S. Pat. No. 7,105,171.

STATEMENT AS TO FEDERALLY SPONSORED RESEARCH

This invention was made, at least in part, with a government grant from the National Institutes of Health (Grant Nos. NIH grants AI40250, AI39258, and AI42156). Thus, the U.S. government may have certain rights in this invention.

FIELD OF THE INVENTION

The invention relates generally to the field of treatment, prevention, and diagnosis of infectious disease, particularly to prevention of infectious disease caused by the bacterial pathogen *Chlamydia* and *Chlamydophila* (formerly classified as, for example, *C. psittacci* and *C. pneumoniae*).

BACKGROUND OF THE INVENTION

*Chlamydiae* are obligate intracellular pathogens that cause a spectrum of diseases including trachoma, the leading cause of preventable blindness worldwide, as well as a variety of sexually transmitted diseases such as lymphogranuloma venereum, urethritis, cervicitis, endometritis, and salpingitis (Thylefors et al. (1995) Bull W H O 73:115-121). For example, *Chlamydia trachomatis* is considered the world's most common sexually transmitted bacterial pathogen (Schachter and Grayston (1998) Presented at the Ninth international symposium on human *chlamydial* infection, Napa, Calif.; World Health Organization, 1996, Global prevalence and incidence of selected curable sexually transmitted diseases: overview and estimates). Currently an estimated 400 million people have active infectious trachoma, while 90 million have a sexually transmitted disease caused by *C. trachomatis* (World Health Organization, 1996). *Chlamydia pneumoniae* usually infects the lungs and causes no more than a mild cold; however, it can travel to the blood vessels and thrive in clots, causing heart disease. Diseases caused by *Chlamydia* represent significant health problems worldwide.

Growth of *Chlamydia* generally depends on the acquisition of host ATP and other high-energy metabolites from the host (Moulder et al. (1991) Microbiol. Rev. 55:143-90). *Chlamydiae* have the enzymatic machinery for the Embden-Meyerhoff pathway (EMP), the pentose phosphate pathway. (PPP), and the tricarboxylic acid (TCA) cycle (Kalman et al. (1999) Nat. Genet. 21:385-9; Stephens et al. (1998) Science 282:754-9). The TCA in *chlamydia* is incomplete in that the host lacks three enzymes: citrate synthase, aconitase, and isocitrate dehydrogenase (Kalman et al., ibid,; Stephens et al., ibid.). This observation suggests that the glutamate and α-ketoglutarate are obtained from the host cell since these cannot be synthesized by the bacterium. It has been shown that *chlamydiae* utilize glucose as the major source of carbon, but that dicarboxylates also serve to support *chlamydial* viability and growth (Iliffe-Lee et al. (2000) Mol. Microbiol. 38:20-30).

Treatment for *Chlamydia* infection typically involves administration of an antimicrobial drug such as azithromycin, doxycycline, ofloxacin, erythromycin, or amoxicillin (Centers for Disease Control and Prevention. Recommendations for the prevention and management of *Chlamydia trachomatis* infections. Morb Mortal Wkly Rep 1993; 42 (RR-12): 1-102). These conventional treatments are problematic for several reasons, including patient non-compliance with multi-day, multi-dose regimens and side effects such as gastrointestinal problems. Furthermore, treatment of *Chlamydia* with existing antimicrobial drugs may lead to development of drug resistant bacterial strains, particularly where the patient is concurrently infected with other common bacterial infections.

In addition, *chlamydial* infections often have no overt symptoms, so irreversible damage can be done before the patient is aware of the infection. Therefore, prevention of the infection is considered the best way to protect from the damage caused by *Chlamydia*. Therefore, the development and production of effective *chlamydial* vaccines, more effective treatments once infection is established, and sensitive and specific diagnostic assays are important public health priorities.

*Chlamydia* have a unique developmental growth cycle with morphologically distinct infectious and reproductive forms, elementary bodies (EB) and reticulate bodies (RB), respectively. The outer membrane proteins of EB are highly cross-linked with disulfide bonds. The *chlamydial* outer membrane complex (COMC), which includes the major outer membrane protein (MOMP), is a major component of the *chlamydial* outer membrane. The COMC is made up of a number of cysteine-rich proteins (Everett et al. (1995) *J. Bacteriol.* 177:877-882; Newhall et al. (1986) *Infect. Immun.* 55:162-168; Sardinia et al. (1988) *J. Gen. Microbiol.* 134:997-1004), as determined by the insolubility of proteins in the weak anionic detergent N-lauryl sarcosinate (Sarkosyl). Insolublity of proteins in Sarkosyl is a characteristic of integral outer membrane proteins of gram-negative bacteria (Filip et al. (1973) *J. Bacteriol.* 115:717-722). The COMC is present on the outer membrane proteins of EB, but not of RB. In contrast, MOMP is present throughout the developmental cycle in both EB and RB and is thought to have a structural role due to its predominance and extensive disulfide crosslinking in the EB membrane. Another function of MOMP is as a porin which allows for non-specific diffusion of small molecules into *Chlamydia* (Bavoil et al. (1984) *Infect. Immun.* 44:479-485, Wyllie et al. (1998) *Infect. Immun.* 66:5202-5207).

As with many pathogens, the development of a vaccine to *Chlamydia* has proven difficult. Much of the focus for a vaccine candidate has been on the *chlamydial* major outer membrane protein (MOMP) (see, e.g., U.S. Pat. Nos. 5,770, 714 and 5,821,055; and PCT publication nos. WO 98/10789; WO 99/10005); WO97/41889 (describing fusion proteins with MOMP polypeptides); WO98/02546 (describing DNA immunization based on MOMP-encoding sequences); WO 94/06827 (describing synthetic peptide vaccines based on MOMP sequences); WO 96/31236). MOMP has been estimated to make up over 60% of the total outer membrane of *Chlamydia* and is an exposed surface antigen (Caldwell et al. (1981) *Infect. Immun.* 31:1161-1176) with different sequence regions conferring serotype, serogroup and species reactivities (Stephens et al. (1988) *J. Exp. Med.* 167:817-831). The protein consists of five conserved segments and four variable segments with the variable segments corresponding to surface exposed regions and conferring serologic specificity (Stephens et al. (1988) *J. Exp. Med.* 167:

817-831). It has been suggested that these variable segments provide *Chlamydia* with antigenic variation, which in turn is important in evading the host immune response (Stephens, 1989 "Antigenic variation of *Chlamydia trachomatis*," p. 51-62. In J. W. Moulder (ed.), Intracellular Parasitism. CRC Press, Boca Raton.). A potential problem in making a vaccine to an antigenically variant region is that a vaccine to one region of MOMP may only confer protection to that serovar. Also, making a subunit vaccine to an antigenic variable region may prove difficult since conformational antigenic determinants may be essential to elicit effective immunization (Fan et al. (1997) *J. Infect. Dis.* 176:713-721). Although the use of MOMP as a vaccine still seems promising, these potential problems strongly suggest that other vaccine targets should be explored.

Other proposed *Chlamydia* vaccine targets have been described and include, for example, glycolipid exoantigen (see, e.g., U.S. Pat. Nos. 5,840,297; 5,716,793 and 5,656,271). Other *Chlamydia* vaccines have used other proteins (see, e.g, PCT publication no. WO 98/58953, describing a surface protein of *C. pneumoniae*) or a cocktail of proteins (see, e.g., U.S. Pat. Nos. 5,725,863; and 5,242,686) or have used live or attenuated whole bacteria (see, e.g., U.S. Pat. Nos. 5,972,350; 4,267,170; and 4,271,146). The sequencing of the genome of *C. trachomatis* has provided a tool to identify candidate vaccine targets (Stephens et al. (1998) *Science* 282:754-759) and examination of antibodies present in serum of infected individuals (Sanchez-Campillo et al. (1999) *Electrophoresis* 20:2269-79) have provided tools for the identification of additional vaccine targets.

There is a need in the field for the development of chemotherapeutics and vaccines that provide protection against *Chlamydia* and *Chlamydiophila* infection. The present invention addresses these needs.

SUMMARY OF THE INVENTION

The present invention features peptides of a PorB polypeptide, which PorB peptides are useful in production of antibodies that bind the full-length PorB polypeptide and as a therapeutic agent. In specific embodiments the invention features a composition comprising one or more PorB peptides (other than a full-length PorB polypeptide), which peptides contain at least one epitope that can elicit *Chlamydia*-neutralizing antibodies. The invention also features methods for induction of a protective immune response against infection by *Chlamydia* and *Chlamydiophila*.

BRIEF DESCRIPTION OF THE DRAWINGS

FIG. 1 is an alignment of the amino acid sequences of PorB (SEQ ID NO:2) and MOMP (SEQ ID NO:3).

FIG. 2 is a schematic showing the alignment of the amino acid sequences of PorB from *C. trachomatis* serovars D (CT-D) (SEQ ID NO:2), L2 (CT-L2) (SEQ ID NO:5), and C (CT-C) (SEQ ID NO:6), as well as the amino acid sequence of PorB from *C. pneumoniae* (CPn) (SEQ ID NO:4). *C. trachomatis* serovar L2 and C differences are indicated below the amino acid sequence. The cysteines are indicated with an asterisk above the amino acid sequence.

Figure 3:
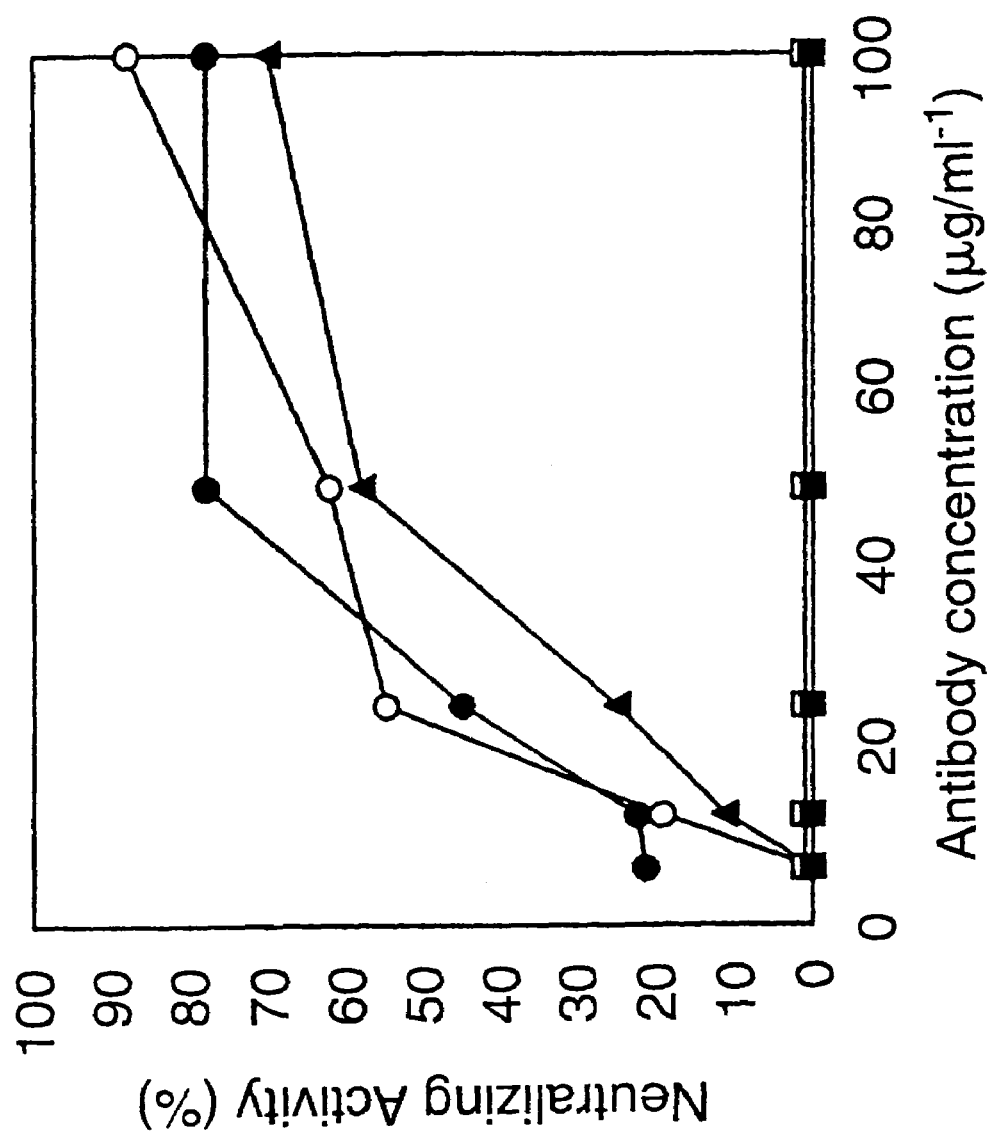
FIG. 3 is a graph showing antibody neutralization of *C. trachomatis* serovar L2 in HaK cells. Results are expressed as percentage reduction in inclusion-containing cells with respect to number of inclusion-containing cells observed after incubation with SPG only. The antibodies used were anti-PorB (open circles), anti-PorB$^{24-71}$ (closed triangles), IH5 (closed circles), anti-pgp3 (open squares) and pre-immune serum (closed squares).

"Treatment" or "treating" as used herein means any therapeutic intervention in a subject, usually a mammalian subject, generally a human subject, including: (i) prevention, that is, causing the clinical symptoms not to develop, e.g., preventing infection and/or preventing progression to a harmful state; (ii) inhibition, that is, arresting the development or further development of clinical symptoms, e.g., mitigating or completely inhibiting an active (ongoing) infection so that bacterial load is decreased to the degree that it is no longer seriously harmful, which decrease can include complete elimination of an infectious dose of a *Chlamydia* bacteria from the subject; and/or (iii) relief, that is, causing the regression of clinical symptoms, e.g., causing a relief of fever, inflammation, and/or other symptoms caused by an infection.

By the term "neutralizing epitope" as used herein is intended an amino acid sequence that defines an antigenic determinant which is bound by an antibody and, in the context of infection, reduces infectivity of a *Chlamydial* bacterium, e.g., by reducing the efficiency of bacterial interaction with host cells important in establishing bacterial infection or disease in the host, facilitating bacterial clearance, and the like. "Neutralization" is intended to encompass any biological activity of the bacteria, including reduction in the efficiency or ability of the bacterium to establish infection or cause disease or disease symptoms, inhibition of chlamydial EB formation, and the like.

As used herein, the term "neutralizing antibodies" refers to antibodies which bind a neutralizing epitope as described above.

By "neutralizing domain" is meant a sequence of contiguous amino acids, which sequence defines at least one neutralizing epitope.

Overview

The invention is based on the discovery of amino acid sequences of the *chlamydial* outer membrane porin protein, PorB, of *C. trachomatis* that define neutralizing epitopes. The inventors have identified at least four domains of the PorB polypeptide which comprise at least one neutralizing epitope. Polypeptides comprising at least one of these domains can be used to generate neutralizing antibodies against *Chlamydia*. In addition, the inventors have shown that the neutralizing epitopes of PorB elicit antibodies that are cross-reactive with PorB of other *chlamydial* species. The PorB peptides of the invention thus are useful in eliciting production of PorB-specific antibodies, which antibodies can be used in, for example, detection or full-length PorB polypeptide, purification of PorB, and can also serve as the basis for production of an effective vaccine In one embodiment of particular interest, the Invention features PorB polypeptides comprising neutralizing epitopes, as well as methods of use of such polypeptide to facilitate induction an immune response to neutralize *Chlamydia* infection.

PorB has several characteristics that make it an effective vaccine and chemotherapeutic target. Unlike other vaccine candidates such as MOMP, PorB does not vary substantially in its amino acid sequence between serovars and was instead highly conserved among the *C. trachomatis* strains tested. This lack of variable regions indicates that PorB does not participate in antigenic variation that contributes to evasion of the immune response. PorB sequences between *C. trachomatis* and *C. pneumoniae* are also conserved further supporting a requirement for constrained sequence to ensure its specific function, and providing further evidence that a vaccine based on a PorB polypeptide from one *chlamydial* species is cross-reactive with another *chlamydial* species, and thus can provide for induction of an immune response that can provide immunoprotection across chlamydial species.

The invention thus provides compositions comprising a polypeptide comprising at least one neutralizing epitope, and methods of inducing anti-*chlamydial* immunity based on these vaccines. In addition, the invention also provides for detection of PorB polypeptides comprising at least one neutralizing epitope or PorB-encoding sequences in diagnosis of *Chlamydia* infection.

The invention further features methods of identifying anti-*chlamydial* chemotherapeutics based upon identification of agents that inhibit PorB function in α-ketoglutarate transport.

Specific aspects of the invention will now be described in more detail.

PorB Peptide Compositions

In one aspect, the present invention provides compositions and methods for production of anti-*chlamydial* antibodies by administration of a PorB peptide composition. In one embodiment, the compositions and methods of the invention are formulated as an immunogenic composition, and administered to induce an immune response to infection by *Chlamydia*. Antigenic and immunogenic PorB peptides of the invention include, but are not necessarily limited to, peptides comprising a neutralizing epitope. Where the immunogenic composition comprises an antigenic PorB peptide, the composition can further comprise any of a variety of acceptable adjuvants, or the peptide can be coupled to a carrier.

"Polypeptides" and "peptides", which are used interchangeably herein, are defined herein as organic compounds comprising two or more amino acids covalently joined by an amide bond. Peptides may be referred to with respect to the number of constituent amino acids, e.g., a dipeptide contains two amino acid residues, a tripeptide contains three, etc. In general, the peptides described herein do not encompass the full-length PorB polypeptide, and can be about 4, 6, 10 20, 30, 40, 50, 60 or more amino acids in length, with peptides of from about 4 to about 47, from about 6 to about 34, and from about 6 to about 20 amino acids being of particular interest. In one embodiment, the PorB polypeptide comprises at least one neutralizing epitope and is at least about 10 amino acid residues, usually at least about 15 or 20 amino acid residues in length.

The peptides of the invention, while described herein as being composed of naturally occurring, L-amino acids, are not limited to such. The peptides described herein may be modified at the amino and/or carboxy termini; modified to contain the D-isomer rather than the normal L-isomer;

modified chemically to have different substituents or additional moieties; and the like, with the proviso that these modifications do not eliminate or otherwise adversely affect the peptides ability to present a functional PorB epitope, particularly a neutralizing epitope of PorB. Exemplary chemical modifications of the peptides include acylation, alkylation, esterification, amidification, etc. to produce structural analogs.

Furthermore, the peptides described herein can be modified by amino acid insertion, deletion, addition, or substitution, again with the proviso that the modified peptide exhibits a PorB neutralizing epitope function. The amino acid substitutions may be of a conserved or non-conserved nature. Conserved amino acid substitutions involve replacing one or more amino acids of the peptide sequences described herein with amino acids of similar charge, size, and/or hydrophobicity characteristics, such as, for example, a glutamic acid (E) to aspartic acid (D) amino acid substitution. Non-conserved substitutions involve replacing one or more amino acids with amino acids possessing dissimilar charge, size, and/or hydrophobicity characteristics, such as, for example, a glutamic acid (E) to valine (V) substitution. Amino acid additions include additions to the N-terminus, the C-terminus and/or a region between the N- and C-terminus. PorB peptides can also be provided as a fusion protein with a non-PorB amino acid sequence.

The peptides of the invention may be prepared by recombinant or chemical synthetic methods, which techniques are well known in the art. See, for example, Creighton, 1983, Proteins: Structures and Molecular Principles, W. H. Freeman and Co., N.Y., which is incorporated herein by reference in its entirety. Short peptides, for example, can be synthesized on a solid support or in solution. Longer peptides may be made using recombinant DNA techniques. Here, the nucleotide sequences encoding the peptides of the invention may be synthesized, and/or cloned, and expressed according to techniques well known to those of ordinary skill in the art. See, for example, Sambrook, et al., 1989, Molecular Cloning, A Laboratory Manual, Vols. 1-3, Cold Spring Harbor Press, N.Y.

When administered to a host, the PorB peptides of the invention comprising at least one neutralizing epitope and sufficient to elicit a protective immune response) of PorB elicit an immune response (e.g., a protective or therapeutic immune response). Polypeptides of the invention include, but are not necessarily limited to, native PorB polypeptide fragments (e.g., immunogenic, immunoprotective fragment thereof, (e.g., a fragment of a PorB polypeptide comprising a neutralizing domain that, upon administration to a host, can elicit an immune response, preferably an immunoprotective immune response)), a recombinant form of a PorB peptide (e.g., a product of expression in a prokaryotic or eukaryotic recombinant host cell), a synthetically produced PorB peptide, a modified recombinant or synthetic PorB peptide (e.g, PorB neutralizing epitope peptide provided as a fusion protein), a PorB peptide variant or analog that retains antigenicity or immunogenicity of native PorB fragments having a neutralizing domain (e.g., an immunogenically similar or identical PorB-derived amino acid sequence), and the like. PorB peptides of interest are generally from at least about 4 amino acids to about fragments of about 60 amino acids, usually at least about 6 amino acids, more usually at least about 10 amino acids, and generally at least about 15 to 50 amino acids. Preferably, the PorB polypeptides have an amino acid sequence that provides for at least one neutralizing epitope domain. PorB peptides can comprise an amino acid sequence of a PorB polypeptide of C. trachomatis, C. pneumoniae or C. psittaci, preferably of C. trachomatis.

A composition of interest comprises, in one embodiment, a PorB peptide of C. trachomatis, C. pneumoniae or C. psittaci, preferably a PorB peptide of C. trachomatis. In one embodiment the C. trachomatis polypeptide comprises an amino acid sequence of an immunogenic fragment from at least one of four PorB neutralizing epitope domains, ND1, ND2, ND3 and ND4. The composition can comprise any combination of polypeptides having at least one of these PorB neutralizing epitope domains, and may comprise at least 2, 4, 6, 8, 9, 10 or more peptides. Generally at least two of the PorB neutralizing epitope domains are present in the composition, more usually at least three, and in some embodiments all four epitope domains are present. Table 1 provides the amino acid sequence for exemplary four neutralizing epitope domains of PorB C. trachomatis, and also identifies the amino acid residues which generally define each neutralizing domain.

TABLE 1

C. trachomatis PorB Neturalizing domains (ND)

| | |
|---|---|
| ND1 = Phe$_{34}$-Leu$_{59}$ | FPVIPGINIEQKNACSFDLCNSYDVL (SEQ ID NO:7) |
| ND2 = Asp$_{112}$-Glu$_{14}$ | DLVNCNLNTNCVAVAFSLPDRSLSAIPLFDVSFE (SEQ ID NO:8) |
| ND3 = Gly$_{179}$-Ala$_{225}$ | GMIEVQSNYGFVWDVSLKKVIWKDGVSFVGVGADYR HASCPIDYIIA (SEQ ID NO:9) |
| ND4 = Val$_{261}$-Asn$_{305}$ | VLPYLAFSIGSVSRQAPDDSFKKLEDRFTNLKFKVRK ITSSHRGN (SEQ ID NO:10) |

In certain embodiments, the immunogenic composition comprises multiple PorB peptides each having at least one different neutralizing epitope domain. In one example, the composition comprises a PorB peptide having an ND1 sequence or an antigenic or immunogenic portion thereof and a polypeptide having a ND2 sequence or an antigenic or immunogenic portion thereof. In other embodiments, the composition comprises peptides having amino acid sequences, or antigenic or immunogenic portions thereof, of each of the four neutralizing epitope domains (ND1, ND2, ND3 and ND4) or any combination thereof.

Peptides having neutralizing domains of particular interest include, but are not necessarily limited to, peptides B1-2 (SEQ ID NO. 11), B1-3 (SEQ ID NO. 12) of neutralizing domain 1 (ND1); polypeptides B2-3 (SEQ ID NO. 13), B2-4 (SEQ ID NO. 14) of ND2; polypeptides B3-2 (SEQ ID NO. 15), B3-3 (SEQ ID NO. 16), B3-4 (SEQ ID NO. 17) of ND3 and polypeptides B4-4 (SEQ ID NO. 18), B5-1 (SEQ ID NO. 19) and B5-2 (SEQ ID NO. 20) of ND4. These exemplary peptides, as well as other peptides, are further described in TABLE 2 and the Examples below.

In certain embodiments, the immunogenic composition of the invention comprises a combination of immunogenic or antigenic PorB polypeptides. For example, the composition can comprise a polypeptide of any of B1-2, B1-3, B2-3, B2-4, B3-2, B3-4 and B5-2 and any combination thereof. For example, the composition can comprise any combination of at least 2, 4, 6, 8, 9, 10 or more of these exemplary polypeptides. Furthermore, polypeptides comprising overlapping amino acid residues between polypeptides having SEQ ID NOs. 11-20 are also useful in the compositions of the present invention.

A PorB polypeptide having a neutralizing epitope can be delivered to the host in a variety of ways. For example, PorB peptides according to the invention can be provided and administered as an isolated or substantially purified protein preparation. Alternatively or in addition, the PorB peptides can be administered in the form of nucleic acid (e.g., RNA or DNA, usually DNA) encoding one or more, usually at least 2, 4, 6, 8, 9, 10 or more, PorB peptides having at least one neutralizing epitope (e.g., by genetic immunization techniques known in the art), by delivery of shuttle vector (e.g., a viral vector (e.g., a recombinant adenoviral vector), or a recombinant bacterial vector (e.g., a live, attenuated heterologous bacterial strain, e.g., live, attenuated *Salmonella*) that provides for delivery of PorB polypeptide-encoding nucleic acid for expression in a host cell. Where nucleic acid encoding a PorB polypeptide is used in the immunogenic composition, the nucleic acid (e.g., DNA or RNA) can be operably linked to a promoter for expression in a cell of the subject. Where two or more PorB peptides are administered in the form of PorB-encoding nucleic acid, the PorB peptides can be encoded on the same or different nucleic acid molecules.

Formulations

The PorB peptide compositions of the invention can be formulated in a variety of ways. In general, the compositions of the invention are formulated according to methods well known in the art using suitable pharmaceutical carrier(s) and/or vehicle(s). An exemplary suitable vehicle is sterile saline. Other aqueous and non-aqueous isotonic sterile injection solutions and aqueous and non-aqueous sterile suspensions known to be pharmaceutically acceptable carriers and well known to those of skill in the art may be employed for this purpose.

Optionally, a composition of the invention may be formulated to contain other components, including, e.g., adjuvants, stabilizers, pH adjusters, preservatives and the like. Such components are well known to those of skill in the art.

The compositions can be administered in any suitable form that provides for administration of the PorB peptides in an amount sufficient to elicit an immune response (e.g., humoral response, cellular response, and the like). For example, the composition can be administered as a liquid formulation or as a slow-release formulation (e.g., in a suitable solid (e.g., biodegradable) or semi-solid (e.g., gel) matrix that provides for release of the PorB peptide or PorB peptide-encoding nucleic acid over time). The composition can be administered in a single bolus, can be administered in incremental amounts over time, or any suitable combination. In addition, it may be desirable to administer one or more booster doses of the PorB peptides, which boosters may contain the same or different amounts of PorB peptide (or PorB peptide-encoding nucleic acid).

Administration of PorB Peptide Compositions

The PorB polypeptide immunogenic composition is administered in an "effective amount," that is, an amount of PorB polypeptide or PorB polypeptide-encoding nucleic acid that is effective in a route of administration to elicit a desired immune response, e.g., to elicit anti-PorB antibodies, e.g., to elicit anti-PorB antibody production and/or to elicit an immune response effective to facilitate protection of the host against infection by *Chlamydia*. For example, where PorB polypeptide is delivered using a nucleic acid construct or a recombinant virus, the nucleic acid construct or recombinant virus is administered in an amount effective for expression of sufficient levels of the selected gene product to elicit production of anti-PorB antibodies, and/or to provide a vaccinal benefit, e.g., protective immunity.

Conventional and pharmaceutically acceptable routes of administration include intranasal, intramuscular, intratracheal, subcutaneous, transdermal, subdermal, intradermal, topical, rectal, oral and other parental routes of administration. Routes of administration may be combined, if desired, or adjusted depending upon the immunogen or the disease. As noted above, the PorB composition of the invention can be administered in a single dose or in multiple doses, and may encompass administration of booster doses, to elicit antibodies and/or maintain immunity. Methods and devices for accomplishing delivery are well known in the art. For example for administration through the skin, any of a variety of transdermal patches can be used to accomplish delivery.

The amount of PorB polypeptide, PorB polypeptide-encoding nucleic acid, or PorB polypeptide recombinant virions in each dose is selected as an amount which induces an immune response (particular an immunoprotective immune response) without significant, adverse side effects. Such amount will vary depending upon which specific immunogen is employed, whether or not the immunogenic composition is adjuvanted, and a variety of host-dependent factors. Where PorB neutralizing epitope polypeptide is delivered directly, it is expected that each does will comprise 1-1000 µg of protein, generally from about 1-200 µg, normally from about 10-100 µg. An effective dose of a PorB nucleic acid-based immunogenic composition will generally involve administration of from about 1-1000 µg of nucleic acid. An optimal amount for a particular immunogenic composition can be ascertained by standard studies involving observation of antibody titres and other responses in subjects. Where the immunogenic composition is administered as a prophylactic or therapeutic vaccine, the levels of immunity provided can be monitored to determine the need, if any, for boosters. Following an assessment of antibody titers in the serum, optional booster immunizations may be desired. The immune response to the protein of this invention is enhanced by the use of adjuvant and or an immunostimulant.

Subjects

Using the methods and compositions described herein in connection with the subject invention, an immune response, including but not limited to an immunoprotective response, against *chlamydial* infection can be induced in any subject, human or non-human. In one embodiment, the subject to receive the PorB composition of the invention is one that is susceptible to infection by a *chlamydial* strain, particularly a *chlamydial* strain pathogenic for the subject species. In general, the methods of the invention are effective to elicit an anti-*chlamydial* immune response, with production of anti-PorB antibodies, particularly antibodies that are cross-reactive with two or more *chlamydial* species being of particular interest. In one embodiment, the PorB composition of the invention is administered to as to facilitate prevention or inhibition of infection of the subject by a *Chlamydia* species that expresses on its surface a protein that is immunocrossreactive with PorB. In one embodiment administration of a PorB neutralizing epitope polypeptide of *C. trachomatis* induces an immune response against *C. trachomatis, C. pneumoniae* and *C. psittaci*, particularly an immune response against *C. trachomatis*. In another embodiment administration of a PorB neutralizing epitope polypeptide of *C. pneumoniae* induces an immune response against *C. trachomatis, C. pneumoniae* and *C. psittaci*, and particularly an immune response against *C. pneumoniae*. In another embodiment, administration of a PorB neutralizing epitope polypeptide of *C. psittaci* induces an immune response against infection by *C. trachomatis, C. pneumoniae* and *C. psittaci*, and particularly an immune response against *C. psittaci*.

Human disease associated with *chlamydial* infection that can be mitigated or prevented using the methods and compositions described herein include, but are not necessarily limited to, sexually transmitted disease (urethritis and epidiymitis in men; pelvic inflammatory disease in women), conjunctivitis, and pneumonia. Of particular interest is the inhibition or prevention of infection by *C. trachomatis*, by *C. pneumonia*, and by *C. psittaci*. Exemplary *chlamydial* diseases are described in more detail below.

*C. trachomatis*, the most common cause of sexually transmitted diseases in the United States, causes a variety of diseases including nongonococcal urethritis and epididymitis in men; cervicitis, urethritis, and pelvic inflammatory disease in women; Reiter's syndrome; and neonatal conjunctivitis and pneumonia, the latter of which are generally acquired through maternal transmission. *C. trachomatis* has been implicated in 20% of adults with pharyngitis. Several immunotypes of *C. trachomatis* can cause lymphogranuloma venereum (LGV), a disease found mostly in tropical and subtropical areas. LGV strains invade and reproduce in regional lymph nodes.

*C. pneumoniae* (previously called Taiwan acute respiratory agent or TWAR), originally considered a serotype of *C. psittaci*, can cause pneumonia, especially in children and young adults. The organism has been found in atheromatous lesions, and infection is associated with increased risk of coronary artery disease.

*C. psittaci* infects many animals, but human infection is closely related to contact with birds. In humans, *C. psittaci* causes psittacosis, an infectious atypical pneumonia transmitted to humans by certain birds. In humans, psittacosis (ornithosis, parrot fever) is usually caused by inhaling dust from feathers or excreta of infected birds or by being bitten by an infected bird; rarely, it occurs by inhaling cough droplets of infected patients or venereally. Human-to-human transmission may be associated with highly virulent avian strains.

Where the subject is non-human, subjects of particular interest include rodent (e.g., mouse, rat, guinea pig, and the like), ungulate (e.g., bovine, goat, sheep, and the like), feline, and avian subjects.

Anti-PorB Antibodies

Antibodies that specifically bind a PorB polypeptide having a neutralizing epitope can be used to isolate PorB polypeptides—either full-length or partial peptides—or one or more *chlamydial* species. Anti-PorB antibodies can also be administered to provide temporary, passive immunity against *chlamydial* infections (e.g., to inhibit *chlamydial* infection and/or disease symptoms that can result from such infection). Methods for production of anti-PorB antibodies (e.g., monoclonal or polyclonal antibodies) are well known in the art, as are methods for formulating such antibodies for administration. In one embodiment the anti-PorB antibody is a humanized antibody. Anti-PorB antibodies of interest also encompass modified antibodies (e.g., modified to increase biological half-life following administration).

Methods for use of anti-PorB antibodies for isolation of PorB polypeptides are well known in the art. For example, the anti-PorB antibody can be used to immunoprecipitate PorB peptides and polypeptides in solution. Alternatively, the anti-PorB antibody can be bound to a solid support, such as an affinity column or a well of a microtiter plate, to facilitate immunopurification. Exemplary methods for PorB polypeptide and peptide isolation and/or purification are provided below in the context of diagnostic assays, and can be readily adapted to increase the yield of PorB In therapeutic applications, anti-PorB antibodies are administered in an amount sufficient to neutralize *Chlamydia* so as to prevent, mitigate, or reduce the likelihood of onset of infection. Anti-PorB antibodies can be administered by any suitable route, generally by parenteral injection (e.g., subcutaneous, intramuscular, intravenous, etc.). Administration of anti-PorB antibodies particularly useful for preventing or inhibiting infection in immunocompromised subjects or other subjects having an immune system that can not maintain an effective, immunoprotective response to, for example, a PorB antigen.

Antibodies that bind PorB of two or more *Chlamydial* species are of particular interest, particularly antibodies that bind-PorB epitopes in a manner effective to block infection by each of these species are of particular interest. For example, antibodies that bind PorB of *C. trachomatis* as well as PorB of *C. pneumoniae* and/or *C. psittaci*, can be used to provide passive immunity that protects against infection by each of these *chlamydial* species.

Diagnosis of *Chlamydial* Infection

In addition to the uses described above, PorB peptides having a neutralizing epitope and sequences obtained from PorB-encoding polynucleotides can be used in the detection of *Chlamydia* infection in a subject and/or determining whether a subject has been exposed to *Chlamydia* infection. Diagnostic assays based upon detection of PorB or a PorB-encoding sequence in a biological sample include, but are not necessarily limited to, detection of PorB peptides, detection of anti-PorB antibodies, and/or detection of PorB peptide-encoding sequences in a test sample from the subject. Detection of any of these PorB peptide, polynucleotides, or antibodies in a sample taken from a subject is indicative of *chlamydial* infection in the subject. For clarity, applicants note that "probe" as used herein in the context of detection of PorB polypeptides or PorB polypeptide-encoding polynucleotides is meant to encompass anti-PorB antibodies (e.g., for detection of PorB polypeptide), PorB polypeptide or PorB peptides (e.g., for detection of anti-PorB antibodies), and PorB polynucleotides and fragments thereof (e.g., for use in hybridization or PCR assays to detect PorB polynucleotides).

In one general embodiment, the methods of the invention involves detecting PorB peptides or anti-PorB antibodies in the subject by contacting an appropriate biological test sample from a subject suspected having been exposed to *Chlamydia* or suspected of having a *Chlamydia* infection with a probe that is one of a) an antibody that specifically binds a PorB polypeptide, b)a PorB polypeptide. After the test sample is contacted with the probe for a time sufficient to allow for formation of specific antibody-PorB polypeptide binding pairs, the formation of such binding pairs is detected. Detection of the antibody-PorB binding pairs indicates that the subject has been exposed to *Chlamydia* (due to the presence of PorB polypeptides in the sample where the probe is an anti-PorB antibody), or has mounted an immune response to PorB polypeptide (due to the presence of anti-PorB antibodies in the sample, as detected using a PorB polypeptide probe) which suggests at least prior exposure to *Chlamydia*. In one embodiment of particular interest, the probe is a PorB peptide comprising at least one neutralizing domain, which is used to detect to isolate anti-PorB antibodies.

In another general embodiment, the presence of a *Chlamydia* infection in the host is detected using an probe to specifically hybridizes to and/or specifically amplifies (e.g., through use of PCR) to a PorB polypeptide encoding polynucleotide. Detection of hybridization or detection of a specific PCR product indicates that the subject has a *Chlamydia* infection.

Diagnosis Based on Detection of PorB Polypeptides and/or Anti-PorB Antibodies

Detection of PorB polypeptides can be accomplished according to a wide variety of immunoassays that are well known in the art, and may be performed either qualitatively or quantitatively. For example, the diagnostic assay can measure the reactivity between an anti-PorB antibody (e.g., a polyclonal or monoclonal antibody (MAb), preferably a MAb) and a patient sample, usually a sample of a bodily fluid, e.g., mucosal secretion, blood-derived sample (e.g., plasma or serum), urine, and the like. The patient sample may be used directly, or diluted as appropriate, usually about 1:10 and usually not more than about 1:10,000. Immunoassays may be performed in any physiological buffer, e.g. PBS, normal saline, HBSS, PBS, etc.

In one embodiment, a conventional sandwich type assay is used. A sandwich assay is performed by first immobilizing proteins from the test sample on an insoluble surface or support. The test sample may be bound to the surface by any convenient means, depending upon the nature of the surface, either directly or indirectly. The particular manner of binding is not crucial so long as it is compatible with the reagents and overall methods of the invention. They may be bound to the plates covalently or non-covalently, preferably non-covalently.

The insoluble supports may be any compositions to which the test sample polypeptides can be bound, which is readily separated from soluble material, and which is otherwise compatible with the overall method of detecting and/or measuring type I cell- or type II cell-specific polypeptide. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Before adding patient samples or fractions thereof, the non-specific binding sites on the insoluble support, i.e. those not occupied by polypeptide, are generally blocked. Preferred blocking agents include non-interfering proteins such as bovine serum albumin, casein, gelatin, and the like. Alternatively, several detergents at non-interfering concentrations, such as Tween, NP40, TX100, and the like may be used.

Samples, fractions or aliquots thereof can be added to separately assayable supports (for example, separate wells of a microtiter plate). A series of standards, containing known concentrations of PorB can be assayed in parallel with the samples or aliquots thereof to serve as controls and to provide a means for quantitating the amounts of PorB polypeptide present in the test sample. Preferably, each sample and standard will be added to multiple wells so that mean values can be obtained for each.

After the test sample polypeptides are immobilized on the solid support, anti-PorB antibody is added. The incubation time of the sample and the antibody should be for at time sufficient for antibody binding to the insoluble polypeptide. Generally, from about 0.1 to 3 hr is sufficient, usually 1 hr sufficing.

After incubation, the insoluble support is generally washed of non-bound components. Generally, a dilute non-ionic detergent medium at an appropriate pH, generally 7-8, is used as a wash medium. From one to six washes may be employed, with sufficient volume to thoroughly wash non-specifically bound proteins present in the sample. After washing, antibody binding to the sample can be detected by virtue of a detectable label on the antibody. Where the antibody is not detectably labeled, antibody binding can be detected by contacting the sample with a solution containing antibody-specific second receptor, in most cases a secondary antibody (i.e., an anti-antibody). The second receptor may be any compound which binds antibodies with sufficient specificity such that the bound antibody is distinguished from other components present. In a preferred embodiment, second receptors are antibodies specific for the anti-PorB antibody, and may be either monoclonal or polyclonal sera, e.g. goat anti-mouse antibody, rabbit anti-mouse antibody, etc.

The antibody-specific second receptors are preferably labeled to facilitate direct, or indirect quantification of binding. Examples of labels which permit direct measurement of second receptor binding include light-detectable labels, radiolabels (such as $^3$H or $^{125}$I), fluorescers, dyes, beads, chemiluminescers, colloidal particles, and the like. Examples of labels which permit indirect measurement of binding include enzymes where the substrate may provide for a colored or fluorescent product. In a preferred embodiment, the second receptors are antibodies labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

Alternatively, the second receptor may be unlabeled. In this case, a labeled second receptor-specific compound is employed which binds to the bound second receptor. Such a second receptor-specific compound can be labeled in any of the above manners. It is possible to select such compounds such that multiple compounds bind each molecule of bound second receptor. Examples of second receptor/second receptor-specific molecule pairs include antibody/anti-antibody and avidin (or streptavidin)/biotin. Since the resultant signal is thus amplified, this technique may be advantageous where only a small amount of PorB polypeptide is present, or where the background measurement (e.g., non-specific binding) is unacceptably high. An example is the use of a labeled antibody specific to the second receptor. More specifically, where the second receptor is a rabbit anti-allotypic antibody, an antibody directed against the constant region of rabbit antibodies provides a suitable second receptor specific molecule. The anti-Ig will usually come from any source other than human, such as ovine, rodentia, particularly mouse, or bovine.

The volume, composition and concentration of anti-anti-body solution provides for measurable binding to the antibody already bound to receptor. The concentration will generally be sufficient to saturate all antibody potentially bound to PorB polypeptide. The solution containing the second receptor is generally buffered in the range of about pH 6.5-9.5. The solution may also contain an innocuous protein as previously described. The incubation time should be sufficient for the labeled ligand to bind available molecules. Generally, from about 0.1 to 3 hr is sufficient, usually 1 hr sufficing.

After the second receptor or second receptor-conjugate has bound, the insoluble support is generally again washed free of non-specifically bound second receptor, essentially as described for prior washes. After non-specifically bound material has been cleared, the signal produced by the bound conjugate is detected by conventional means. Where an enzyme conjugate is used, an appropriate enzyme substrate is provided so a detectable product is formed. More specifically, where a peroxidase is the selected enzyme conjugate, a preferred substrate combination is $H_2O_2$ and is O-phenylenediamine which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art. For the product of the substrate O-phenylenediamine for example, light absorbance at 490-495 nm is conveniently measured with a spectrophotometer.

The absence or presence of antibody binding may be determined by various methods that are compatible with the detectable label used, e.g., microscopy, radiography, scintillation counting, etc. Generally the amount of bound anti-PorB antibody detected will be compared to control samples (e.g., positive controls containing PorB or negative controls lacking such polypeptides). The presence of anti-PorB antibody is indicative of the presence of a *Chlamydia* in the test sample, which in turn is indicative of *chlamydial* infection in the subject.

As will be readily appreciated by the ordinarily skilled artisan upon reading the present disclosure, the above techniques can be readily modified to provide for detection of anti-PorB antibodies in the host. For example, rather than immobilizing PorB polypeptide on a solid support, an anti-PorB antibody is immobilized on the support and subsequently contacted with a test sample from the host. Binding of PorB polypeptide from the test sample to the support-bound anti-PorB antibody can then be detected using a second anti-PorB antibody (e.g., that binds to a different epitope of the polypeptide than the bound antibody). Binding of the second antibody can then be detected according to methods well known in the art.

Diagnosis Based on Detection of PorB Nucleic Acid

Where the diagnostic assay involves detection of a PorB-encoding sequence, the assay can take advantage of any of a variety of polynucleotide detection techniques that are well known in the art. For example, a fragment of a PorB-encoding sequence can be used as a probe to detect hybridizing sequences in a test sample, or for use as a primer in PCR amplification of *chlamydial* nucleic acid in at test sample. Methods for detecting sequences based on hybridization, as well as use of PCR are known in the art, see, e.g., Sambrook, et al. Molecular Cloning: A Laboratory Manual, CSH Press 1989. The probe or primer may comprise a detectable label. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the polynucleotide is conjugated to biotin, haptens, etc. having a high affinity binding partner, e.g. avidin, specific antibodies, etc., where the binding partner is conjugated to a detectable label. In PCR, the label may be conjugated to one or both of the primers; alternatively, the pool of nucleotides used in the amplification is labeled, so as to incorporate the label into the amplification product.

Kits for Detection of *Chlamydia*

PorB peptides (for detection of specific antibodies), anti-PorB antibodies, and PorB peptide-encoding polynucleotide probes and/or primers, as well as other materials useful in the diagnostic methods of the invention (e.g., labels, compounds for detection of labels, solid supports for capture of nucleic acid in a sample, filters for at least partial separation or purification of parasites in the sample, detergents and other reagents (e.g., lysing mammalian and cells in the sample), etc.) can be provided in a kit. Such kits can include samples to serve as positive controls or negative controls. Preferably such kits are designed for use in the field, e.g., do not contain components that require refrigeration, are portable, etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials for Examples 1-12

The following procedures are used in the Examples described in detail below. Although some of the methods described below are in common use, the specific protocol used in the Examples below is described in detail where alternative protocols are often employed. Basic procedures such as DNA digestion by restriction enzymes and ligation are not described, as such are well within the skill of the ordinarily skilled artisan and, in some instances, are carried out according to the enzyme or kit manufacturer's instructions.

*Chlamydial* cultures. *C. trachomatis* strains B/TW-5/OT, C/TW-3/OT, and L2/434/Bu were grown in L929 cells, and strain D/UW-3/Cx was grown in HeLa 229 cells. Elementary bodies (EB) and reticulate bodies (RB) were separately purified by diatrizoate (Renograffin; E. R. Squibb and Sons, Princeton, N.J.) gradients and were used immediately after purification or stored at −70 C. RB was purified at 24 hours post-infection.

Bacterial strains and plasmid. The synthetic gene encoding MOMP (ompA) was constructed in *E. coli* HMS 174 (DE3) and has been previously described (Jones et al. (2000) *Gene* 258:173-181). *E. coli* HMS 174 (DE3) without the plasmid was used as a control strain. PorB cloning and expression were done in the *E. coli* strain, TOP10 (Invitrogen, Carlsbad, Calif.). The complete PorB gene was cloned into the pBAD-TOPO TA vector (Invitrogen), which contains the araBAD promoter.

Expression and purification of PorB. Regulation of expression is by the AraC gene product on the promoter in the absence or presence of arabinose. All *E. coli* cultures were grown with aeration at 37° C. in Luria-Bertani broth containing 100 mg/ml of ampicillin until the cultures reached an O.D of 0.6. 0.02% Arabinose to a final concentration of 0.5 mM was added to induce the expression of PorB. PorB was cloned with a C-terminal HIS tag and purified by nickel column using the HIS Bind Purification system (Novagen, Madison, Wis.). Extraction of PorB with 1% octylglucoside at 37° C. for 1 h and dialysis of the detergent out of the extracted PorB using PBS and then 1× Bind buffer (Novagen) was necessary before purification by nickel column. IPTG was added to a final concentration of 0.5 mM to induce the expression of MOMP. The outer membranes of *E. coli* expressing MOMP were purified as described in MOMP Jones et al. (2000 *Gene* 258:173-181)

Outer membrane preparation. The spheroplasts and outer membranes of *E. coli* were isolated using the method of Osborn and Munson (1974 *Methods Enzymol.* 31:642-653) with the following modifications. The *E. coli* were grown in Luria Bertani broth with 100 mg/ml ampicillin at 37° C. with vigorous aeration to a density of approximately $5\times10^8$ bacteria/ml, followed by 2 hours of induction by addition of 0.02% arabinose to a concentration of 0.5 mM. 25 ml aliquots of the spheroplasts were lysed by sonication by immersing in an ice-salt bath and sonicating for three 15-second periods with a Braunsonic U sonicator. The suspension was cooled for 1 minute between bursts. The unbroken cells were removed by centrifugation at 1200×g for 15 minutes at 4° C. The supernatant fraction was then centrifuged for 2 hours at 100,000×g at 4° C. The membrane pellet was resuspended in a small volume of cold 0.25 M sucrose-3.3 mM Tris-1 mM EDTA, pH 7.8 and centrifuged for 2 hours at 100,000×g 4° C. The pellet was then suspended in 6 ml of cold 25% sucrose –5 mM EDTA, pH 7.5 for separation by isopycnic centrifugation. An outer membrane preparation was performed with a control clone expressing a non-outer membrane protein and this protein was not detected in the outer membrane fraction.

*Chlamydial* outer membrane complex (COMC) preparation. The COMC was prepared from fresh, not previously frozen, purified EB (10 mg) and performed according to the method of Caldwell et al. (Caldwell et al. (1981) *Infect. Immun.* 31:1161-1176) with some modifications. EB were suspended in 3 ml of 10 mM sodium phosphate buffer (pH 7.4) and 2% SARKOSYL. This suspension was sonicated briefly and centrifuged at 100,000×g for 1 hour at 20° C. Both the soluble and insoluble (COMC) fractions were analyzed by SDS-PAGE.

Antibodies. Polyvalent monospecific antisera to PorB were obtained from mice Swiss-Webster mice immunized with 1) nickel column-purified PorB protein and 2) a piece of PorB consisting of the amino-terminal portion, from amino acid 24-71 (PorB$^{24-71}$). The mice were immunized twice at two-week intervals with 100 μg of purified protein in an equal volume of complete Freund's adjuvant for the second immunization. IH5 is a L2 serovar specific monoclonal antibody specific to MOMP. Polyvalent antiserum produced in rabbits using L2 EB and polyvalent monospecific antiserum produced in rabbits using cloned and expressed 28 kDa plasmid protein (pgp3) (Comanducci et al. (1993) *J. Gen. Microbiol.* 139:1083-1092) were used in the dot blot experiment.

Cell staining. *C. trachomatis* serovar L2-infected, D-infected and uninfected HeLa cells were fixed in methanol for 10 minutes and washed three times in PBS. The anti-PorB monospecific antibody was diluted 1:200, added to the cells and incubated for 1 hour at room temperature on a rocker platform. The monolayer was rinsed three times in PBS and overlaid with a fluorescein isothiocyanate-conjugated anti-mouse immunoglobulin G (Zymed, So. San Francisco, Calif.) diluted 1:50. The cells were incubated in the dark for one hour at room temperature on a rocker platform and then washed three times with PBS. The cells were then counter stained with Evans blue and observed by fluorescence microscopy.

Dot Blot assay. Dot blots were performed as previously described by Zhang et al., (1987 *J. Immunol.* 138:575-581) with the following differences: 1) the method of detection was enhanced chemiluminescence (ECL) (Amersham Pharmacia Biotech, Piscataway, N.J.); 2) an anti-mouse HRP-conjugated secondary antibody was used; 3) the primary and secondary antibodies were washed by rinsing the wells with PBS and discarding the PBS. Vacuum filtration was used after the final wash to remove all liquid from the wells.

Dot blots of viable *chlamydial* EB to determine surface accessibility of PorB were performed by probing immobilized EB with (1) a negative control antibody, anti-pgp3; (2) a positive control monoclonal, IH5; (3) an anti-PorB antibody; (4) an anti-PorB$^{24-71}$ antibody; and (5) a positive control polyclonal, anti-L2 EB was used. The anti-pgp3 antibody was used at 1:1000 for the immunoblot and bound a 28 kDa protein, while it was used at 1:100 for the dot blot. The rabbit anti-L2 EB polyclonal antibody was used at 1:1000 for both the immunoblot and dot blot. The IH5 monoclonal antibody was used at 1:1000 for the immunoblot and at 1:4000 for the dot blot. The anti-PorB antibody was used at 1:200 for the immunoblot and at 1:100 for the dot blot.

Protease cleavage. Fresh EB, not previously frozen, were incubated with various concentrations of trypsin (0, 0.001, 0.01, 0.1 mg/ml) and proteinase K (0, 0.1, 0.5, 1 mg/ml) for 30 minutes at 37° C. The treated EB were then immediately transferred to a nitrocellulose membrane and a dot blot analysis was performed as describe above.

Neutralization assay. The HaK (hamster kidney cells) in vitro neutralization assay was performed as previously described (Byrne et al. (1993) *J. Infect. Dis.* 168:415-20). Antibodies, except for pre-immune serum, were quantitated and diluted to 200 mg/ml, then serially diluted by two-fold to 12.5 mg/ml. Pre-immune serum was used at a dilution of 1:10 and serially diluted 2-fold to 1:160. For detection of PorB, monospecific anti-PorB was purified with protein A (Sigma, St. Louis, Mo.), filter sterilized, quantitated using the BCA assay (Pierce, Rockford, Ill.), and diluted in SPG to the appropriate concentrations. A control monoclonal antibody with specificity for MOMP (IH5) was used. Also, a control monoclonal antibody with unrelated specificity, the anti-pgp3 antibody as well as the pre-immune serum were used as controls. L2 EB was diluted in SPG to contain $2\times10^4$ IFU/ml, 100 ml was added to each antibody dilution in total volume of 200 ml. Neutralization proceeded for 30 minutes. IFU were quantitated by counting ten fields at a magnification of 40×. A mean IFU per field was calculated and the results were shown as percent reduction in mean IFU compared with the control plates.

Quantitation of protein. Purified protein and outer membranes for use in the liposome swelling assay was quantitated according to the Lowry method. All other samples were quantitated by the BCA assay (Pierce, Rockford, Ill.).

Liposome swelling assay. The liposome swelling assay was performed according to the method of Nikaido (Nikaido & Rosenberg (1983) *J. Bacteriol.* 153:241-252) with the following modifications: 1) liposomes were made by mixing 5.0 µmol phosphatidylcholine and 0.02 µmol dicetylphosphate with outer membrane proteins or purified protein in order to increase the optical density readings to the range of 0.4-0.7 O.D., and 2) the liposome drying time was longer than 2 minutes (i.e., 5 minutes), but at a lower temperature of 37° C. Liposomes were made with either dextran T-40 (15% dextran T-40 in 5 mM Tris-Cl, pH7.5) or stachyose inside. Since stachyose is impermeable to the porins, it was used as a control to determine the isoosmotic concentration of other solutes. The concentration of stachyose which produced no swelling or shrinking of the proteoliposomes was determined to be the isoosmotic concentration. The swelling rates were determined as d(1/OD)/dt from the optical density changes between 10 and 20 seconds (Nikaido & Rosenberg (1983) *J. Bacteriol.* 153:241-252).

Liposome swelling assay for testing anions. Liposomes were made according to the method described above with a few modifications. The following was added to phosphatidylcholine and dicetylphosphate dried with PorB (6 µg): 4 mM NAD$^+$, 12 mM stachyose, 1 mM imidazole-NAD buffer pH (6.0). The test solution consisted of 1 mM Imidazole-NAD (pH 6.0), 1 mM Sodium NAD, 6 mM disodium salt of the anion to be tested (α-ketoglutarate, succinate, oxaloacetate, malate, or citrate). Control liposomes without protein were used to determine the isotonic concentration of the test solutions.

Enzyme-linked liposome swelling assay. Liposomes were made as described above with addition of 50 mM potassium phosphate, 2.5 mM NAD$^+$, 0.2 mM thiamin pyrophosphate, 1.0 mM magnesium chloride, 0.13 mM coenzyme A, 2.6 mM cysteine, and 5.0 units of α-ketoglutarate dehydrogenase. Various concentrations of α-ketoglutarate (0.001 mM-1 mM) were used as test solutes. Liposomes containing PorB (6 µg) and control liposome without protein were made with the reaction mixture, washed through a SEPHADEX column (S-300) equilibrated with reaction mixture without α-ketoglutarate dehydrogenase, and placed inside a cuvette. α-ketoglutarate was added to the reaction and mixed. The formation of NADH was measured by the increase in O.D.$_{340}$.

Example 1

Analysis of PorB Sequence—Comparison to Major Outer Membrane Protein (MOMP)

Genome sequence analysis revealed a number of predicted outer membrane proteins (see Stephens et al. 1998 "Genome sequence of an obligate intracellular pathogen of humans: *Chlamydia trachomatis*" *Science* 282:754-759). One such predicted outer membrane protein, encoded by the predicted open reading frame CT713, was selected for analysis, and referred to herein as PorB. The nucleotide and amino acid sequences of PorB (CT713) are available within the complete sequence of the genome at GenBank Accession No. NC_000117, with the amino acid sequence at GenBank Accession No. gi|3329169. The open reading frame corresponding to PorB is the complement of nucleotide residues 3616 to 4638 of GenBank Accession No. AE001342. The nucleotide and amino acid sequences of PorB of *C. trachomatis* are provided in the Sequence Listing as SEQ ID NOS:1 and 2, respectively. Alignment of the amino acid sequence of PorB with the amino acid sequence of MOMP is provided in FIG. 1.

Figure 2:
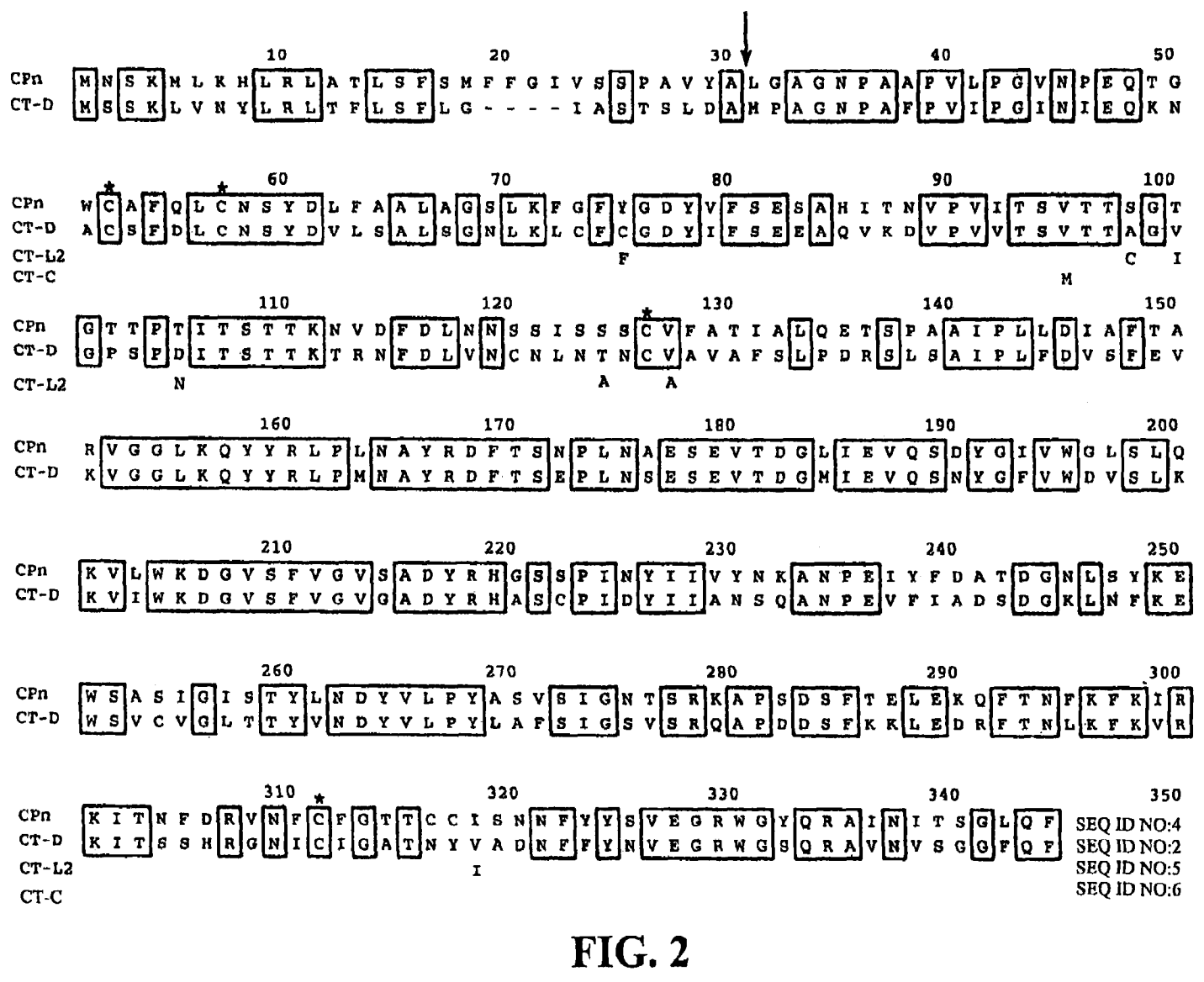

As illustrated in FIG. 1, PorB has only slight sequence similarity (20.4%) to MOMP. Despite this relatively low amino acid sequence similarity, PorB and MOMP do share certain characteristics and structural features. The estimated size of this protein is 38,000 daltons and the isoelectric point was calculated to be 4.9. MOMP has a molecular weight of 40,000 with an isoelectric point calculated and experimentally confirmed to be 5.0 (Bavoil et al. (1984) *Infect. Immun.* 44:479-485). PorB has a predicted cleavable leader sequence as well as an amino acid sequence which ends in phenylalanine (arrow in FIG. 2), a characteristic of many outer membrane protein (Struyvé et al. (1991) *J. Mol. Biol.* 218:141-148). Both PorB and MOMP have the same number of cysteines (9 cysteines) suggesting that PorB may be an outer membrane cysteine-rich protein analogous to, although distinct from, MOMP.

Previous reports on outer membrane proteins of *Chlamydia* have not identified this protein. The overabundance of MOMP and similarity in size and isoelectric point likely contributed in preventing earlier detection of PorB. PorB is not as predominant as MOMP by approximately 20-fold. Since PorB is similar in size to MOMP, an SDS-PAGE analysis of *chlamydial* outer membrane complexes can not distinguish PorB from MOMP. Also, PorB has a similar isoelectric point to MOMP, therefore a 2-D gel analysis may not separate the proteins (Bavoil et al. (1984) *Infect. Immun.* 44:479-485; Bini et al. (1996) *Electrophoresis* 17:185-190).

Example 2

Analysis of PorB Sequence—Comparison of PorB Amino Acid Sequences from Different Serovars When compared with other serovars of *C. trachomatis*, MOMP has four distinct variable segments which correspond to surface exposed regions of the protein. Serovar designations have been related to the differences in the variable segments of MOMP (Stephens et al. (1988) *J. Exp. Med.* 167:817-831). In order to determine whether this serovar variation is also characteristic for PorB, the sequence of PorB between serovars was compared.

FIG. 2 provides an alignment of the amino acid sequences of PorB from the *C. trachomatis* serovars D (CT-D) (SEQ ID NO:2), L2 (CT-L2) (SEQ ID NO:5), and C (CT-C) (SEQ ID NO:6), as well as the amino acid sequence of PorB from *C. pneumoniae* (CPn) (SEQ ID NO:4). The PorB of *C. trachomatis* and *C. pneumoniae* are 59.4% identical. *C. trachomatis* serovar L2 and C differences are indicated below the amino acid sequence. The cysteines are indicated with an asterisk above the amino acid sequence.

The nucleotide and amino acid sequence alignments between serovars D, B, C and L2 revealed no to only minor differences. There is no PorB sequence difference between serovars D and B, while there is one nucleotide difference, which results in an amino acid change, between serovars D (or B) and C. Between serovars D (or B) and L2 there are six nucleotide differences, each of which result in a difference in the encoded amino acid. The nucleotide differences occur throughout the gene and were not clustered to any region (FIG. 2). Among the serovars investigated, there are no variable segments in PorB such as there are in MOMP. Thus, sequence variation is not a phenotype for PorB.

Comparison between PorB of *C. trachomatis* (serovar D) and *C. pneumoniae* reveals greater differences dispersed throughout the gene. However, with 59.4% identity between amino acid sequences of *C. trachomatis* and *C. pneumoniae*, this protein is highly conserved between species (FIG. 2). *C. pneumoniae* PorB has 6 cysteines, four of which are conserved between species, while *C. trachomatis* serovars D, B and C have 9 conserved cysteines and serovar L2 has 8.

Example 3

Expression of PorB in *E. coli*

PorB was predicted to be in the outer membrane through a variety of protein localization programs such as PSORT (K. Nakai, Human Genome Center, Institute for Medical Science, University of Tokyo, Japan). A leader sequence cleavage site for *C. trachomatis* PorB was predicted to be at amino acid 26 (FIG. 2). The complete gene including the leader sequence was cloned into *E. coli* with a HIS tag at the C-terminal end of PorB and expressed. The protein was affinity purified by nickel column chromatography.

PorB expressed in *E. coli* was localized to the outer membrane fraction as determined by an immunoblot using an antibody to the C-terminal HIS tag. *E. coli* porins were also detected in this outer membrane fraction by Coomassie stain. The presence of PorB was primarily localized to the outer membrane suggesting that PorB has the necessary signal(s) to be transported to the outer membrane by *E. coli*.

Example 4

Presence of PorB in Inclusions

In order to characterize PorB in *Chlamydia*, a polyclonal monospecific serum was produced to the complete purified protein. FITC cell staining experiments using the anti-PorB serum showed that this serum contained antibody that bound antigens localized to the inclusions in infected cells. Anti-PorB serum did not label uninfected control cells. Staining cells infected with serovar L2 and serovar D, 48 and 72 hours post infection, respectively with anti-PorB serum revealed punctate staining consistent with the morphology for EB and RB. This antibody staining was present at 10, 15, 20, 24, 48 hours post infection, indicating that this protein is constitutively expressed and/or present throughout the *chlamydial* development cycle.

Example 5

Localization of PorB to the COMC

The anti-PorB antibody bound a protein in *Chlamydia* that was similar in size to MOMP by immunoblot analysis. The amount of PorB present in EB and RB was similar. The serum also bound the purified HIS-tagged protein, which was detected by an anti-HIS antibody. Although there were only slight similarities in sequence to MOMP, testing for cross reactivity between antibodies to PorB and MOMP was performed. Anti-PorB serum did not bind MOMP expressed in *E. coli*. Therefore, it is concluded that the anti-PorB sera bound PorB and did not cross react with MOMP.

In order to determine if PorB is a component of the *Chlamydia* Outer Membrane Complex (COMC), the COMC was isolated and probed with anti-PorB serum. Since the *chlamydial* outer membrane is highly disulfide bonded, the Sarkosyl insoluble fraction contains a number of proteins such as MOMP and other cysteine rich proteins. PorB was detected in the COMC fraction and not the soluble supernatant. Therefore, the presence of PorB in the COMC fraction demonstrates that this protein is in the *chlamydial* outer membrane and is disulfide linked perhaps to other COMC proteins.

Example 6

Surface Accessibility of PorB

Since PorB was predicted to be in the outer membrane and was localized to the COMC, surface accessibility of this protein was tested. Dot blot experiments have been shown to be specific for surface accessible antigens (Zhang et al. (1987) *J. Immunol.* 138:575-581) and was used to test surface accessibility of PorB. The dot blot using the anti-PorB sera showed that this antibody bound EB. A negative control rabbit polyclonal serum to a 28 kDa plasmid protein (pgp3) was used as a negative control antibody since this protein is not present in the outer membrane of *Chlamydia* (Comanducci et al. (1993) *J. Gen. Microbiol.* 139:1083-1092). This negative control antibody did not bind EB, while a positive control antibody to a surface accessible antigen on MOMP (IH5) bound. These data demonstrate that PorB is localized to the outer membrane.

Example 7

Effect of Proteolytic Cleavage on PorB

To investigate surface exposure of PorB, purified EB were digested with proteases and proteins from EB were assessed for binding by the anti-PorB antibody. Using the dot blot method, EB were treated with various concentrations of trypsin or proteinase K, immobilized on a nitrocellulose membrane and probed with the anti-PorB antibody, as well as to antibodies to MOMP and the anti-pgp3 antibody. A reduction in binding by anti-PorB antibodies was observed for EB-digested proteins suggesting that PorB has surface accessible trypsin and proteinase K cleavage sites, and thus is an outer membrane protein.

Example 8

Neutralization of *C. trachomatis* By Anti-PorB

Since PorB is an outer membrane protein with surface exposed regions, antibodies made to PorB were tested for ability neutralize infectivity of *C. trachomatis* (serovar L2). The anti-PorB sera produced using either the entire protein or an amino-terminal fragment (amino acids 24-71) at a concentration of 100 mg/ml neutralized infectivity by up to 88% and 70%, respectively, further supporting the conclusion that PorB is a surface exposed outer membrane protein (FIG. 3). The control antibody without specificity to outer membrane proteins, anti-pgp3, as well as the pre-immune sera did not neutralize infectivity (FIG. 3). A monoclonal antibody to serovar L2 MOMP (IH5) at a concentration of 50 and 100 mg/ml neutralized infectivity up to 78% (FIG. 3). This neutralization assay confirms that antibodies to PorB can inhibit infectivity by *C. trachomatis* since this assay is an art-recognized in vitro correlate for the assessment of protective immunity (Byrne et al. (1993) *J. Infect. Dis.* 168:415-20).

Example 9

Pore-Forming Activity of PorB

The pore-forming capabilities of PorB were tested using the liposome reconstitution assay (Nikaido (1983) *Methods Enzymol.* 97:85-95). The liposome swelling assay for study of porin function is used not only because it is well established, but because this assay gives precise information on the rates of diffusion of solutes through the porin channels (Nikaido & Rosenberg (1983) *J. Bacteriol.* 153:241-252). This assay involves the formation of liposomes incorporated with pore-forming protein and then determination of whether and how fast test solutes can diffuse through the protein channels. This assay was used to test and compare pore-forming activity of the *C. trachomatis* PorB and MOMP.

Purification of MOMP using mild detergents causes a loss in porin activity (Bavoil, et al. (1984) *Infect. Immun.* 44:479-485, Wyllie, et al. (1998) *Infect. Immun.* 66:5202-5207), therefore, MOMP was expressed in *E. coli* and outer membrane fractions enriched for MOMP were used. It has been shown in liposome swelling assays that the predominant porin activity of the outer membrane fraction of *E. coli* expressing MOMP is due to MOMP (Jones et al. (2000) *Gene* 258:173-181). This was also found to be the case for PorB except purified PorB also functioned in liposome swelling assays (FIG. 4) and was used in all subsequent experiments. To control for potential contaminants that may occur during PorB purification, another predicted outer membrane protein from *C. trachomatis* serovar D (CT241) was cloned, expressed in *E. coli* and purified by the same procedure used for PorB. Like PorB, CT241 also contains a predicted leader sequence and ends in phenylalanine and was incorporated into liposomes and tested for pore forming activity. This protein as well as liposomes without protein did not show pore-forming activity with any of the solutes tested.

Figure 4B:
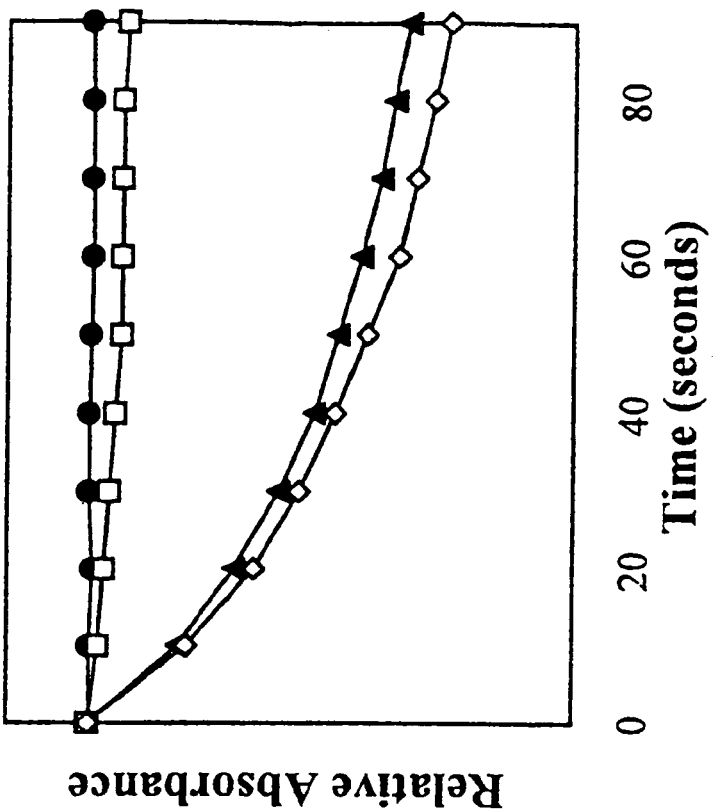
FIGS. 4A and 4B are graphs showing the results of a liposome swelling analysis of PorB (FIG. 4A) and the outer membrane of *E. coli* expressing MOMP (panel B). Liposomes were made as described and 0.017 ml out of a total of 0.3 ml was diluted in 0.6 ml of isotonic sugar solutions of stachyose (closed circles), sucrose (open squares), glucose (closed triangles) and arabinose (open circles). The y-axis represents a range of $A_{400}$ 0.15.
Figure 4A:
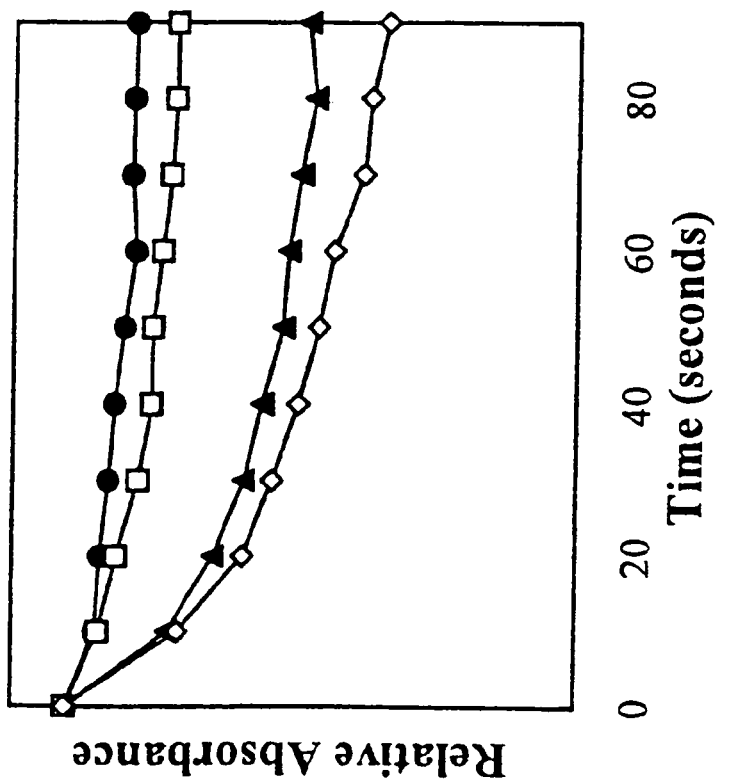

The smallest sugars tested in the liposome swelling assay were the monosaccharides arabinose and glucose. These sugars penetrated the PorB- and MOMP-containing liposomes faster than the disaccharide, sucrose, while the tetrasaccharide, stachyose, was too large to enter (FIG. 4). This diffusion selectivity of PorB- or MOMP-containing liposomes with sugars was similar to what has been observed with COMC-containing liposomes (Bavoil, et al. (1984) *Infect. Immun.* 44:479-485, Wyllie, et al. (1998) *Infect. Immun.* 66:5202-5207). Larger solutes enter into PorB or MOMP porin slower, suggesting that there is a size restriction of molecules that can enter via these porins. However, the liposomes containing PorB permitted the diffusion of arabinose or glucose at a slower rate than liposomes containing MOMP.

Figure 5B:
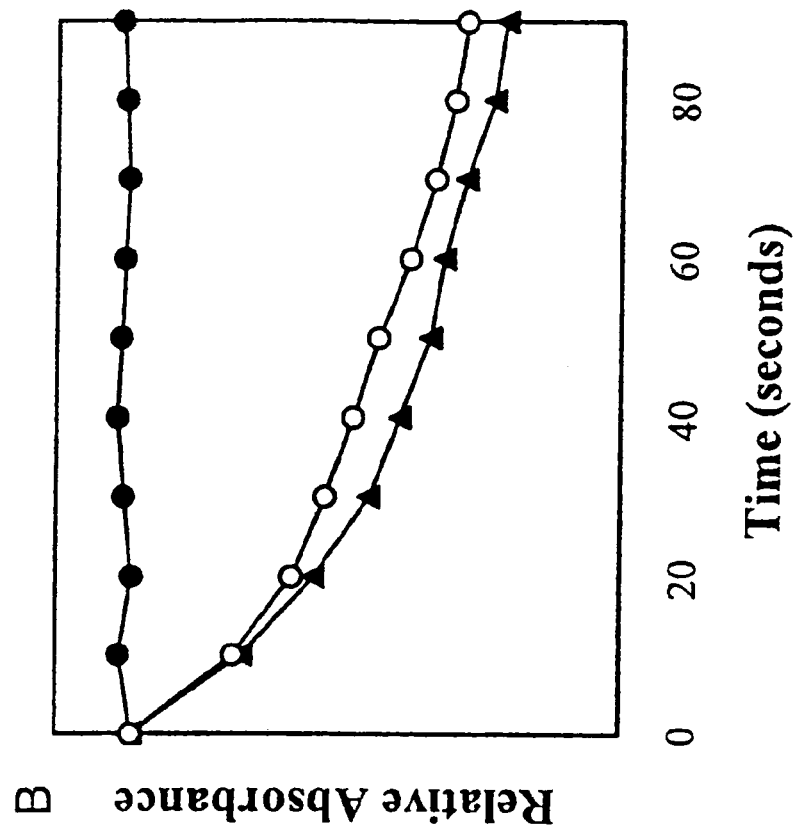
FIGS. 5A-5B are graphs showing lack of amino acid transport through PorB. Liposome swelling analysis of PorB (panel A) and the outer membrane of *E. coli* expressing MOMP (panel B). Liposomes were made as described and 0.017 ml out of a total of 0.3 ml was diluted in 0.6 ml of isotonic sugar solutions of stachyose, arabinose (open circles) and alanine (closed triangles). The y-axis represents a range of $A_{400}$ 0.15.
Figure 5A:
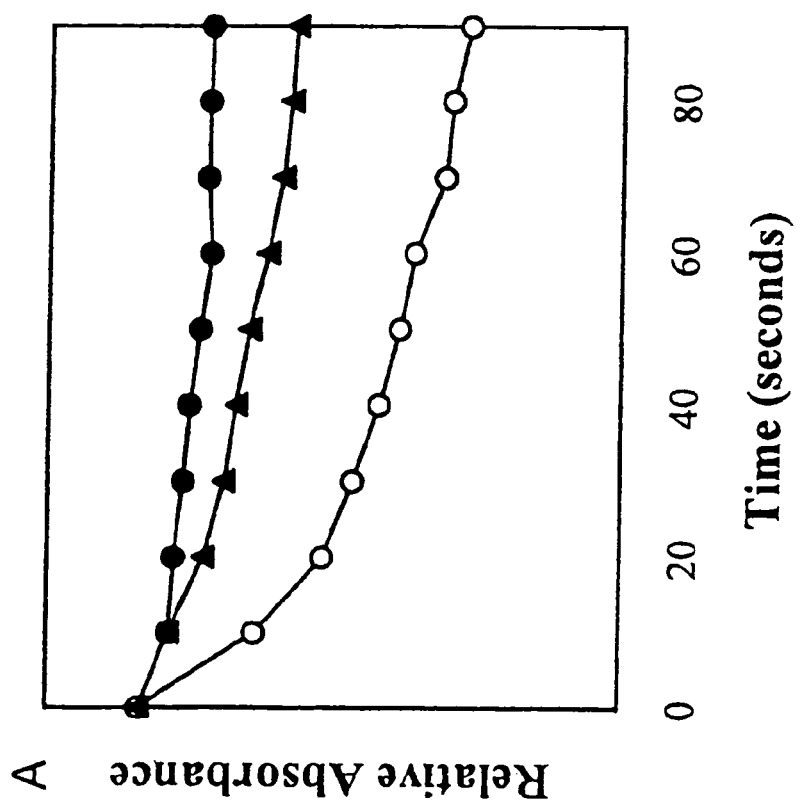

Since *Chlamydia* have been proposed to utilize amino acids from host cells (Ossowski et al. (1965) *Isr. J. Med. Sci.* 1:186-193; Hatch et al. (1982) *J. Bacteriol.* 150:379-385; Pearce, (1986) *Ann. Inst. Pasteur Microbiol.* 137A:325-332), diffusion of amino acids through PorB and MOMP were tested using the liposome swelling assay. MOMP liposomes allow for the diffusion of all of the amino acids at different rates based predominantly on size selectivity and alanine and glycine enter through MOMP liposomes slightly faster than arabinose (Jones et al. (2000) *Gene* 258:173-181). In contrast, PorB liposomes did not efficiently allow for any of 20 amino acids to enter liposomes including the small amino acids such as alanine (FIG. 5). These data indicate that PorB is less efficient than MOMP as a non-specific porin.

Example 10

Permeability of Solutes Through PorB

PorB was purified by nickel column chromatography and incorporated into liposomes. Liposomes enriched for MOMP were used to compare the pore-forming activity of PorB. As shown above, PorB porin function, unlike MOMP, is inefficient in the diffusion of amino acids, even amino acids smaller in molecular weight than arabinose, such as glycine and alanine. MOMP porin activity is detected using only 1 µg of protein (total outer membrane protein) while 6-10 µg of purified PorB is needed to observe comparable porin activity. This suggests that PorB is much less efficient as a non-specific porin or that the purification process may have resulted in a less functional protein.

Differences in general pore-forming activity, as well as differences in the amount present in the *chlamydial* outer membrane, suggest a unique role for each of the porins. The presence of PorB in small amounts is difficult to understand unless PorB has a role as a substrate-specific porin that is efficient in the uptake of particular classes of molecules. RT-PCR analysis and cell staining at various time points indicated that this protein is expressed throughout the developmental cycle. Thus PorB expression is not differentially regulated.

In order to determine if PorB had specificity for any molecule(s), the genome sequence was studied to determine if the inferred biology of *Chlamydia* could provide an idea of which molecules *Chlamydia* might need to obtain from the host. This analysis provided a list of orthologs of transporters that are important in the translocation of solutes across the inner membrane, including amino acid, polysaccharide, oligopeptide, and dicarboxylate transporters (Stephens et al. (1998) *Science* 282:754-759). Previous analysis of MOMP porin activity showed that amino acids, mono- and di-saccharide and oligopeptides enter efficiently through MOMP (Jones et al. (2000) *Gene* 258:173-181). However, PorB did not allow for the efficient entry of either amino acids or polysaccharides. The presence of an ortholog to an inner membrane dicarboxylate transporter, and that *Chlamydia* appears to have a truncated TCA cycle, suggest that chlamydiae may require exogenous α-ketoglutarate from the host cell. Therefore, the hypothesis that dicarboxylates could enter through the *chlamydial* outer membrane was tested by measuring α-ketoglutarate diffusion through the two known porins, PorB and MOMP.

Figure 6B:
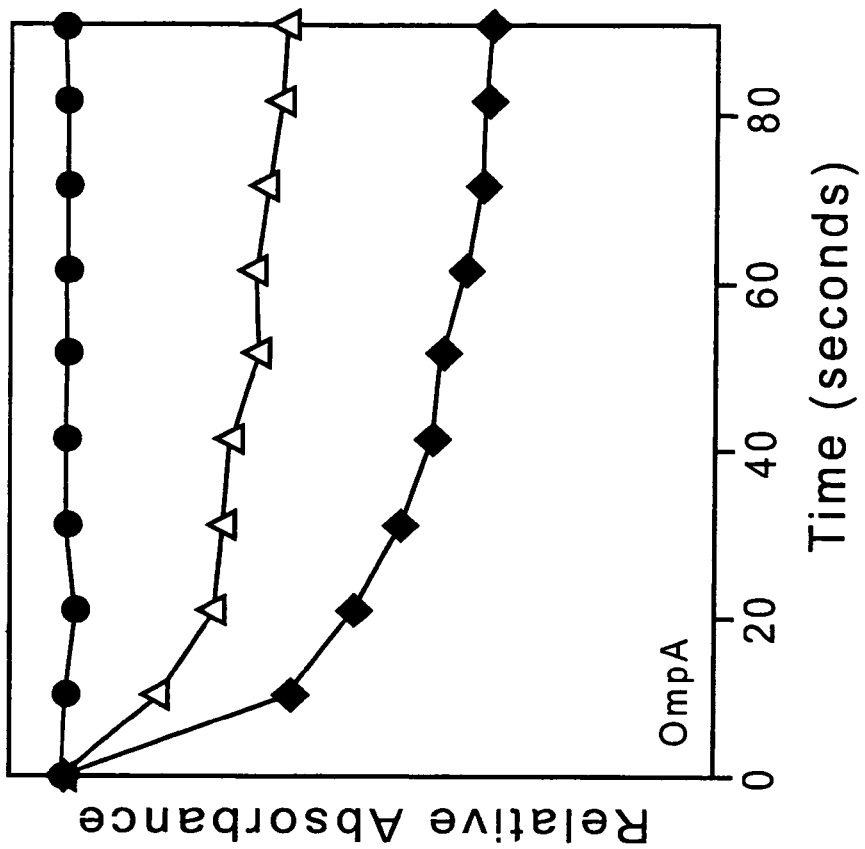
FIGS. 6A and 6B are graphs showing the results of a liposome swelling analysis of PorB (panel A) and the outer membrane of *E. coli* expressing MOMP (OmpA) (panel B). Isotonic solutions of stachyose (closed circles), arabinose (closed diamonds) and α-ketoglutarate (open triangles). The y-axis represents a range of $A_{400}$ 0.15.
Figure 6A:
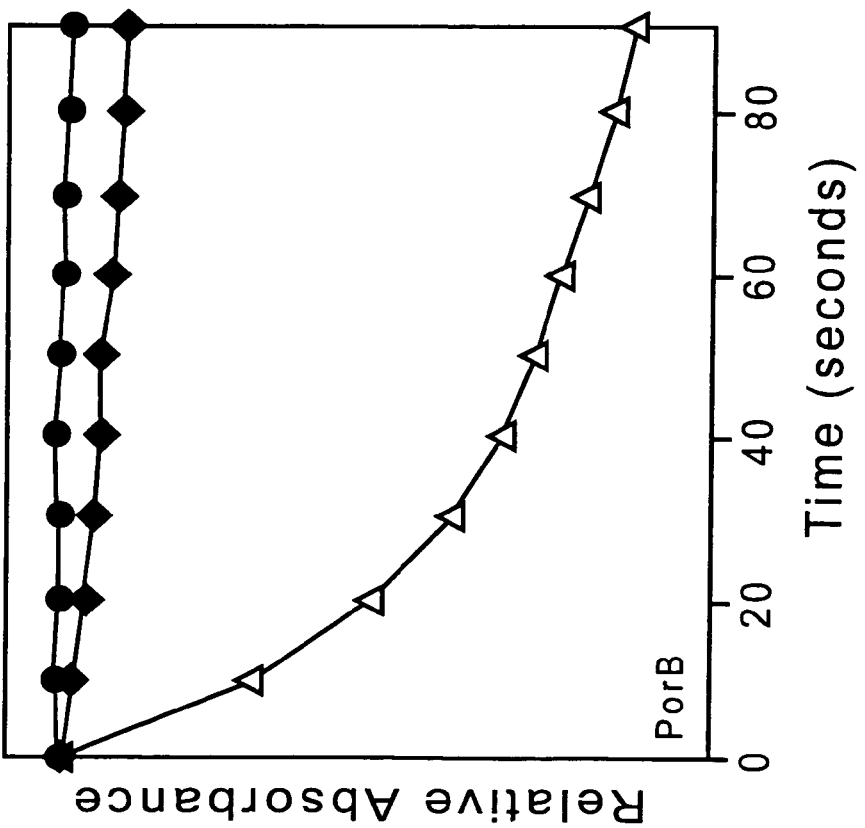

The liposome swelling assay with PorB and MOMP showed that the diffusion of α-ketoglutarate was more efficient through PorB than MOMP (FIG. 6). No diffusion of α-ketoglutarate was seen with liposomes without protein, as well as liposomes with another *chlamydial* outer membrane protein (Omp85) that was purified by the same method as PorB. *Chlamydial* Omp85 was used as a control protein that was cloned, expressed in *E. coli* and purified by the same method used to purify PorB. *E. coli* not expressing PorB, which was treated the same way as *E. coli* expressing PorB, was purified by nickel column chromatography and the column eluate was used as a control in all of the assays to verify that no *E. coli* contaminants were responsible for the porin activity observed.

Figure 7:
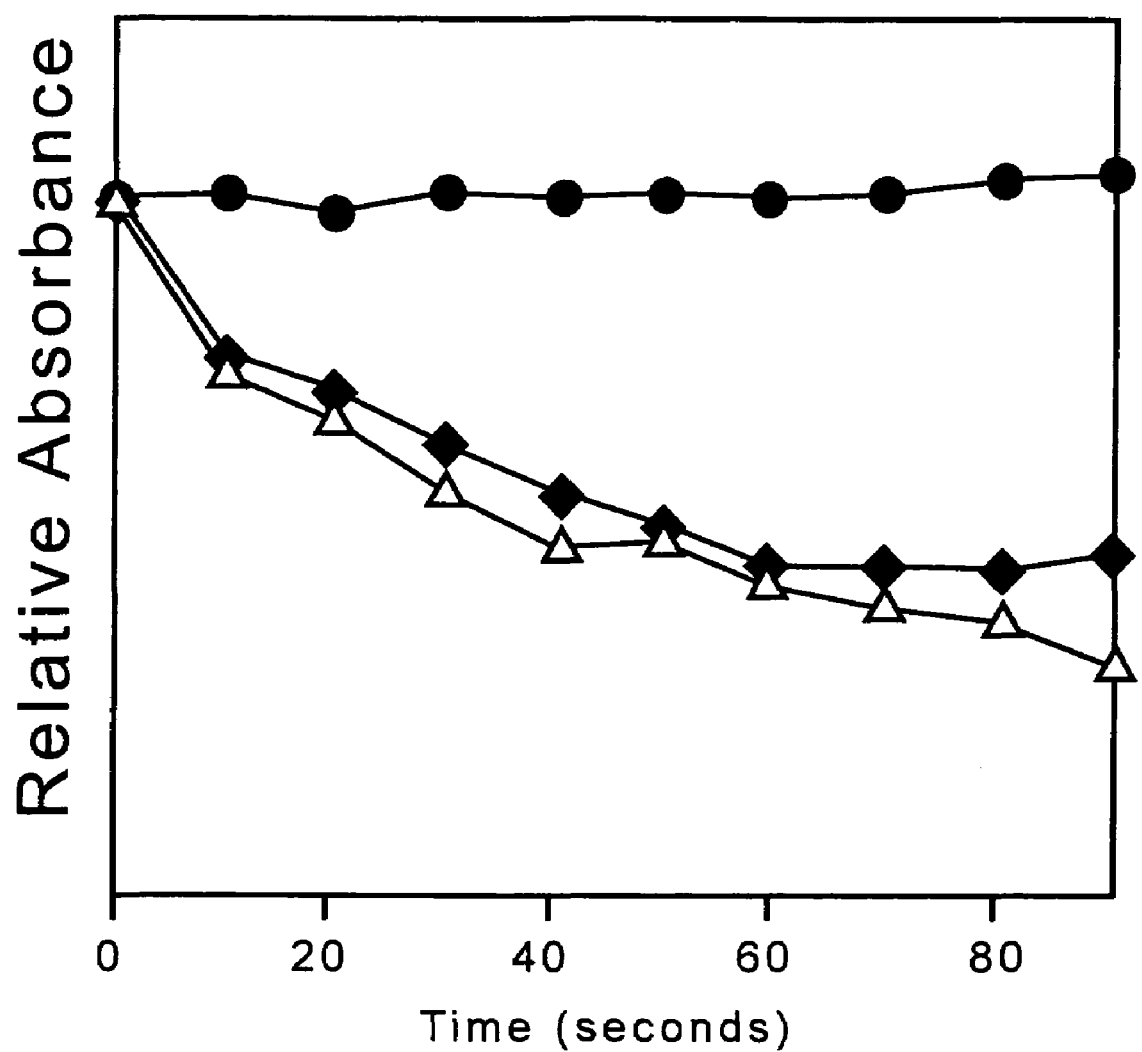
FIG. 7 is a graph showing the results of a liposome swelling assay to control for effects of ions that may be present in the test solute. Liposomes containing $NAD^+$, stachyose, and imidazone-NAD were diluted in isotonic test solutions of citrate (closed circles), oxaloacetate (closed diamonds), and α-ketoglutarate (open triangles). The y-axis represents a range of $A_{400}$ 0.15.

One concern with the liposome assays was the possible influence of ions present in anionic solutes, such as α-ketoglutarate, that may cause ion fluxes potentially confounding the results of the assay. A liposome assay to control for the possibility of ion fluxes (Nikaido and Rosenberg (1983) J. Bacteriol. 153:241-252) was used to confirm the swelling assay results. Liposomes were made with $NAD^+$-imidazole and stachyose to counteract any ion fluxes that may result from the presence of contaminating ions in the α-ketoglutarate solute used for the assay. This assay confirmed that the results in the initial liposome assays were not the result of ion fluxes and that oxaloacetate also entered efficiently through PorB while citrate did not enter (FIG. 7).

Figure 8:
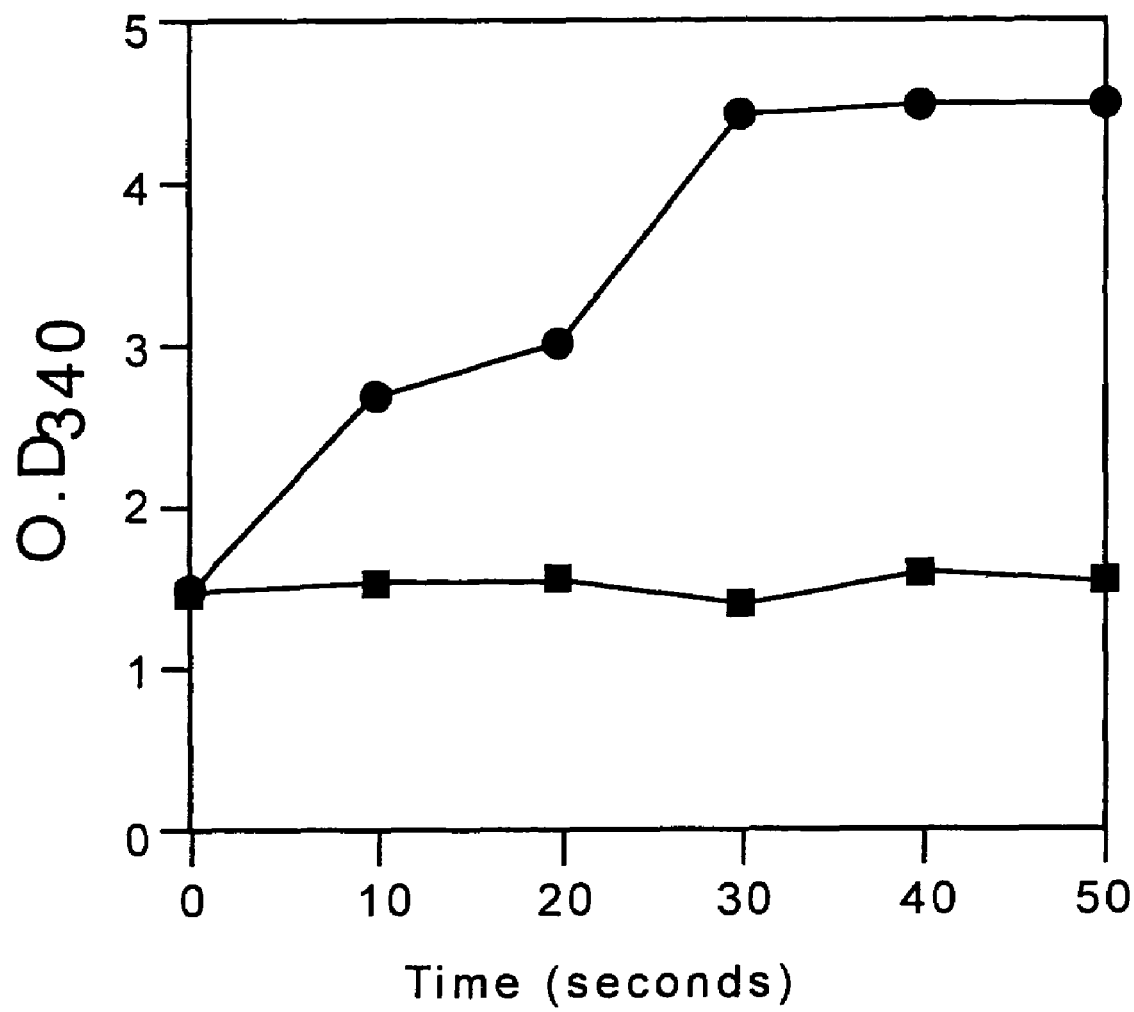
FIG. 8 is a graph showing enzyme-linked liposome assay testing of the entry and oxidation of α-ketoglutarate. The formation of NADH using liposomes containing PorB (closed circles) or lacking PorB (closed squares) was measured by an increase in $O.D._{340}$.

An enzyme-linked liposome assay was used to further show that the α-ketoglutarate was entering through PorB. The liposomes were made with α-ketoglutarate dehydrogenase and $NAD^+$ inside and washed. The substrate, α-ketoglutarate, was added to the outside of the liposomes and then the liposomes were measured for the formation of NADH by the increase in the $O.D._{340}$. This shows that α-ketoglutarate entered through PorB unlike the control liposomes which did not allow α-ketoglutarate to enter inside and result in the formation of NADH (FIG. 8).

Example 11

TCA Cycle Molecules Enter Through PorB

Figure 9:
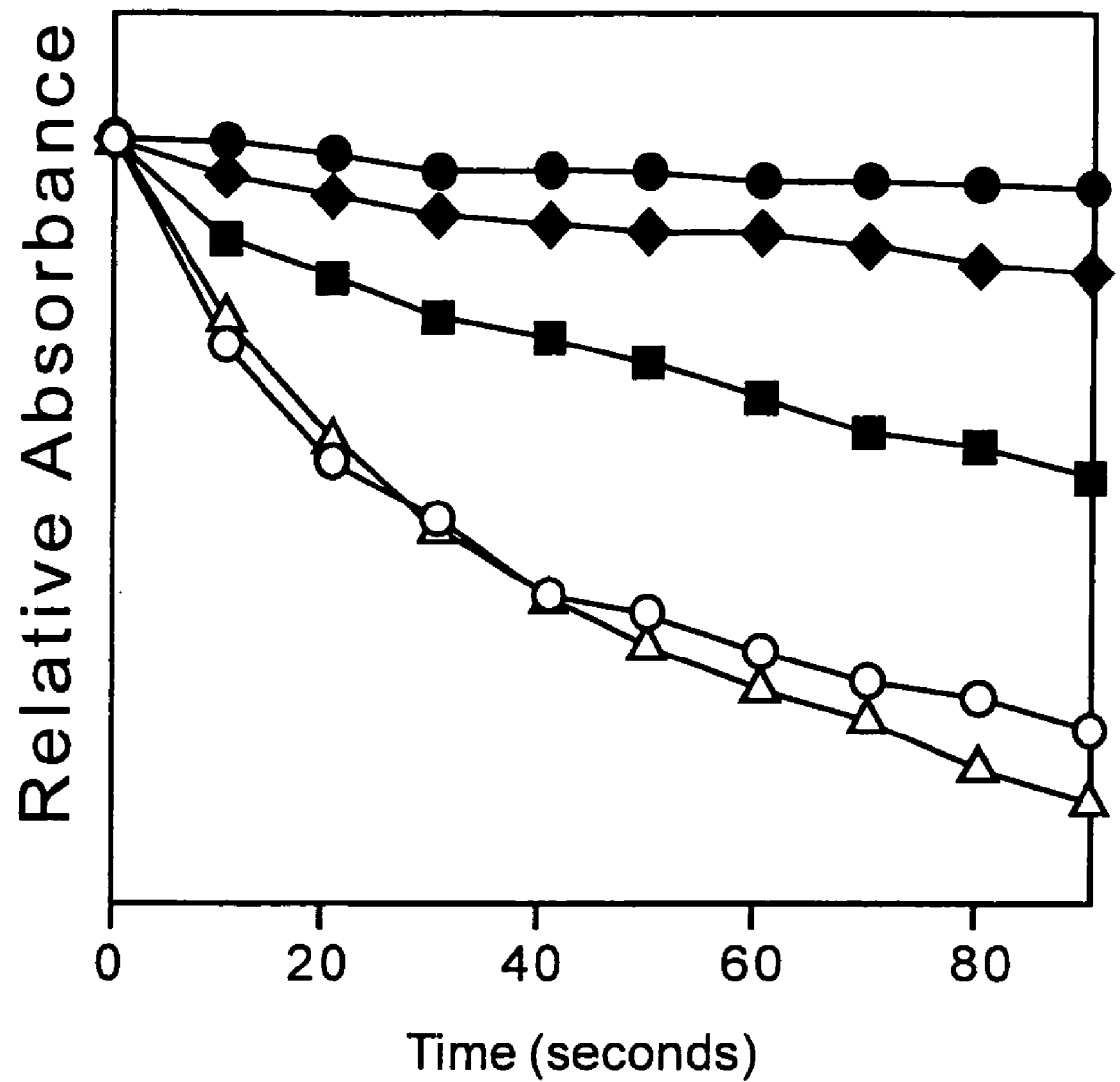
FIG. 9 is a graph showing liposome swelling analysis of PorB using TCA-cycle intermediates. Isotonic sugar solutions of stachyose (closed circles), arabinose (closed diamonds), α-ketoglutarate (open triangles), malate (closed squares) and succinate (open circles). The y-axis represents a range of $A_{400}$ 0.15.

Since α-ketoglutarate efficiently entered through PorB, a number of other TCA cycle intermediates were tested to assess whether this porin was specific for the α-ketoglutarate substrate. Succinate (and oxaloacetate) enter PorB with similar rates to α-ketoglutarate; however, malate did not enter efficiently (FIG. 9). Citrate did not enter through PorB.

Example 12

Permeability Specificity Studies With PorB

Figure 10:
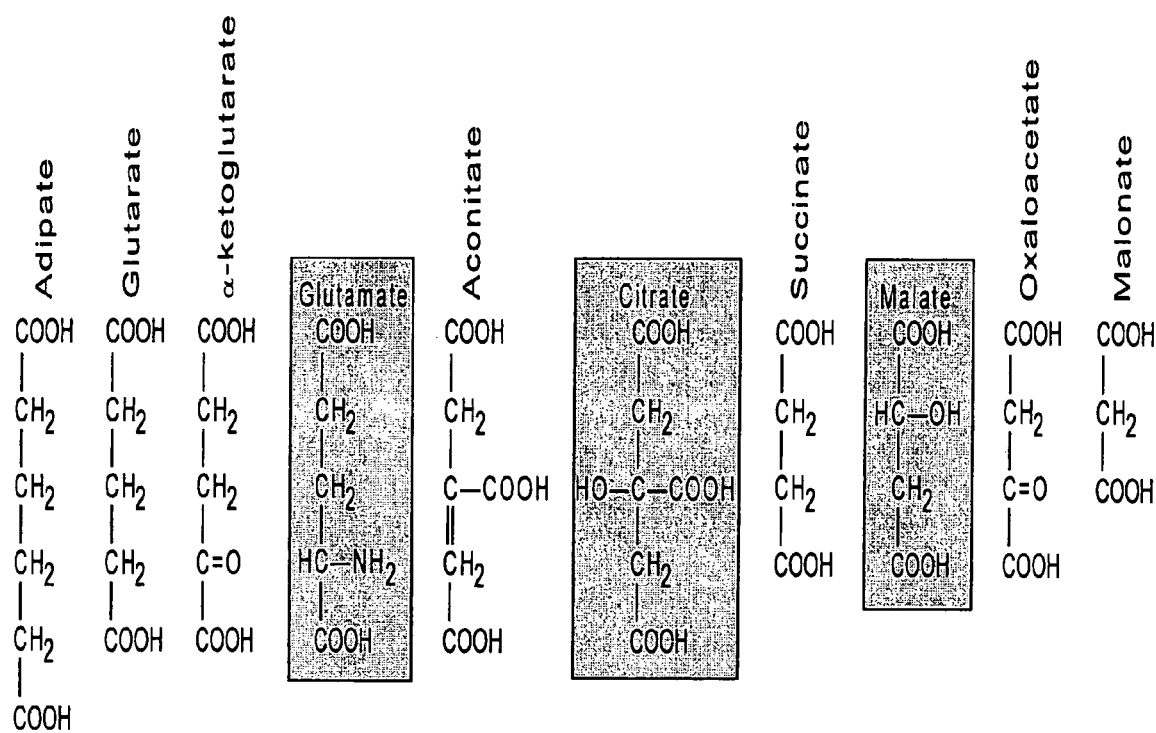
FIG. 10 is a schematic showing the structures of compounds tested for diffusion into liposomes containing PorB. Compounds in shaded boxes were not efficiently transported by PorB.

Since dicarboxylates of the TCA cycle were tested and diffused through PorB, other molecular analogues were studied to determine the capability of PorB to distinguish between related molecules (FIG. 10). A difference in carbon-chain lengths represented by adipate, glutarate, succinate, and malonate did not show marked differences in diffusion compared to α-ketoglutarate, although 6-carbon adipate and 3-carbon malonate entered through PorB at a slightly slower rate. Thus PorB did not discriminate between different substrate chain lengths. The effects of small side groups using analogues that differed only by specific side groups were tested. For example, α-ketoglutarate and glutarate entered through PorB efficiently, but not glutamate that is similar in structure. The presence of the amino group seems to retard the diffusion of glutamate and this likely explains why other amino acids do not enter into PorB efficiently. A comparison of 5-carbon compounds citrate and aconitate with only the addition of a hydroxyl group to citrate prevented the entry of citrate through PorB. Four-carbon malate and succinate also differ by the presence of a hydroxyl group and the diffusion rate was retarded for malate. Therefore, PorB can discern between very similar compounds to allow for specific selectivity, suggesting a substrate-specific selective porin. These findings show that PorB facilitates the diffusion α-ketoglutarate and other select dicarboxylates to enter *chlamydial* outer membranes efficiently.

Materials and Methods for Examples: 13-18

The following materials and methods were utilized for Examples 13-18 in conjunction to the materials and methods mentioned above, where appropriate.

Cloning, expression and purification of PorB. The gene encoding PorB (porB) was cloned into the pBAD TOPO-TA® vector and transformed into *E. coli* TOP10® competent cells (Invitrogen, Carlsbad, Calif.) as described by Kubo and Stephens (Kubo and Stephens (2000) Mol Microbiol 38:772-780). Host cells containing the recombinant PorB plasmid were grown in Luria-Bertani at 37° C. until an $A_{600}$ of 0.5 was attained. Protein expression was induced by addition of arabinose at a final concentration of 0.02%, and the cultures were incubated for an additional 3 h. PorB was extracted with 1% octylglucoside at 37° C. for 1 h followed by dialysis against PBS. The recombinant protein was then purified by nickel column purification using the His-Bind® purification system (Novagen, Madison, Wis.).

Preparation of synthetic peptide conjugates. Twenty-five overlapping peptides representing the entire PorB sequence were synthesized (Genemed Synthesis Inc., South San Francisco, Calif.; Table 2). Stock solutions of the PorB peptides (designated B1-1 to B5-5) were prepared in distilled water at a final concentration of 1 mg/ml and stored at −20° C. The peptides were coupled to Imject® maleimide activated-Keyhole Limpet Hemocyanin (KLH; Pierce Endogen, Rockford, Ill.) at a 1:1 ratio of peptide to KLH according to the manufacturers instructions. Briefly, 1 mg of maleimide-activated KLH was mixed with 1 mg of PorB peptide in a final volume of 1 ml and incubated for 2 h at room temperature. The conjugated protein was dialyzed against PBS (pH 7.4) for 3 h with three buffer changes. Purified peptide-KLH conjugates were stored at −20° C. until used.

Polyclonal immune sera. Human immune sera were obtained from individuals naturally infected with *C. trachomatis*. Polyvalent antisera to *C. trachomatis* serovar B was obtained from rabbits immunized with purified EB as previously described (Caldwell, H. D., C. C. Kuo, and G. E. Kenny (1975) J Immunol 115:963-968). Monospecific polyclonal antisera to recombinant PorB and synthetic PorB peptide conjugates were produced in Swiss Webster mice (Harlan, San Diego Calif.). Five 6-8 week old female mice were immunized by subcutaneous injection with 15 μg of purified PorB protein or 100 μg peptide-KLH conjugate in an equal volume of Complete Freund's Adjuvant. Intraperitoneal boost immunizations were performed two weeks later in Incomplete Freund's Adjuvant. After an additional two weeks, mice were tested for reactivity to homologous peptide by peptide-specific ELISA. Institutional Review Board approval was obtained for use of human sera and immune sera production in rabbits and mice.

Peptide-specific ELISA. Mouse immune sera to PorB peptides were screened by ELISA using homologous peptide as coating antigen. Polystyrene microtiter plates (IMMULON 2; Dynatech, Chantilly, Va.) were coated with 50 μl of 5 μg/ml of peptide per well in 50 mM bicarbonate buffer (pH 9.6) and incubated overnight at 37° C. After washing twice with PBS-Tween (PBS; 0.05% TWEEN 20), the wells were incubated with 100 μl blocking buffer containing 2% gelatin in PBS for 1 h at 37° C. and then washed with PBS-Tween. A 50 μl volume of a 1:1000 dilution of the mouse antisera was added and the plates incubated for 1 h at 37° C. The wells were washed three times with PBS-Tween, and incubated with a 1:2000 dilution of goat anti-mouse IgG-horseradish peroxidase (HRP) conjugated antibody (Zymed laboratories, South San Francisco, Calif.) for 1 h at 37° C.

After washing three times in PBS-Tween and twice in PBS, the antibody complexes were detected with a mixture of substrate (0.1% hydrogen peroxide) and chromogen (1 mg/ml o-phenelynediamine; Dako Corporation, Carpinteria, Calif.) in 0.1 M citrate buffer. The color was allowed to develop for 15 min and the reaction was terminated by addition of 25 µl of 8N $H_2SO_4$. The absorbance at 492 nm was measured on a Titertek Multiscan ELISA plate reader (Flow Laboratories, McLean, Va.). Each assay was run in duplicate. Human and rabbit immune sera were tested for reactivity to PorB peptides in a similar ELISA format at 1:1000 dilutions. Samples were treated with either goat anti-human IgG-HRP or goat anti-rabbit IgG-HRP conjugates (Zymed laboratories, South San Francisco, Calif.) as secondary antibody and binding to PorB peptide was detected as described above.

Surface accessibility ELISA. The ability of PorB peptide antisera to recognize their cognate epitopes on the surface of viable *chlamydiae* was determined by absorption ELISA. Peptide antisera were adjusted to a dilution corresponding to a $A_{492}$ range of 0.4 to 1.8 and pre-incubated for 30 min at room temperature with purified *chlamydial* EB (~$10^8$ IFU/ml). After centrifugation to remove the EB, the peptide antisera were tested for residual reactivity to homologous PorB peptide or recombinant PorB as described in the ELISA method above. The difference in reactivity ($A_{492}$) between the absorbed and unabsorbed peptide antisera was calculated and statistically analyzed by a Student t-test. The absorption experiments were repeated twice.

*Chlamydial* dot-blot assay. The dot-blot assay was performed as previously described by Zhang et al (Zhang, Y. X. et al (1987) *J Immunol* 138:575-581). Briefly, nitrocellulose membrane (Bio-Rad Laboratories, Hercules, Calif.) was presoaked in PBS for 10 min and assembled onto a dot-blot apparatus (Bio-Rad Laboratories, Hercules, Calif.). A 50 µl suspension of *chlamydial* EB (5 µg/ml) in PBS was added to appropriate wells and was allowed to filter by gravity for 10 min followed by vacuum filtration for 5 min to remove all liquid from the wells. The membrane was removed and treated with a blocking solution (2% dried skim milk in PBS) on a rocker for 1 h at room temperature. After three washes in PBS-Tween, the membrane was re-assembled. Dilutions of peptide antisera were added to corresponding wells and incubated for 1 h at room temperature.

After the wells were washed three times with 200 µl PBS-Tween, the membrane was removed from the blotting apparatus and washed three more times with PBS-Tween. A 1:2000 dilution of goat anti-mouse IgG HRP-conjugate was added to the membrane as secondary antibody and incubated for 1 h at room temperature. After three washes in PBS-Tween, the membrane was treated with enhanced chemiluminescence (ECL) detection reagents (Amersham Pharmacia Biotech, Piscataway, N.J.) and subjected to autoradiography for 5 sec using Kodak X-omat AR film (Eastman Kodak Co., Rochester, N.Y.). Controls included probing immobilized EB with (a) 2C5, a monoclonal antibody to the species-specific VS4 region of MOMP, (b) pre-immune sera and (c) anti-Pgp3, an inner membrane *chlamydial* protein.

In vitro neutralization. In vitro neutralization assays using HaK (Syrian Hamster Kidney) cells were performed as previously described (Byrne, G. I., R. S. Stephens, and et al. (1993) *J Infect Dis* 168:415-420). Serial dilutions of monospecific PorB peptide antisera, were prepared in SPG. Mouse antisera produced to full-length PorB was used as positive control and pre-immune sera and SPG were used as negative controls. *C. trachomatis* serovar D EB were diluted in SPG to contain $2 \times 10^4$ inclusion forming units (IFU)/ml and 90 µl were added to each serum dilution in a final volume of 180 µl. Neutralization was allowed to proceed for 30 min at 37° C. 50 µl of each sample were added in triplicate to PBS-washed HaK monolayers and incubated for 2 h at 37° C. After excess inoculum was removed, the cells were rinsed once with PBS, replenished with 200 µl of RPMI medium supplemented with 10% fetal bovine serum and 1 µg/ml cycloheximide, and incubated at 37° C. for 48 h. *Chlamydial* inclusions were detected by staining with mouse anti-*C. trachomatis* MOMP fluorescent antibody (Wampole Laboratories, Cranbury, N.J.) and quantified by counting 3 fields per well at a magnification of 40×. The results were calculated as percentage reduction in mean IFU relative to the control SPG. Assays were performed in triplicate.

Example 13

Epitope Mapping With Immune Sera

The first step in elucidating the structure of PorB was to determine which regions of the protein are antigenic. To define antigens of PorB, the binding of human immune sera, rabbit anti-EB sera and mouse anti-PorB sera to 25 synthetic overlapping peptides spanning the PorB sequence (Table 2) was tested by peptide-specific ELISA. Peptides with high frequencies and high titers of reactivity to the different polyclonal immune sera were considered immunoreactive.

Figure 11:
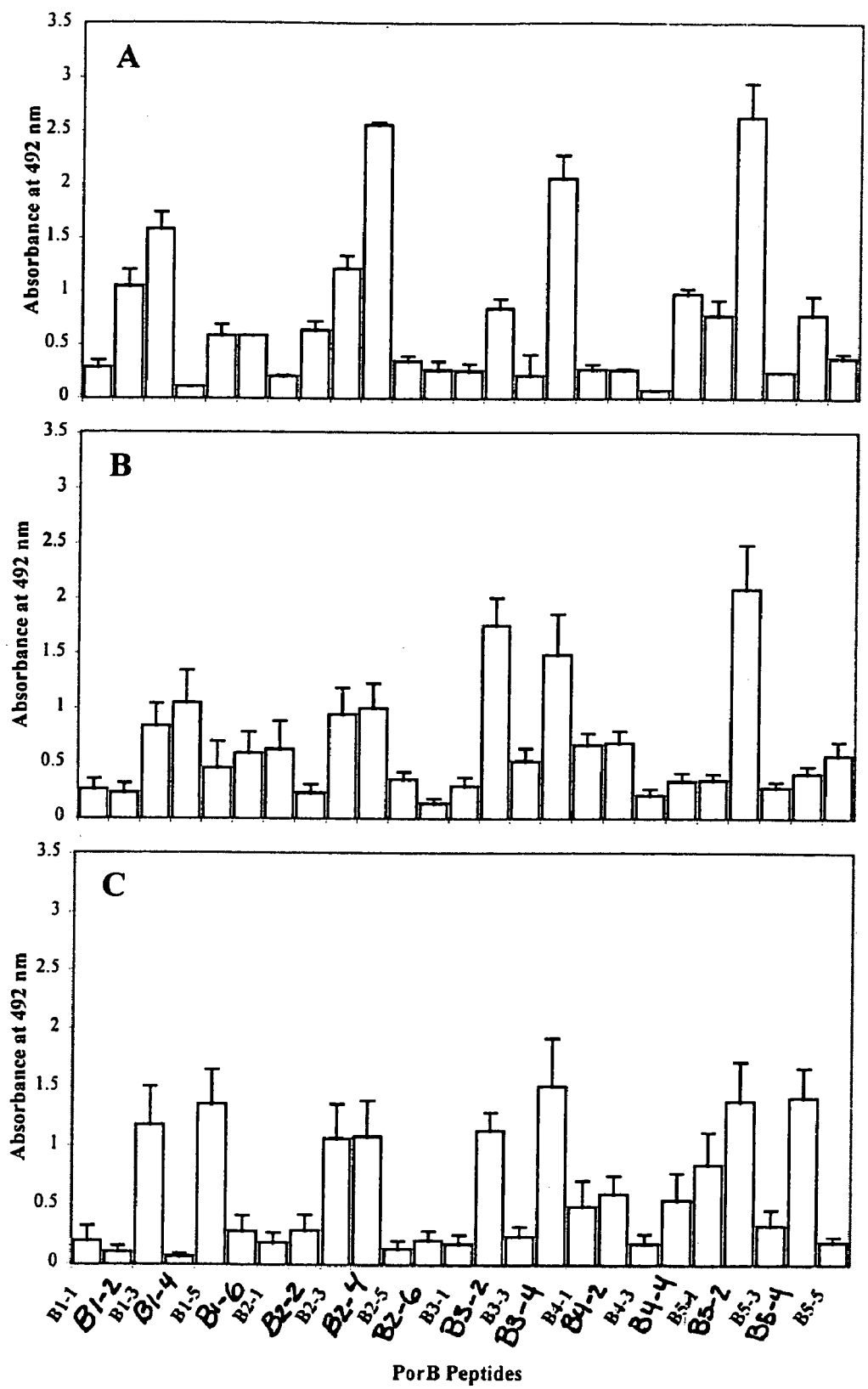
FIG. 11. is a graph showing the results of epitope mapping of PorB protein. Polyclonal immune sera were used to probe overlapping synthetic peptides representing the entire PorB sequence. Each vertical bar represents the mean absorbance (±SEM) of a peptide in the peptide-specific ELISA. Reactivities for pooled rabbit antisera raised against purified *chlamydial* EB (Panel A), pooled sera from humans infected with *C. trachomatis* (Panel B) and sera from mice immunized with purified PorB (Panel C) are shown. Sera were tested at a 1:1000 dilution.

Using these criteria, four major neutralizing epitope clusters corresponding to $Phe_{34}$-$Leu_{59}$ (B1-2 and B1-3), $Asp_{112}$-$Glu_{145}$ (B2-3 and B2-4), $Gly_{179}$-$A_{225}$ (B3-2, B3-3 and B3-4) and $Val_{261}$-$Asn_{305}$ (B4-4, B5-1 and B5-2) were identified (FIG. 11). Each neutralizing epitope domain comprised 2-3 epitopes, with higher peaks of reactivity noted for individual peptides B1-3, B2-3, B2-4, B3-4 and B5-2 for all sera tested. The C-terminal end of the protein appeared as a major immunoreactive region with two epitope clusters in close proximity. Although variations in individual reactivities exist, all antisera recognized the same determinants, indicating that these epitopes are broadly antigenic. Each of the individual sera showed reactivity to purified PorB antigen in a similar ELISA format, confirming that antibody recognition of the PorB peptides was specific (data not shown). Except for peptide B2-3 that contained a stretch of hydrophobic residues in its C-terminal region, most of the reactive epitopes were hydrophilic. The hydrophilicity and reactivity of the immunoreactive epitopes suggest that they may be surface-accessible and targets of neutralizing immune responses.

TABLE 2

Synthetic Peptides Representing PorB Amino Acid sequence[a]

| PEPTIDE | SEQUENCE | SEQ ID NO. |
|---------|----------|------------|
| B1-1 | LDAMPAGNPA<u>FPVIPG</u>[b] | (SEQ ID NO. 35) |
| B1-2 | <u>FPVIPG</u>INIE<u>QKNACS</u> | (SEQ ID NO. 11) |
| B1-3 | <u>QKNACS</u>FDLC<u>NSYDVL</u> | (SEQ ID NO. 12) |
| B1-4 | <u>NSYDVL</u>SALS<u>GNLKLC</u> | (SEQ ID NO. 21) |
| B1-5 | <u>GNLKLC</u>FCGD<u>YIFSEE</u> | (SEQ ID NO. 22) |
| B1-6 | <u>YIFSEE</u>AQVK<u>DVPVVT</u> | (SEQ ID NO. 23) |
| B2-1 | <u>DVPVVT</u>SVTTAGVG<u>PSPDIT</u> | (SEQ ID NO. 24) |
| B2-2 | <u>PSPDIT</u>STTKTRNF<u>DLVNCN</u> | (SEQ ID NO. 25) |
| B2-3 | <u>DLVNCN</u>LNTNCVAV<u>AFSLPD</u> | (SEQ ID NO. 13) |

TABLE 2-continued

Synthetic Peptides Representing PorB Amino Acid sequence[a]

| PEPTIDE | SEQUENCE | SEQ ID NO. |
|---|---|---|
| B2-4 | AFSLPDRSLSAIPL<u>FDVSFE</u> | (SEQ ID NO. 14) |
| B2-5 | FDVSFEVKVGGLK<u>QYYRLP</u> | (SEQ ID NO. 26) |
| B2-6 | QYYRLPMNAYRDF<u>TSEPLNS</u> | (SEQ ID NO. 27) |
| B3-1 | TSEPLNSESEVTD<u>GMIEVQS</u> | (SEQ ID NO. 28) |
| B3-2 | GMIEVQSNYGFVW<u>DVSLKKV</u> | (SEQ ID NO. 15) |
| B3-3 | DVSLKKVIWKDGVS<u>FVGVGAD</u> | (SEQ ID NO. 16) |
| B3-4 | FVGVGADYRHASC<u>PIDYIIA</u> | (SEQ ID NO. 17) |
| B4-1 | PIDYIIANSQANPE<u>VFIADS</u> | (SEQ ID NO. 29) |
| B4-2 | VFIADSDGKLNFKE<u>WSVCVG</u> | (SEQ ID NO. 30) |
| B4-3 | WSVCVGLTTYVNDY<u>VLPYLA</u> | (SEQ ID NO. 31) |
| B4-4 | VLPYLAFSIGSVSR<u>QAPDDSF</u> | (SEQ ID NO. 18) |
| B5-1 | APDDSFKKLEDR<u>FTNLKF</u> | (SEQ ID NO. 19) |
| B5-2 | FTNLKFKVRKIT<u>SSHRGN</u> | (SEQ ID NO. 20) |
| B5-3 | SSHRGNICIGAT<u>NYVADN</u> | (SEQ ID NO. 32) |
| B5-4 | NYVADNFFYNVE<u>GRWGSQ</u> | (SEQ ID NO. 33) |
| B5-5 | GRWGSQRAVNVSGGFQF | (SEQ ID NO. 34) |

[a]Residues representing overlapping peptide regions are underlined. All peptides except B1-4 were synthesized with an additional cysteine at their C termini for conjugation to KLH.
[b]Residues are listed in single-letter code beginning at the N-terminal end.

Example 14

Determination of Surface Accessibility of PorB Epitopes

Neutralization of *chlamydial* infectivity requires that antigenic determinants are surface exposed and accessible for antibody recognition (Fan, J., and R. S. Stephens 1997) *J Infect Dis* 176:713-721; Toye, B., G. M. Zhong, R. Peeling, and R. C. Brunham (1990) *Infect Immun* 58:3909-3913). The experimental approach to determining whether the identified PorB epitopes are surface-accessible was to generate a panel of mouse antisera to each of 25 overlapping synthetic peptides representing PorB (Table 2), and to use these to probe for their cognate antigen on *chlamydial* EB in absorption ELISA and EB surface-specific dot-blot assays.

Characterization of Anti-peptide Conjugate Antibodies.

A panel of mouse antisera raised to overlapping synthetic PorB peptides was evaluated for reactivity by a peptide-specific ELISA assay. All sera reacted with their homologous peptides with mean end-point titers ($log_2$ values) ranging from 9 to 18 (Table 2). The reactivity of peptide-specific antisera to recombinant PorB or homologous peptides was reduced 58 to 95% by competitive inhibition with respective peptide, demonstrating that peptide recognition was specific (data not shown). ). In contrast, the peptide sera were unaffected by absorption with KLH and an unrelated *chlamydial* peptide Ct673 (data not shown). Since MOMP quantitatively predominates the surface of *chlamydial* EB and is known to mediate neutralization of infectivity, the panel of peptide antisera was tested for cross reactivity to this protein. No cross-reactivity of the peptide-specific antisera was observed as reactivity to recombinant MOMP protein was <0.3 $A_{492}$ for all sera tested (Table 2).

EB-Absorption Studies

Figure 12:
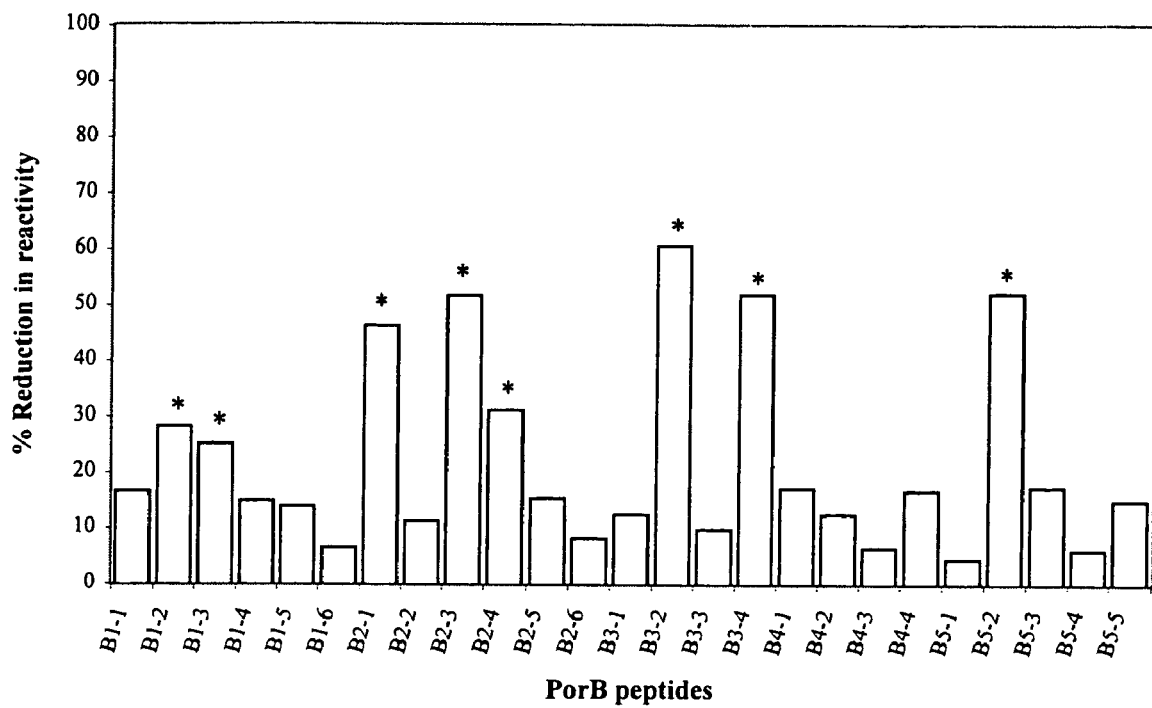
FIG. 12 is a graph showing the accessibility of PorB epitopes on the surface of *chlamydial* EB, as determined by pre-incubation of purified *chlamydial* EB with mouse antisera specific to the peptides and detection of residual reactivity to homologous peptide. The results are presented as % reduction in serum reactivity ($A_{492}$) to PorB peptides of the invention due to absorption with viable EB.
Figure 13:
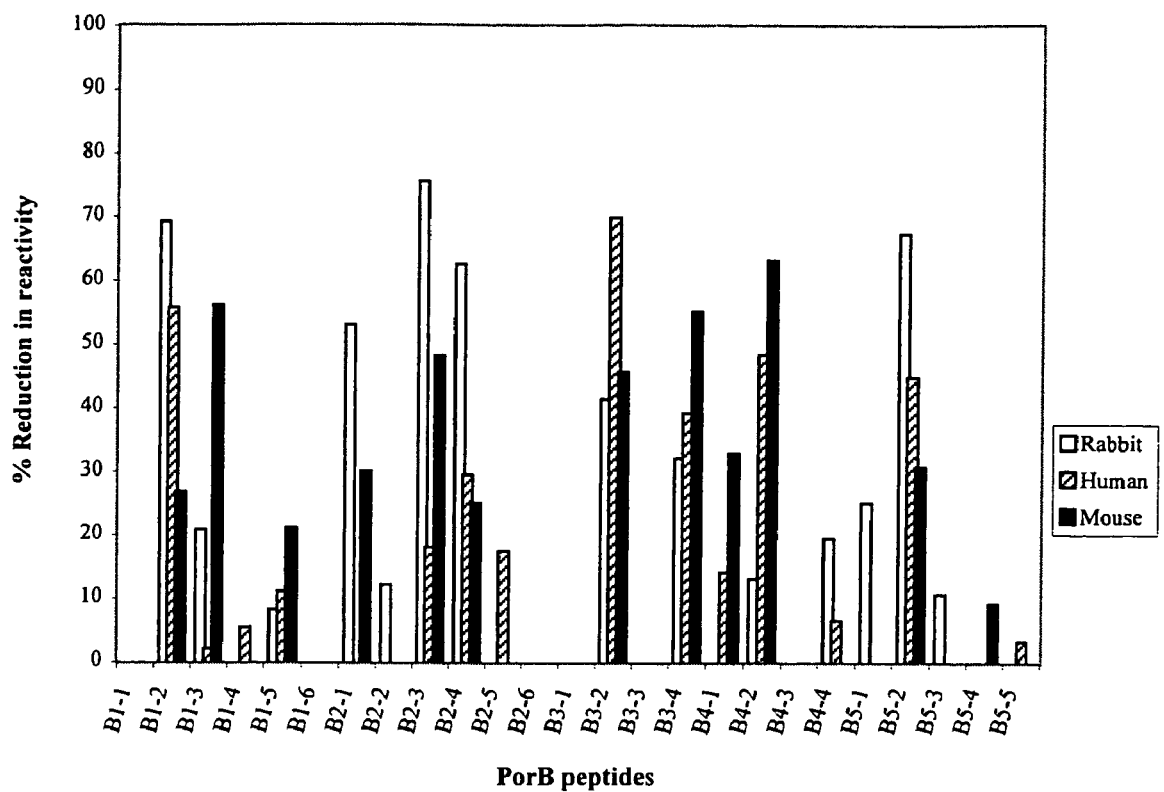
FIG. 13 is a graph showing the change in reactivities of EB-absorbed polyclonal immune sera to PorB peptides. Rabbit, human and mouse immune sera were pre-incubated with *chlamydial* EB and assayed for residual reactivity to PorB polypeptides of the of the present invention by ELISA. The results are presented as % reduction in serum reactivity ($A_{492}$) due to absorption with viable EB. Sera were tested at a 1:1000 dilution.

To determine which of the peptide-specific antibodies were directed at PorB epitopes on the *chlamydial* EB surface, absorption studies were conducted in an ELISA format. Peptide-specific antisera were pre-incubated with viable EB prior to testing for reactivity to PorB peptides and recombinant PorB. If absorption with intact EB reduced the reactivity of peptide-specific antibody compared to the unabsorbed sera, it can be inferred that the absorbed antibodies were directed toward surface-accessible epitopes on PorB. Absorption of sera raised to epitopes B1-2, B1-3, B2-1, B2-3, B2-4, B3-2, B3-4, and B5-2 with *chlamydial* EB resulted in a significant decrease in reactivity to their cognate peptides (FIG. 12; P<0.05). Antisera B2-3, B3-2, B3-4 and B5-2 showed the largest decreases in reactivity when absorbed with EB. In contrast, antisera B1-6 and B2-6, which showed high reactivity with their respective peptides (Table 3), showed no decreases in reactivity when absorbed with EB. This verified that the *chlamydial* EB were intact during absorption. Reactivity of peptide-absorbed antisera to recombinant PorB revealed similar profiles of surface-exposed epitopes indicating that the peptide-specific antibodies bind to cognate peptides as well as whole protein (data not shown). Likewise, when polyclonal immune sera from humans, rabbits and mice were pre-absorbed with EB and tested for reactivity with PorB peptides, a decrease in reactivity was observed for the same epitopes (FIG. 13). The data from EB-absorption studies supported the specificity of the peptide-antibody interaction and provided evidence that the immunoreactive PorB epitopes are surface-exposed.

TABLE 3

Immunological properties of mouse antisera raised against PorB peptide conjugates

| Antibody | Homologous peptide ELISA reciprocal titer ($log_2$)[a] | Cross-reactivity with rMOMP ELISA ($A_{492}$)[b] |
|---|---|---|
| B1-1 | 15[c] | 0.24 |
| B1-2 | 13 | 0.18 |
| B1-3 | 13 | 0.09 |
| B1-4 | 15 | 0.03 |
| B1-5 | 16 | 0.19 |
| B1-6 | 16 | 0.00 |
| B2-1 | 13 | 0.00 |
| B2-2 | 15 | 0.30 |
| B2-3 | 12 | 0.00 |
| B2-4 | 14 | 0.00 |
| B2-5 | 15 | 0.04 |
| B2-6 | 17 | 0.27 |
| B3-1 | 12 | 0.21 |
| B3-2 | 12 | 0.16 |
| B3-3 | 11 | 0.07 |
| B3-4 | 17 | 0.22 |
| B4-1 | 11 | 0.14 |
| B4-2 | 11 | 0.01 |
| B4-3 | 13 | 0.27 |
| B4-4 | 14 | 0.19 |
| B5-1 | 11 | 0.11 |
| B5-2 | 13 | 0.02 |
| B5-3 | 11 | 0.19 |

TABLE 3-continued

Immunological properties of mouse antisera
raised against PorB peptide conjugates

| Antibody | Homologous peptide ELISA reciprocal titer (log$_2$)[a] | Cross-reactivity with rMOMP ELISA (A$_{492}$)[b] |
|---|---|---|
| B5-4 | 9 | 0.02 |
| B5-5 | 11 | 0.00 |
| Anti-rMOMP[d] | n/a | 2.31 |

[a]Serial two-fold dilutions of peptide antisera were made and tested for reactivity to their homologous peptides at 5 μg/ml. Absorbance values were subtracted from background (range 0.05–0.160).
[b]Peptide antisera were diluted 1:1000 and tested for reactivity to recombinant MOMP. Absorbance values (range 0.05–0.160) were subtracted from background.
[c]Groups of 5 mice were immunized for each peptide conjugate. The data shown represent mice with the highest antibody titer.
[d]Anti-rMOMP sera was obtained from mice immunized with recombinant MOMP and tested at 1:1000 for reactivity to relevant antigen at 5 μg/ml.

Dot-Blot Analyses

Figure 14:
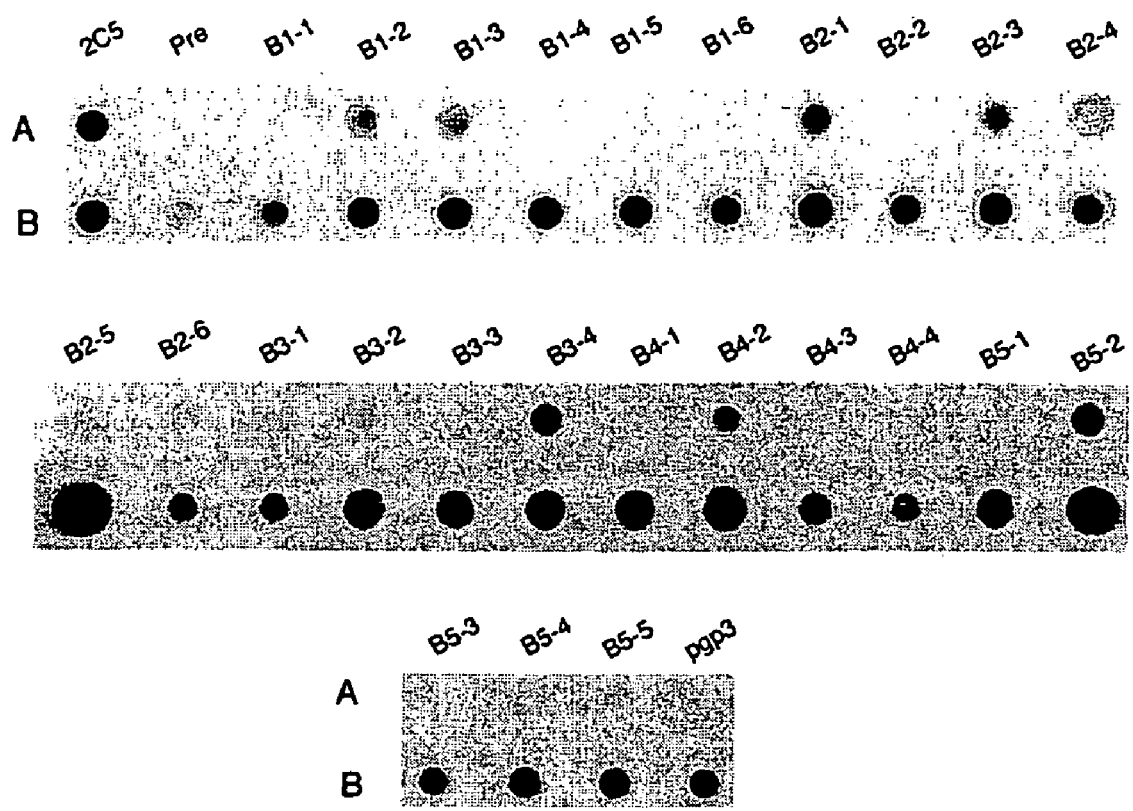
FIG. 14 is an image of a dot-blot analysis to determine the specificity and surface reactivity of PorB peptide antisera. Peptide-specific antisera were used to probe viable (Row A) or SDS-treated (Row B) chlamydial EB immobilized on a nitrocellulose membrane. Peptide antisera and pre-immune negative control sera were tested at a 1:100 dilution. The Pgp3-specific control antisera was used at a 1:500 dilution and the positive control monoclonal to MOMP, 2C5 was tested at a 1:2000 dilution.

To confirm the specificity and surface reactivity of the PorB peptide antisera, a dot-blot analysis was performed with *chlamydial* EB as previously described by Zhang et al. (Zhang, Y. X. et al (1987) J Immunol 138:575-581). Anti-B2-1, B2-3, B3-4 and B5-2 showed the strongest reactivities to *chlamydial* EB, followed by anti-B1-2, B1-3, B2-4 and B4-2 (FIG. 14). This demonstrates that the cognate epitopes for these antibodies are exposed on the bacterial surface.

Epitope B3-2, that showed surface accessibility by the EB-absorption method, did not show a strong signal in the dot-blot assay. In contrast, epitope B4-2 that was not surface-exposed by EB-absorption gave a strong signal by the dot-blot method. The absence of a reactive signal for the remaining PorB peptide antisera implies that their respective epitopes are inaccessible for antibody recognition.

When the EB were treated with SDS, the dot-blot profile for all the peptide antisera was very strong, indicating that SDS had solubilized the outer membrane of the EB and all PorB epitopes were now accessible (FIG. 14). Pre-immune sera were negative for reactivity with both SDS-treated and untreated EB. An additional control was included in which sera to a non-surface protein, Pgp3 (Comanducci, M. et al (1993) J Gen Microbiol 139:1083-1092) was used to probe immobilized EB. This antibody did not bind to the intact EB but showed strong reactivity with lysed EB, verifying the structural integrity of the viable EB. The findings in the dot-blot analyses were consistent with those of the EB-absorption studies and confirmed that the major antigenic determinants of PorB are surface-exposed.

Figure 16:
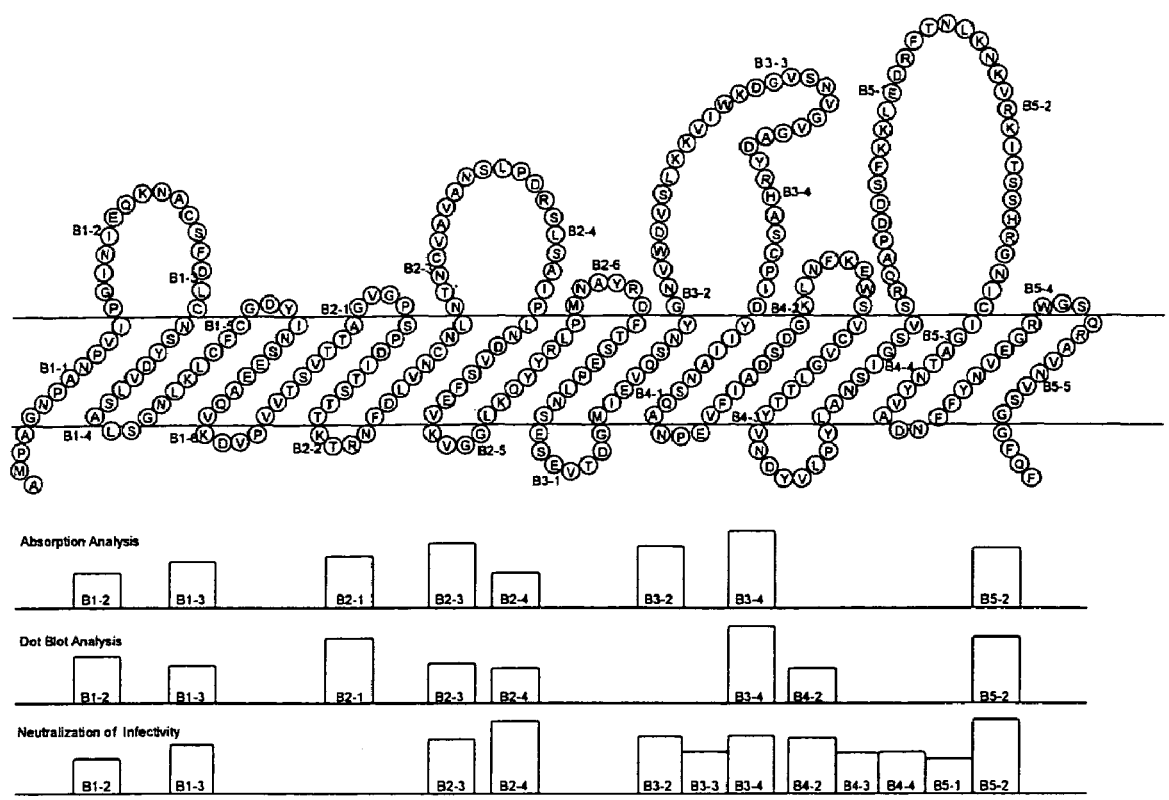

With the exception of two epitopes, the absorption and dot-blot studies with peptide antisera consistently identified the same seven epitopes as surface-exposed (FIG. 16). The discrepancy observed for B3-2 and B4-2 may be attributed to fundamental differences between the ELISA and the dot-blot methods or differences in the peptide-specific antibody populations being recognized. Nevertheless, when polyclonal immune sera from humans and rabbits were used in similar EB-absorption studies, both epitopes were recognized as surface-accessible.

Example 15

In vitro Neutralization of *Chlamydial* Infectivity

Figure 15:
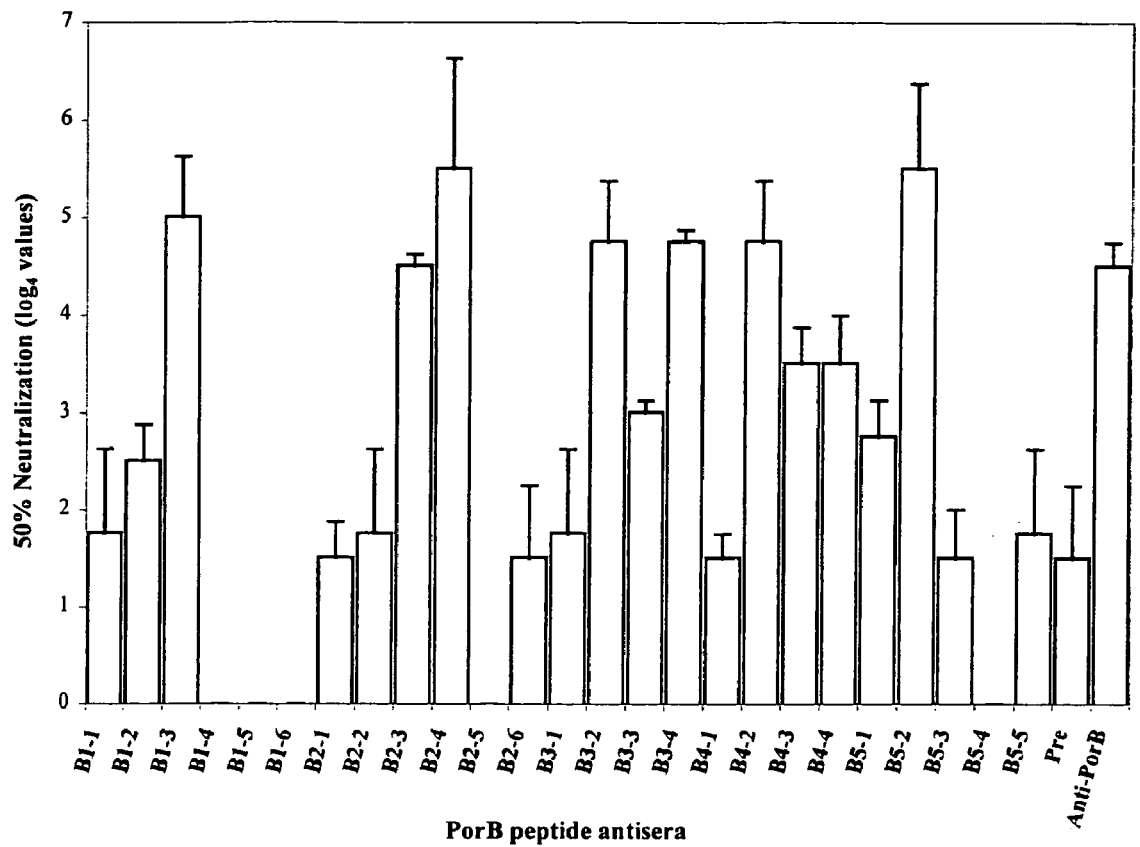
FIG. 15 is a graph showing the results of assays to detect neutralization of infectivity for *C. trachomatis* EB with serial dilutions of PorB peptide antisera. Sera titer representing 50% neutralization of infectivity (±SEM) for *C. trachomatis* EB are shown for the various PorB peptide antisera. EB were incubated with serial dilutions of pe response or reduction of bacterial load). The precise dosage will vary according to a variety of factors such as subject-dependent variables (e.g., age, immune system health, etc.), the disease (e.g., the species of the infecting pathogen), and the treatment being effected. In the case of an intracellular pathogen infection, an "effective amount" is that amount necessary to substantially improve the likelihood of treating the infection, in particular that amount which improves the likelihood of successfully preventing infection or eliminating infection when it has occurred. Thus, for example, a therapeutic immune response is one that facilitates prevention of infection by a *Chlamydial* bacterium and/or facilitates clearance of an infecting *Chlamydia*.

In vitro neutralization assays are a central component in evaluating functionality of *chlamydial* immune responses and provide the best correlate of protective immune responses (Byrne, G. I., R. S. Stephens and et al (1993) *J Infect Dis* 168:415-420). The neutralization data for the peptide antisera revealed four regions of neutralizing activity on the PorB protein with 50% reciprocal neutralization end-point titers ranging from about 32 to about 2048 (FIG. 15). Anti-B1-3, B2-4 and B5-2 sera provided the strongest neutralization activities with 50% reciprocal end-point titers >1024 followed by anti-B2-3, B3-2, B3-4 and B4-2. Notably, these regions of neutralizing activity overlap regions identified as immunoreactive and surface-exposed by ELISA and dot-blot analysis. This confirms that the epitopes contributing to the neutralizing property of PorB antisera are surface-exposed.

When a pool of peptides representing the strongly neutralizing epitopes (B1-3, B2-3 B2-4, B3-2, B3-4 B4-2 and B5-2) was used in a competitive inhibition assay with PorB antisera, the neutralizing ability of PorB antisera was markedly reduced (Table 4). Inhibition of neutralization was concentration-dependent with 10 μg of peptides completely blocking neutralization. Similarly, pre-incubation of the PorB antisera with purified recombinant PorB also ablated neutralization of *chlamydial* infectivity. Heat-denaturation of PorB appeared to have no additional effect on inhibiting PorB antisera since the neutralization results were similar to that observed when intact PorB was used as the inhibiting antigen. These results revealed that neutralizing PorB antisera contain a population of antibodies that recognize predominantly linear epitopes on the surface of the EB.

TABLE 4

Percent Neutralization of chlamydial infectivity by PorB
antisera in the presence of inhibitory antigen

| | Concentration (μg)[a] | | |
|---|---|---|---|
| Antigen | 2 | 5 | 10 |
| Peptides[b] | 28%[c] | 0% | 0% |
| PorB | 39% | 11% | 0% |
| Denatured PorB[d] | 39% | 6% | 11% |

[a]Increasing concentrations of inhibiting antigen were pre-incubated with a dilution of PorB antisera yielding ~60% neutralization and used in in vitro neutralization assays as described in the methods section.
[b]A pool of synthetic peptides representing epitopes that are neutralizing targets were used for inhibition studies.
[c]% Neutralization was calculated for each sample relative to the SPG control. Assay was done in triplicate.
[d]Purified PorB protein was denatured by boiling for 10 minutes.

The neutralization profile developed with PorB peptide antisera reveals four major regions of neutralizing activity that overlap the regions identified as immunoreactive and surface-exposed (FIG. 16). The proximity of the neutralizing epitopes supports the existence of a complex of discontinuous antigenic structures that contribute to the PorB-specific neutralizing immune response. Since antibodies raised to synthetic peptides may be limited in their recognition of linear versus conformational epitopes on the native antigen, caution must be exercised in interpreting the PorB neutralization data. Although the complex of discontinuous antigenic structures as defined by the peptide-specific antisera does not exclude the presence of conformational epitopes, evidence provided in this study that the neutralizing activity of PorB antisera is ablated by synthetic PorB peptides or purified PorB suggests the presence of a large population of PorB antibodies whose neutralizing activity is independent of conformational requirements.

Example 16

Identification of Common PorB Epitopes Between
C. trachomatis and C. pneumoniae

Comparison of the PorB amino acid sequence for *C. trachomatis* and C. pneumoniae revealed 59.3% identity, indicating that this protein is conserved between species (Kubo and Stephens (2000) *Mol Microbiol* 38:772-780). In order to determine whether the neutralizing *C. trachomatis* PorB peptide antisera recognized common epitopes between the two species, the reactivity of the neutralizing PorB peptide antisera to analogous synthetic C. pneumoniae PorB peptides was evaluated. Four C. pneumoniae PorB peptides (Cpn 1-3, Cpn 3-2, Cpn 4-4 and Cpn 5-2) showed strong reactivities to the corresponding *C. trachomatis* peptide antisera (Table. 5). Amino-acid sequence comparison revealed that *C. pneumoniae* PorB peptides with the highest cross-reactivity (Cpn 3-2, Cpn 4-4 and Cpn 5-2) shared a minimum of 67% residue identity (bold) and 75% sequence similarity with their corresponding *C. trachomatis* PorB peptides. In contrast peptides with less than 50% sequence identity (Cpn1-2, Cpn2-3, Cpn2-4) showed little or no cross-reactivity with the corresponding peptide antisera.

Antibody recognition of Cpn PorB epitopes was not always associated with an increased number of shared or similar residues. For instance, Cpn 4-3 which has 60% identity and 90% similarity with B4-3 showed no reactivity with the corresponding B4-3 antisera, whereas, Cpn2-4 with 40% identity and only 50% similarity showed moderate cross-reactivity. The reactivity patterns suggest that these *C. pneumoniae* epitopes may be surface exposed and may also be the targets of neutralizing antibody responses. Collectively, these results show that neutralizing PorB peptide antisera recognize similar PorB epitopes in *C. trachomatis* and *C. pneumoniae* and suggest that the sera may have broad neutralizing properties directed against surface-exposed epitopes.

Identification of the major neutralizing epitopes for PorB has important implications for *chlamydial* vaccine design. In addition to having surface-accessible and possibly conformation-independent antigenic determinants, a major advantage of PorB is that it is highly sequence conserved between serovars and species (Kubo and Stephens (2000) *Mol Microbiol* 38:772-780) and can be expected to provide protection for a broad spectrum of *chlamydial* strains including *C. pneamoniae*. Consistent with this, is the finding that neutralizing antibodies to *C. trachomatis* serovar D PorB epitopes cross-react with analogous *C. pneumoniae* peptides and also neutralize infectivity of *C. trachomatis* serovar B (data not shown). Moreover, the *C. pneumoniae* PorB peptides used in this study have similar hydrophilicity profiles as their *C. trachomatis* counterparts, increasing the likelihood that these epitopes are also surface oriented on the native antigen and are targets of a broadly neutralizing antibody response. PorB as a vaccine antigen will obviate the need to incorporate serovar and species-specific determinants and if effective, will be valuable in providing protection against multiple serovars or species, which is highly desirable for long-term control of *chlamydial* infections.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

TABLE 5

Reactivity of neutralizing *C. trachomatis* PorB peptide-specific antisera to synthetic *C. pneumoniae* PorB peptides

| Peptide | Amino-acid sequence[a] | | Reactivity to peptide antisera ELISA ($A_{492}$)[b] |
|---|---|---|---|
| Cpn 1-2 | APVLPGVNPEQTGWCA | (SEQ ID NO.36) | 0.10 |
| Cpn 1-3 | QTGWCAFQLCNSYDLF | (SEQ ID NO.37) | 1.24 |
| Cpn 2-3 | DLNNSSISSSCVFATIALQE | (SEQ ID NO.38) | 0.49 |
| Cpn 2-4 | TIALQETSPAAIPLLDIAFT | (SEQ ID NO.39) | 0.58 |
| Cpn 3-2 | GLIEVQSDYGIVWGLSLQKV | (SEQ ID NO.40) | 2.76 |
| Cpn 3-3 | GLSLQKVLWKDGSFVGVSAD | (SEQ ID NO.41) | 0.19 |
| Cpn 3-4 | FVGVSADYRHGSSPINYIIV | (SEQ ID NO.42) | 0.50 |
| Cpn 4-2 | IYFDATDGNLSYKEWSASIG | (SEQ ID NO.43) | 0.82 |
| Cpn 4-3 | WSASIGISTYLNDYVLPYAS | (SEQ ID NO.44) | 0.12 |
| Cpn 4-4 | VLPYASVSIGNTSRKAPSDSF | (SEQ ID NO.45) | 3.00 |
| Cpn 5-2 | FTNFKFKIRKITNFDRVN | (SEQ ID NO.46) | 2.08 |

[a]Synthetic peptides analogous to *C. trachomatis* PorB peptides were synthesized as described in the methods section. Residues are listed in single-letter code beginning at the N-terminal end. Regions of shared amino-acid sequences are in bold and underlined.
[b]Peptide-specific antisera were diluted 1:1000 and tested for reactivity to *C. pneumoniae* PorB peptides at 5 μg/ml. Absorbance values at 492 nm were compared to values for reactivity of antisera to cognate *C. trachomatis* peptides.

That which is claimed is:

1. An isolated nucleic acid comprising a nucleic acid sequence encoding a *C. pneumoniae* PorB polypeptide up to 60 amino acids in length wherein the polypeptide contains an amino acid sequence that is at least 67% identical to the amino acid sequence FTNLKFKVRKITSSHRGN (SEQ ID NO: 20), wherein the polypeptide binds to neutralizing *C. trachomatis* PorB polypeptide-specific antisera.

2. The isolated nucleic acid of claim 1, wherein the polypeptide has the amino acid sequence of FTNLKFKVR-KITSSHRGN (SEQ ID NO: 20).

3. The isolated nucleic acid of claim 1, wherein the polypeptide has the amino acid sequence of VLPYLAF-SIGSVSRQAPDDSFKKLEDRFTNLK-FKVRKITSSHRGN (SEQ ID NO: 10).

4. The isolated nucleic acid of claim 1, wherein the polypeptide comprises at least 30 amino acids.

5. The isolated nucleic acid of claim 1, wherein the polypeptide comprises at least 20 amino acids.

6. The isolated nucleic acid of claim 1, wherein the polypeptide comprises at least 15 amino acids.

7. The isolated nucleic acid of claim 1, wherein the polypeptide has the amino acid sequence of FTNFKFKIR-KITNFDRVN (SEQ ID NO: 46).

8. An isolated nucleic acid comprising a nucleic acid sequence encoding a *C. pneumoniae* PorB polypeptide up to 60 amino acids in length having the amino acid sequence of FTNLKFKVRKITSSHRGN (SEQ ID NO: 20).

9. The isolated nucleic acid of claim 8, wherein the polypeptide has the amino acid sequence of FTNLKFKVR-KITSSHRGN (SEQ ID NO: 20).

10. The isolated nucleic acid of claim 8, wherein the polypeptide has the amino acid sequence of VLPYLAF-SIGSVSRQAPDDSFKKLEDRFTNLK-FKVRKITSSHRGN (SEQ ID NO: 10).

11. The isolated nucleic acid of claim 8, wherein the polypeptide comprises at least 30 amino acids.

12. The isolated nucleic acid of claim 8, wherein the polypeptide comprises at least 20 amino acids.

* * * * *

UNITED STATES PATENT AND TRADEMARK OFFICE
CERTIFICATE OF CORRECTION

| | |
|---|---|
| PATENT NO. | : 7,253,275 B2 |
| APPLICATION NO. | : 11/414278 |
| DATED | : August 7, 2007 |
| INVENTOR(S) | : Richard S. Stephens |

It is certified that error appears in the above-identified patent and that said Letters Patent is hereby corrected as shown below:

In Column 1 line 16: Delete "may have" and replace with "has".

Signed and Sealed this

Fifth Day of May, 2009

JOHN DOLL
*Acting Director of the United States Patent and Trademark Office*

SEQUENCE LISTING

<160> NUMBER OF SEQ ID NOS: 47

<210> SEQ ID NO 1
<211> LENGTH: 1023
<212> TYPE: DNA
<213> ORGANISM: C. trachomatis
<220> FEATURE:
<221> NAME/KEY: CDS
<222> LOCATION: (1)...(1020)

<400> SEQUENCE: 1

```
atg agt agc aag cta gtg aac tat ctc cgt ttg act ttc cta tct ttt      48
Met Ser Ser Lys Leu Val Asn Tyr Leu Arg Leu Thr Phe Leu Ser Phe
1               5                   10                  15 tta ggg atc gca tct act tca tta gac gct atg cct gcg ggg aat ccg      96
Leu Gly Ile Ala Ser Thr Ser Leu Asp Ala Met Pro Ala Gly Asn Pro
            20                  25                  30 gcg ttt cca gtc atc ccg ggg att aat att gaa cag aaa aat gcc tgt     144
Ala Phe Pro Val Ile Pro Gly Ile Asn Ile Glu Gln Lys Asn Ala Cys
        35                  40                  45 tct ttc gat tta tgt aat tct tat gat gta cta tcc gca ctg tcc ggt     192
Ser Phe Asp Leu Cys Asn Ser Tyr Asp Val Leu Ser Ala Leu Ser Gly
    50                  55                  60 aac ctg aag ctc tgc ttc tgc gga gat tat atc ttt tca gaa gaa gct     240
Asn Leu Lys Leu Cys Phe Cys Gly Asp Tyr Ile Phe Ser Glu Glu Ala
65                  70                  75                  80 cag gta aaa gat gtc cct gtc gtt acc tct gtg aca aca gct ggg gtt     288
Gln Val Lys Asp Val Pro Val Val Thr Ser Val Thr Thr Ala Gly Val
                85                  90                  95 ggt cct tct cct gat att act tcg aca acc aaa acg cga aat ttc gat     336
Gly Pro Ser Pro Asp Ile Thr Ser Thr Thr Lys Thr Arg Asn Phe Asp
            100                 105                 110 ctc gtg aac tgt aat ctc aat aca aac tgt gta gct gta gct ttt tcc     384
Leu Val Asn Cys Asn Leu Asn Thr Asn Cys Val Ala Val Ala Phe Ser
        115                 120                 125 ctt cct gat cgt tcg ctg agc gcg att cct ctg ttt gat gtg agt ttc     432
Leu Pro Asp Arg Ser Leu Ser Ala Ile Pro Leu Phe Asp Val Ser Phe
    130                 135                 140 gaa gtg aaa gta gga gga ctg aaa caa tac tac cgc ctt ccc atg aat     480
Glu Val Lys Val Gly Gly Leu Lys Gln Tyr Tyr Arg Leu Pro Met Asn
145                 150                 155                 160 gcc tat cga gac ttc acc tcg gaa cct ctc aat tct gaa tca gaa gtt     528
Ala Tyr Arg Asp Phe Thr Ser Glu Pro Leu Asn Ser Glu Ser Glu Val
                165                 170                 175 acg gac ggg atg att gaa gta cag tcc aat tac gga ttt gtt tgg gat     576
Thr Asp Gly Met Ile Glu Val Gln Ser Asn Tyr Gly Phe Val Trp Asp
            180                 185                 190 gtt agc ttg aaa aaa gtc ata tgg aaa gat ggc gtt tcc ttt gta ggc     624
Val Ser Leu Lys Lys Val Ile Trp Lys Asp Gly Val Ser Phe Val Gly
        195                 200                 205 gtc ggt gca gac tat cgc cat gct tct tgc cct att gac tac atc att     672
Val Gly Ala Asp Tyr Arg His Ala Ser Cys Pro Ile Asp Tyr Ile Ile
    210                 215                 220 gca aac agt caa gct aat cca gaa gta ttc atc gct gac tcg gat ggg     720
Ala Asn Ser Gln Ala Asn Pro Glu Val Phe Ile Ala Asp Ser Asp Gly
225                 230                 235                 240 aaa ctg aac ttc aag gag tgg agt gtc tgc gta ggt ctt act acc tat     768
Lys Leu Asn Phe Lys Glu Trp Ser Val Cys Val Gly Leu Thr Thr Tyr
                245                 250                 255
```

-continued

```
gtg aat gac tac gtt ctt cct tac tta gcg ttt tct ata ggg agt gtt         816
Val Asn Asp Tyr Val Leu Pro Tyr Leu Ala Phe Ser Ile Gly Ser Val
            260                 265                 270 tct cgc caa gct ccg gac gac agc ttc aaa aaa tta gaa gat cgc ttc         864
Ser Arg Gln Ala Pro Asp Asp Ser Phe Lys Lys Leu Glu Asp Arg Phe
        275                 280                 285 act aac ctc aaa ttt aaa gtt cgt aaa att acc agc tct cat cgt gga         912
Thr Asn Leu Lys Phe Lys Val Arg Lys Ile Thr Ser Ser His Arg Gly
    290                 295                 300 aac atc tgc atc gga gcg aca aac tat gtc gcc gat aac ttc ttc tac         960
Asn Ile Cys Ile Gly Ala Thr Asn Tyr Val Ala Asp Asn Phe Phe Tyr
305                 310                 315                 320 aac gta gaa gga aga tgg gga agc cag cgc gct gtg aac gtc tcc gga        1008
Asn Val Glu Gly Arg Trp Gly Ser Gln Arg Ala Val Asn Val Ser Gly
                325                 330                 335 gga ttc caa ttc taa                                                    1023
Gly Phe Gln Phe
            340
```

<210> SEQ ID NO 2
<211> LENGTH: 340
<212> TYPE: PRT
<213> ORGANISM: C. trachomatis

<400> SEQUENCE: 2

```
Met Ser Ser Lys Leu Val Asn Tyr Leu Arg Leu Thr Phe Leu Ser Phe
1               5                   10                  15

Leu Gly Ile Ala Ser Thr Ser Leu Asp Ala Met Pro Ala Gly Asn Pro
            20                  25                  30

Ala Phe Pro Val Ile Pro Gly Ile Asn Ile Glu Gln Lys Asn Ala Cys
        35                  40                  45

Ser Phe Asp Leu Cys Asn Ser Tyr Asp Val Leu Ser Ala Leu Ser Gly
    50                  55                  60

Asn Leu Lys Leu Cys Phe Cys Gly Asp Tyr Ile Phe Ser Glu Glu Ala
65                  70                  75                  80

Gln Val Lys Asp Val Pro Val Val Thr Ser Val Thr Thr Ala Gly Val
                85                  90                  95

Gly Pro Ser Pro Asp Ile Thr Ser Thr Thr Lys Thr Arg Asn Phe Asp
            100                 105                 110

Leu Val Asn Cys Asn Leu Asn Thr Asn Cys Val Ala Val Ala Phe Ser
        115                 120                 125

Leu Pro Asp Arg Ser Leu Ser Ala Ile Pro Leu Phe Asp Val Ser Phe
    130                 135                 140

Glu Val Lys Val Gly Gly Leu Lys Gln Tyr Tyr Arg Leu Pro Met Asn
145                 150                 155                 160

Ala Tyr Arg Asp Phe Thr Ser Glu Pro Leu Asn Ser Glu Ser Glu Val
                165                 170                 175

Thr Asp Gly Met Ile Glu Val Gln Ser Asn Tyr Gly Phe Val Trp Asp
            180                 185                 190

Val Ser Leu Lys Lys Val Ile Trp Lys Asp Gly Val Ser Phe Val Gly
        195                 200                 205

Val Gly Ala Asp Tyr Arg His Ala Ser Cys Pro Ile Asp Tyr Ile Ile
    210                 215                 220

Ala Asn Ser Gln Ala Asn Pro Glu Val Phe Ile Ala Asp Ser Asp Gly
225                 230                 235                 240

Lys Leu Asn Phe Lys Glu Trp Ser Val Cys Val Gly Leu Thr Thr Tyr
                245                 250                 255
```

-continued

Val Asn Asp Tyr Val Leu Pro Tyr Leu Ala Phe Ser Ile Gly Ser Val
            260                 265                 270

Ser Arg Gln Ala Pro Asp Ser Phe Lys Lys Leu Glu Asp Arg Phe
        275                 280                 285

Thr Asn Leu Lys Phe Lys Val Arg Lys Ile Thr Ser Ser His Arg Gly
            290                 295                 300

Asn Ile Cys Ile Gly Ala Thr Asn Tyr Val Ala Asp Asn Phe Phe Tyr
305                 310                 315                 320

Asn Val Glu Gly Arg Trp Gly Ser Gln Arg Ala Val Asn Val Ser Gly
                325                 330                 335

Gly Phe Gln Phe
        340

<210> SEQ ID NO 3
<211> LENGTH: 393
<212> TYPE: PRT
<213> ORGANISM: C. trachomatis

<400> SEQUENCE: 3

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Ala Thr Trp Cys Asp Ala Ile Ser Met Arg Val Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Lys Pro Thr Thr Asp Thr Gly Asn Ser Ala
                85                  90                  95

Ala Pro Ser Thr Leu Thr Ala Arg Glu Asn Pro Ala Tyr Gly Arg His
            100                 105                 110

Met Gln Asp Ala Glu Met Phe Thr Asn Ala Ala Cys Met Ala Leu Asn
        115                 120                 125

Ile Trp Asp Arg Phe Asp Val Phe Cys Thr Leu Gly Ala Thr Ser Gly
    130                 135                 140

Tyr Leu Lys Gly Asn Ser Ala Ser Phe Asn Leu Val Gly Leu Phe Gly
145                 150                 155                 160

Asp Asn Glu Asn Gln Lys Thr Val Lys Ala Glu Ser Val Pro Asn Met
                165                 170                 175

Ser Phe Asp Gln Ser Val Val Glu Leu Tyr Thr Asp Thr Thr Phe Ala
            180                 185                 190

Trp Ser Val Gly Ala Arg Ala Ala Leu Trp Glu Cys Gly Cys Ala Thr
        195                 200                 205

Leu Gly Ala Ser Phe Gln Tyr Ala Gln Ser Lys Pro Lys Val Glu Glu
    210                 215                 220

Leu Asn Val Leu Cys Asn Ala Ala Glu Phe Thr Ile Asn Lys Pro Lys
225                 230                 235                 240

Gly Tyr Val Gly Lys Glu Phe Pro Leu Asp Leu Thr Ala Gly Thr Asp
                245                 250                 255

Ala Ala Thr Gly Thr Lys Asp Ala Ser Ile Asp Tyr His Glu Trp Gln
            260                 265                 270

Ala Ser Leu Ala Leu Ser Tyr Arg Leu Asn Met Phe Thr Pro Tyr Ile

-continued

```
                275                 280                 285
Gly Val Lys Trp Ser Arg Ala Ser Phe Asp Ala Asp Thr Ile Arg Ile
            290                 295                 300
Ala Gln Pro Lys Ser Ala Thr Ala Ile Phe Asp Thr Thr Thr Leu Asn
305                 310                 315                 320
Pro Thr Ile Ala Gly Ala Gly Asp Val Lys Thr Gly Ala Glu Gly Gln
                325                 330                 335
Leu Gly Asp Thr Met Gln Ile Val Ser Leu Gln Leu Asn Lys Met Lys
            340                 345                 350
Ser Arg Lys Ser Cys Gly Ile Ala Val Gly Thr Thr Ile Val Asp Ala
            355                 360                 365
Asp Lys Tyr Ala Val Thr Val Glu Thr Arg Leu Ile Asp Glu Arg Ala
370                 375                 380
Ala His Val Asn Ala Gln Phe Arg Phe
385                 390

<210> SEQ ID NO 4
<211> LENGTH: 345
<212> TYPE: PRT
<213> ORGANISM: C.  pneumonia

<400> SEQUENCE: 4

Met Asn Ser Lys Met Leu Lys His Leu Arg Leu Ala Thr Leu Ser Phe
1               5                   10                  15
Ser Met Phe Phe Gly Ile Val Ser Pro Ala Val Tyr Ala Leu Gly
            20                  25                  30
Ala Gly Asn Pro Ala Ala Pro Val Leu Pro Gly Val Asn Pro Glu Gln
            35                  40                  45
Thr Gly Trp Cys Ala Phe Gln Leu Cys Asn Ser Tyr Asp Leu Phe Ala
    50                  55                  60
Ala Leu Ala Gly Ser Leu Lys Phe Gly Phe Tyr Gly Asp Tyr Val Phe
65                  70                  75                  80
Ser Glu Ser Ala His Ile Thr Asn Val Pro Val Ile Thr Ser Val Thr
                85                  90                  95
Thr Ser Gly Thr Gly Thr Thr Pro Thr Ile Thr Ser Thr Thr Lys Asn
            100                 105                 110
Val Asp Phe Asp Leu Asn Asn Ser Ser Ile Ser Ser Ser Cys Val Phe
        115                 120                 125
Ala Thr Ile Ala Leu Gln Glu Thr Ser Pro Ala Ala Ile Pro Leu Leu
    130                 135                 140
Asp Ile Ala Phe Thr Ala Arg Val Gly Gly Leu Lys Gln Tyr Tyr Arg
145                 150                 155                 160
Leu Leu Pro Leu Asn Ala Tyr Arg Asp Phe Thr Ser Asn Pro Leu Asn
                165                 170                 175
Ala Glu Ser Glu Val Thr Asp Gly Leu Ile Glu Val Gln Ser Asp Tyr
            180                 185                 190
Gly Ile Val Trp Gly Leu Ser Leu Gln Lys Val Leu Trp Lys Asp Gly
        195                 200                 205
Val Ser Phe Val Gly Val Ser Ala Asp Tyr Arg His Gly Ser Ser Pro
    210                 215                 220
Ile Asn Tyr Ile Ile Val Tyr Val Lys Ala Asn Pro Glu Ile Tyr Phe
225                 230                 235                 240
Asp Ala Thr Asp Gly Asn Leu Ser Tyr Lys Glu Trp Ser Ala Ser Ile
                245                 250                 255
```

```
Gly Ile Ser Thr Tyr Leu Asn Asp Tyr Val Leu Pro Tyr Ala Ser Val
            260                 265                 270

Ser Ile Gly Asn Thr Ser Arg Lys Ala Pro Ser Asp Ser Phe Thr Glu
            275                 280                 285

Leu Glu Lys Trp Phe Thr Asn Phe Lys Phe Lys Ile Arg Lys Ile Thr
            290                 295                 300

Asn Phe Asp Arg Val Asn Phe Cys Phe Gly Thr Thr Cys Cys Ile Ser
305                 310                 315                 320

Asn Asn Phe Tyr Tyr Ser Val Glu Gly Arg Trp Gly Tyr Gln Arg Ala
                325                 330                 335

Ile Asn Ile Thr Ser Gly Leu Gln Phe
            340                 345

<210> SEQ ID NO 5
<211> LENGTH: 340
<212> TYPE: PRT
<213> ORGANISM: C. trachomatis (L2)

<400> SEQUENCE: 5

Met Ser Ser Lys Leu Val Asn Tyr Leu Arg Leu Thr Phe Leu Ser Phe
1               5                   10                  15

Leu Gly Ile Ala Ser Thr Ser Leu Asp Ala Met Pro Ala Gly Asn Pro
            20                  25                  30

Ala Phe Pro Val Ile Pro Gly Ile Asn Ile Glu Gln Lys Asn Ala Cys
            35                  40                  45

Ser Phe Asp Leu Cys Asn Ser Tyr Asp Val Leu Ser Ala Leu Ser Gly
        50                  55                  60

Asn Leu Lys Leu Cys Phe Phe Gly Asp Tyr Ile Phe Ser Glu Ala
65                  70                  75                  80

Gln Val Lys Asp Val Pro Val Val Thr Ser Val Thr Thr Cys Gly Ile
                85                  90                  95

Gly Pro Ser Pro Asn Ile Thr Ser Thr Lys Thr Arg Asn Phe Asp
            100                 105                 110

Leu Val Asn Cys Asn Leu Asn Glx Asn Cys Ala Ala Val Ala Phe Ser
            115                 120                 125

Leu Pro Asp Arg Ser Leu Ser Ala Ile Pro Leu Phe Asp Val Ser Phe
130                 135                 140

Glu Val Lys Val Gly Gly Leu Lys Gln Tyr Tyr Arg Leu Pro Met Asn
145                 150                 155                 160

Ala Tyr Arg Asp Phe Thr Ser Glu Pro Leu Asn Ser Glu Ser Glu Val
                165                 170                 175

Thr Asp Gly Met Ile Glu Val Gln Ser Asn Tyr Gly Phe Val Trp Asp
            180                 185                 190

Val Ser Leu Lys Lys Val Ile Trp Lys Asp Gly Val Ser Phe Val Gly
            195                 200                 205

Val Gly Ala Asp Tyr Arg His Ala Ser Cys Pro Ile Asp Tyr Ile Ile
            210                 215                 220

Ala Asn Ser Gln Ala Asn Pro Glu Val Phe Ile Ala Asp Ser Asp Gly
225                 230                 235                 240

Lys Leu Asn Phe Lys Glu Trp Ser Val Cys Val Gly Leu Thr Thr Tyr
                245                 250                 255

Val Asn Asp Tyr Val Leu Pro Tyr Leu Ala Phe Ser Ile Gly Ser Val
            260                 265                 270

Ser Arg Gln Ala Pro Asp Asp Ser Phe Lys Lys Leu Glu Asp Arg Phe
            275                 280                 285
```

```
Thr Asn Leu Lys Phe Lys Val Arg Lys Ile Thr Ser Ser His Arg Gly
        290                 295                 300

Asn Ile Cys Ile Gly Ala Thr Asn Tyr Ile Ala Asp Asn Phe Phe Tyr
305                 310                 315                 320

Asn Val Glu Gly Arg Trp Gly Ser Gln Arg Ala Val Asn Val Ser Gly
                325                 330                 335

Gly Phe Gln Phe
            340

<210> SEQ ID NO 6
<211> LENGTH: 340
<212> TYPE: PRT
<213> ORGANISM: C. trachomatis (C)

<400> SEQUENCE: 6

Met Ser Ser Lys Leu Val Asn Tyr Leu Arg Leu Thr Phe Leu Ser Phe
1               5                   10                  15

Leu Gly Ile Ala Ser Thr Ser Leu Asp Ala Met Pro Ala Gly Asn Pro
            20                  25                  30

Ala Phe Pro Val Ile Pro Gly Ile Asn Ile Glu Gln Lys Asn Ala Cys
        35                  40                  45

Ser Phe Asp Leu Cys Asn Ser Tyr Asp Val Leu Ser Ala Leu Ser Gly
    50                  55                  60

Asn Leu Lys Leu Cys Phe Cys Gly Asp Tyr Ile Phe Ser Glu Glu Ala
65                  70                  75                  80

Gln Val Lys Asp Val Pro Val Val Thr Ser Met Thr Thr Ala Gly Val
                85                  90                  95

Gly Pro Ser Pro Asp Ile Thr Ser Thr Thr Lys Thr Arg Asn Phe Asp
            100                 105                 110

Leu Val Asn Cys Asn Leu Asn Thr Asn Cys Val Ala Val Ala Phe Ser
        115                 120                 125

Leu Pro Asp Arg Ser Leu Ser Ala Ile Pro Leu Phe Asp Val Ser Phe
    130                 135                 140

Glu Val Lys Val Gly Gly Leu Lys Gln Tyr Tyr Arg Leu Pro Met Asn
145                 150                 155                 160

Ala Tyr Arg Asp Phe Thr Ser Glu Pro Leu Asn Ser Glu Ser Glu Val
                165                 170                 175

Thr Asp Gly Met Ile Glu Val Gln Ser Asn Tyr Gly Phe Val Trp Asp
            180                 185                 190

Val Ser Leu Lys Lys Val Ile Trp Lys Asp Gly Val Ser Phe Val Gly
        195                 200                 205

Val Gly Ala Asp Tyr Arg His Ala Ser Cys Pro Ile Asp Tyr Ile Ile
    210                 215                 220

Ala Asn Ser Gln Ala Asn Pro Glu Val Phe Ile Ala Asp Ser Asp Gly
225                 230                 235                 240

Lys Leu Asn Phe Lys Glu Trp Ser Val Cys Val Gly Leu Thr Thr Tyr
                245                 250                 255

Val Asn Asp Tyr Val Leu Pro Tyr Leu Ala Phe Ser Ile Gly Ser Val
            260                 265                 270

Ser Arg Gln Ala Pro Asp Asp Ser Phe Lys Lys Leu Glu Asp Arg Phe
        275                 280                 285

Thr Asn Leu Lys Phe Lys Val Arg Lys Ile Thr Ser Ser His Arg Gly
    290                 295                 300

Asn Ile Cys Ile Gly Ala Thr Asn Tyr Ile Ala Asp Asn Phe Phe Tyr
```

```
                305                 310                 315                 320
Asn Val Glu Gly Arg Trp Gly Ser Gln Arg Ala Val Asn Val Ser Gly
                325                 330                 335

Gly Phe Gln Phe
            340

<210> SEQ ID NO 7
<211> LENGTH: 26
<212> TYPE: PRT
<213> ORGANISM: Chlamydia trachomatis

<400> SEQUENCE: 7

Phe Pro Val Ile Pro Gly Ile Asn Ile Glu Gln Lys Asn Ala Cys Ser
  1               5                  10                  15

Phe Asp Leu Cys Asn Ser Tyr Asp Val Leu
            20                  25

<210> SEQ ID NO 8
<211> LENGTH: 34
<212> TYPE: PRT
<213> ORGANISM: Chlamydia trachomatis

<400> SEQUENCE: 8

Asp Leu Val Asn Cys Asn Leu Asn Thr Asn Cys Val Ala Val Ala Phe
  1               5                  10                  15

Ser Leu Pro Asp Arg Ser Leu Ser Ala Ile Pro Leu Phe Asp Val Ser
            20                  25                  30

Phe Glu

<210> SEQ ID NO 9
<211> LENGTH: 47
<212> TYPE: PRT
<213> ORGANISM: Chlamydia trachomatis

<400> SEQUENCE: 9

Gly Met Ile Glu Val Gln Ser Asn Tyr Gly Phe Val Trp Asp Val Ser
  1               5                  10                  15

Leu Lys Lys Val Ile Trp Lys Asp Gly Val Ser Phe Val Gly Val Gly
            20                  25                  30

Ala Asp Tyr Arg His Ala Ser Cys Pro Ile Asp Tyr Ile Ile Ala
            35                  40                  45

<210> SEQ ID NO 10
<211> LENGTH: 45
<212> TYPE: PRT
<213> ORGANISM: Chlamydia trachomatis

<400> SEQUENCE: 10

Val Leu Pro Tyr Leu Ala Phe Ser Ile Gly Ser Val Ser Arg Gln Ala
  1               5                  10                  15

Pro Asp Asp Ser Phe Lys Lys Leu Glu Asp Arg Phe Thr Asn Leu Lys
            20                  25                  30

Phe Lys Val Arg Lys Ile Thr Ser Ser His Arg Gly Asn
            35                  40                  45

<210> SEQ ID NO 11
<211> LENGTH: 16
<212> TYPE: PRT
<213> ORGANISM: Artificial Sequence
<220> FEATURE:
<223> OTHER INFORMATION: synthetic peptide
```

```
<400> SEQUENCE: 11

Phe Pro Val Ile Pro Gly Ile Asn Ile Glu Gln Lys Asn Ala Cys Ser
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: synthetic peptide

<400> SEQUENCE: 12

Gln Lys Asn Ala Cys Ser Phe Asp Leu Cys Asn Ser Tyr Asp Val Leu
1               5                   10                  15

<210> SEQ ID NO 13
<211> LENGTH: 20
<212> TYPE: PRT
<213> ORGANISM: Artificial Sequence
<220> FEATURE:
<223> OTHER INFORMATION: synthetic peptide

<400> SEQUENCE: 13

Asp Leu Val Asn Cys Asn Leu Asn Thr Asn Cys Val Ala Val Ala Phe
1               5                   10                  15

Ser Leu Pro Asp
            20

<210> SEQ ID NO 14
<211> LENGTH: 20
<212> TYPE: PRT
<213> ORGANISM: Artificial Sequence
<220> FEATURE:
<223> OTHER INFORMATION: synthetic peptide

<400> SEQUENCE: 14

Ala Phe Ser Leu Pro Asp Arg Ser Leu Ser Ala Ile Pro Leu Phe Asp
1               5                   10                  15

Val Ser Phe Glu
            20

<210> SEQ ID NO 15
<211> LENGTH: 20
<212> TYPE: PRT
<213> ORGANISM: Artificial Sequence
<220> FEATURE:
<223> OTHER INFORMATION: synthetic peptide

<400> SEQUENCE: 15

Gly Met Ile Glu Val Gln Ser Asn Tyr Gly Phe Val Trp Asp Val Ser
1               5                   10                  15

Leu Lys Lys Val
            20

<210> SEQ ID NO 16
<211> LENGTH: 21
<212> TYPE: PRT
<213> ORGANISM: Artificial Sequence
<220> FEATURE:
<223> OTHER INFORMATION: synthetic peptide

<400> SEQUENCE: 16

Asp Val Ser Leu Lys Lys Val Ile Trp Lys Asp Gly Val Ser Phe Val
1               5                   10                  15
```

```
Gly Val Gly Ala Asp
            20

<210> SEQ ID NO 17
<211> LENGTH: 20
<212> TYPE: PRT
<213> ORGANISM: Artificial Sequence
<220> FEATURE:
<223> OTHER INFORMATION: synthetic peptide

<400> SEQUENCE: 17

Phe Val Gly Val Gly Ala Asp Tyr Arg His Ala Ser Cys Pro Ile Asp
1               5                   10                  15

Tyr Ile Ile Ala
            20

<210> SEQ ID NO 18
<211> LENGTH: 21
<212> TYPE: PRT
<213> ORGANISM: Artificial Sequence
<220> FEATURE:
<223> OTHER INFORMATION: synthetic peptide

<400> SEQUENCE: 18

Val Leu Pro Tyr Leu Ala Phe Ser Ile Gly Ser Val Ser Arg Gln Ala
1               5                   10                  15

Pro Asp Asp Ser Phe
            20

<210> SEQ ID NO 19
<211> LENGTH: 18
<212> TYPE: PRT
<213> ORGANISM: Artificial Sequence
<220> FEATURE:
<223> OTHER INFORMATION: synthetic peptide

<400> SEQUENCE: 19

Ala Pro Asp Asp Ser Phe Lys Lys Leu Glu Asp Arg Phe Thr Asn Leu
1               5                   10                  15

Lys Phe

<210> SEQ ID NO 20
<211> LENGTH: 18
<212> TYPE: PRT
<213> ORGANISM: Artificial Sequence
<220> FEATURE:
<223> OTHER INFORMATION: synthetic peptide

<400> SEQUENCE: 20

Phe Thr Asn Leu Lys Phe Lys Val Arg Lys Ile Thr Ser Ser His Arg
1               5                   10                  15

Gly Asn

<210> SEQ ID NO 21
<211> LENGTH: 16
<212> TYPE: PRT
<213> ORGANISM: Artificial Sequence
<220> FEATURE:
<223> OTHER INFORMATION: synthetic peptide

<400> SEQUENCE: 21

Asn Ser Tyr Asp Val Leu Ser Ala Leu Ser Gly Asn Leu Lys Leu Cys
1               5                   10                  15
```

```
<210> SEQ ID NO 22
<211> LENGTH: 16
<212> TYPE: PRT
<213> ORGANISM: Artificial Sequence
<220> FEATURE:
<223> OTHER INFORMATION: synthetic peptide

<400> SEQUENCE: 22

Gly Asn Leu Lys Leu Cys Phe Cys Gly Asp Tyr Ile Phe Ser Glu Glu
 1               5                  10                  15

<210> SEQ ID NO 23
<211> LENGTH: 16
<212> TYPE: PRT
<213> ORGANISM: Artificial Sequence
<220> FEATURE:
<223> OTHER INFORMATION: synthetic peptide

<400> SEQUENCE: 23

Tyr Ile Phe Ser Glu Glu Ala Gln Val Lys Asp Val Pro Val Val Thr
 1               5                  10                  15

<210> SEQ ID NO 24
<211> LENGTH: 20
<212> TYPE: PRT
<213> ORGANISM: Artificial Sequence
<220> FEATURE:
<223> OTHER INFORMATION: synthetic peptide

<400> SEQUENCE: 24

Asp Val Pro Val Val Thr Ser Val Thr Thr Ala Gly Val Gly Pro Ser
 1               5                  10                  15

Pro Asp Ile Thr
            20

<210> SEQ ID NO 25
<211> LENGTH: 20
<212> TYPE: PRT
<213> ORGANISM: Artificial Sequence
<220> FEATURE:
<223> OTHER INFORMATION: synthetic peptide

<400> SEQUENCE: 25

Pro Ser Pro Asp Ile Thr Ser Thr Thr Lys Thr Arg Asn Phe Asp Leu
 1               5                  10                  15

Val Asn Cys Asn
            20

<210> SEQ ID NO 26
<211> LENGTH: 19
<212> TYPE: PRT
<213> ORGANISM: Artificial Sequence
<220> FEATURE:
<223> OTHER INFORMATION: synthetic peptide

<400> SEQUENCE: 26

Phe Asp Val Ser Phe Glu Val Lys Val Gly Gly Leu Lys Gln Tyr Tyr
 1               5                  10                  15

Arg Leu Pro

<210> SEQ ID NO 27
<211> LENGTH: 20
<212> TYPE: PRT
<213> ORGANISM: Artificial Sequence
<220> FEATURE:
```

<223> OTHER INFORMATION: synthetic peptide

<400> SEQUENCE: 27

Gln Tyr Tyr Arg Leu Pro Met Asn Ala Tyr Arg Asp Phe Thr Ser Glu
1               5                   10                  15

Pro Leu Asn Ser
            20

<210> SEQ ID NO 28
<211> LENGTH: 20
<212> TYPE: PRT
<213> ORGANISM: Artificial Sequence
<220> FEATURE:
<223> OTHER INFORMATION: synthetic peptide

<400> SEQUENCE: 28

Thr Ser Glu Pro Leu Asn Ser Glu Ser Glu Val Thr Asp Gly Met Ile
1               5                   10                  15

Glu Val Gln Ser
            20

<210> SEQ ID NO 29
<211> LENGTH: 20
<212> TYPE: PRT
<213> ORGANISM: Artificial Sequence
<220> FEATURE:
<223> OTHER INFORMATION: synthetic peptide

<400> SEQUENCE: 29

Pro Ile Asp Tyr Ile Ile Ala Asn Ser Gln Ala Asn Pro Glu Val Phe
1               5                   10                  15

Ile Ala Asp Ser
            20

<210> SEQ ID NO 30
<211> LENGTH: 20
<212> TYPE: PRT
<213> ORGANISM: Artificial Sequence
<220> FEATURE:
<223> OTHER INFORMATION: synthetic peptide

<400> SEQUENCE: 30

Val Phe Ile Ala Asp Ser Asp Gly Lys Leu Asn Phe Lys Glu Trp Ser
1               5                   10                  15

Val Cys Val Gly
            20

<210> SEQ ID NO 31
<211> LENGTH: 20
<212> TYPE: PRT
<213> ORGANISM: Artificial Sequence
<220> FEATURE:
<223> OTHER INFORMATION: synthetic peptide

<400> SEQUENCE: 31

Trp Ser Val Cys Val Gly Leu Thr Thr Tyr Val Asn Asp Tyr Val Leu
1               5                   10                  15

Pro Tyr Leu Ala
            20

<210> SEQ ID NO 32
<211> LENGTH: 18
<212> TYPE: PRT
<213> ORGANISM: Artificial Sequence

```
<220> FEATURE:
<223> OTHER INFORMATION: synthetic peptide

<400> SEQUENCE: 32

Ser Ser His Arg Gly Asn Ile Cys Ile Gly Ala Thr Asn Tyr Val Ala
 1               5                  10                  15

Asp Asn

<210> SEQ ID NO 33
<211> LENGTH: 18
<212> TYPE: PRT
<213> ORGANISM: Artificial Sequence
<220> FEATURE:
<223> OTHER INFORMATION: synthetic peptide

<400> SEQUENCE: 33

Asn Tyr Val Ala Asp Asn Phe Phe Tyr Asn Val Glu Gly Arg Trp Gly
 1               5                  10                  15

Ser Gln

<210> SEQ ID NO 34
<211> LENGTH: 17
<212> TYPE: PRT
<213> ORGANISM: Artificial Sequence
<220> FEATURE:
<223> OTHER INFORMATION: synthetic peptide

<400> SEQUENCE: 34

Gly Arg Trp Gly Ser Gln Arg Ala Val Asn Val Ser Gly Gly Phe Gln
 1               5                  10                  15

Phe

<210> SEQ ID NO 35
<211> LENGTH: 16
<212> TYPE: PRT
<213> ORGANISM: Artificial Sequence
<220> FEATURE:
<223> OTHER INFORMATION: synthetic peptide

<400> SEQUENCE: 35

Leu Asp Ala Met Pro Ala Gly Asn Pro Ala Phe Pro Val Ile Pro Gly
 1               5                  10                  15

<210> SEQ ID NO 36
<211> LENGTH: 16
<212> TYPE: PRT
<213> ORGANISM: Artificial Sequence
<220> FEATURE:
<223> OTHER INFORMATION: synthetic peptide

<400> SEQUENCE: 36

Ala Pro Val Leu Pro Gly Val Asn Pro Glu Gln Thr Gly Trp Cys Ala
 1               5                  10                  15

<210> SEQ ID NO 37
<211> LENGTH: 16
<212> TYPE: PRT
<213> ORGANISM: Artificial Sequence
<220> FEATURE:
<223> OTHER INFORMATION: synthetic peptide

<400> SEQUENCE: 37

Gln Thr Gly Trp Cys Ala Phe Gln Leu Cys Asn Ser Tyr Asp Leu Phe
 1               5                  10                  15
```

```
<210> SEQ ID NO 38
<211> LENGTH: 20
<212> TYPE: PRT
<213> ORGANISM: Artificial Sequence
<220> FEATURE:
<223> OTHER INFORMATION: synthetic peptide

<400> SEQUENCE: 38

Asp Leu Asn Asn Ser Ser Ile Ser Ser Ser Cys Val Phe Ala Thr Ile
 1               5                  10                  15

Ala Leu Gln Glu
        20

<210> SEQ ID NO 39
<211> LENGTH: 20
<212> TYPE: PRT
<213> ORGANISM: Artificial Sequence
<220> FEATURE:
<223> OTHER INFORMATION: synthetic peptide

<400> SEQUENCE: 39

Thr Ile Ala Leu Gln Glu Thr Ser Pro Ala Ala Ile Pro Leu Leu Asp
 1               5                  10                  15

Ile Ala Phe Thr
        20

<210> SEQ ID NO 40
<211> LENGTH: 20
<212> TYPE: PRT
<213> ORGANISM: Artificial Sequence
<220> FEATURE:
<223> OTHER INFORMATION: synthetic peptide

<400> SEQUENCE: 40

Gly Leu Ile Glu Val Gln Ser Asp Tyr Gly Ile Val Trp Gly Leu Ser
 1               5                  10                  15

Leu Gln Lys Val
        20

<210> SEQ ID NO 41
<211> LENGTH: 21
<212> TYPE: PRT
<213> ORGANISM: Artificial Sequence
<220> FEATURE:
<223> OTHER INFORMATION: synthetic peptide

<400> SEQUENCE: 41

Gly Leu Ser Leu Gln Lys Val Leu Trp Lys Asp Gly Val Ser Phe Val
 1               5                  10                  15

Gly Val Ser Ala Asp
        20

<210> SEQ ID NO 42
<211> LENGTH: 20
<212> TYPE: PRT
<213> ORGANISM: Artificial Sequence
<220> FEATURE:
<223> OTHER INFORMATION: synthetic peptide

<400> SEQUENCE: 42

Phe Val Gly Val Ser Ala Asp Tyr Arg His Gly Ser Ser Pro Ile Asn
 1               5                  10                  15

Tyr Ile Ile Val
        20
```

<210> SEQ ID NO 43
<211> LENGTH: 20
<212> TYPE: PRT
<213> ORGANISM: Artificial Sequence
<220> FEATURE:
<223> OTHER INFORMATION: synthetic peptide

<400> SEQUENCE: 43

Ile Tyr Phe Asp Ala Thr Asp Gly Asn Leu Ser Tyr Lys Glu Trp Ser
1               5                   10                  15

Ala Ser Ile Gly
            20

<210> SEQ ID NO 44
<211> LENGTH: 20
<212> TYPE: PRT
<213> ORGANISM: Artificial Sequence
<220> FEATURE:
<223> OTHER INFORMATION: synthetic peptide

<400> SEQUENCE: 44

Trp Ser Ala Ser Ile Gly Ile Ser Thr Tyr Leu Asn Asp Tyr Val Leu
1               5                   10                  15

Pro Tyr Ala Ser
            20

<210> SEQ ID NO 45
<211> LENGTH: 21
<212> TYPE: PRT
<213> ORGANISM: Artificial Sequence
<220> FEATURE:
<223> OTHER INFORMATION: synthetic peptide

<400> SEQUENCE: 45

Val Leu Pro Tyr Ala Ser Val Ser Ile Gly Asn Thr Ser Arg Lys Ala
1               5                   10                  15

Pro Ser Asp Ser Phe
            20

<210> SEQ ID NO 46
<211> LENGTH: 18
<212> TYPE: PRT
<213> ORGANISM: Artificial Sequence
<220> FEATURE:
<223> OTHER INFORMATION: synthetic peptide

<400> SEQUENCE: 46

Phe Thr Asn Phe Lys Phe Lys Ile Arg Lys Ile Thr Asn Phe Asp Arg
1               5                   10                  15

Val Asn

<210> SEQ ID NO 47
<211> LENGTH: 315
<212> TYPE: PRT
<213> ORGANISM: C. trachomatis

<400> SEQUENCE: 47

Ala Met Pro Ala Gly Asn Pro Ala Asn Pro Val Ile Pro Gly Ile Asn
1               5                   10                  15

Ile Glu Gln Lys Asn Ala Cys Ser Phe Asp Leu Cys Asn Ser Tyr Asp
            20                  25                  30

Val Leu Ser Ala Leu Ser Gly Asn Leu Lys Leu Cys Phe Cys Gly Asp

-continued

```
                    35                    40                    45
Tyr Ile Asn Ser Glu Glu Ala Gln Val Lys Asp Val Pro Val Val Thr
    50                  55                  60

Ser Val Thr Thr Ala Gly Val Gly Pro Ser Pro Asp Ile Thr Ser Thr
65                  70                  75                  80

Thr Lys Thr Arg Asn Phe Asp Leu Val Asn Cys Asn Leu Asn Thr Asn
                85                  90                  95

Cys Val Ala Val Ala Asn Ser Leu Pro Asp Arg Ser Leu Ser Ala Ile
            100                 105                 110

Pro Leu Asn Asp Val Ser Phe Glu Val Lys Val Gly Gly Leu Lys Gln
        115                 120                 125

Tyr Tyr Pro Leu Pro Met Asn Ala Tyr Arg Asp Phe Thr Ser Glu Pro
    130                 135                 140

Leu Asn Ser Glu Ser Glu Val Thr Asp Gly Met Ile Glu Val Gln Ser
145                 150                 155                 160

Asn Tyr Gly Asn Val Trp Asp Val Ser Leu Lys Lys Val Ile Trp Lys
                165                 170                 175

Asp Gly Val Ser Asn Val Gly Val Gly Ala Asp Tyr Arg His Ala Ser
            180                 185                 190

Cys Pro Ile Asp Tyr Ile Ile Ala Asn Ser Gln Ala Asn Pro Glu Val
        195                 200                 205

Phe Ile Ala Asp Ser Asp Gly Lys Leu Asn Phe Lys Glu Trp Ser Val
    210                 215                 220

Cys Val Gly Leu Thr Thr Tyr Val Asn Asp Tyr Val Leu Pro Tyr Leu
225                 230                 235                 240

Ala Asn Ser Ile Gly Ser Val Ser Arg Gln Ala Pro Asp Asp Ser Phe
                245                 250                 255

Lys Lys Leu Glu Asp Arg Phe Thr Asn Leu Lys Asn Lys Val Arg Lys
            260                 265                 270

Ile Thr Ser Ser His Arg Gly Asn Ile Cys Ile Gly Ala Thr Asn Tyr
        275                 280                 285

Val Ala Asp Asn Phe Phe Tyr Asn Val Glu Gly Arg Trp Gly Ser Gln
    290                 295                 300

Arg Ala Val Asn Val Ser Gly Gly Phe Gln Phe
305                 310                 315
```